United States Patent
Jablonski et al.

(10) Patent No.: US 7,812,021 B2
(45) Date of Patent: Oct. 12, 2010

(54) PYRROLIDINE ARYL-ETHER AS NK3 RECEPTOR ANTAGONISTS

(75) Inventors: Philippe Jablonski, Steinbrunn-le-Haut (FR); Kenichi Kawasaki, Kanagawa-ken (JP); Henner Knust, Rheinfelden (DE); Anja Limberg, Basel (CH); Matthias Nettekoven, Grenzach-Wyhlen (DE); Hasane Ratni, Habsheim (FR); Claus Riemer, Freiburg (DE); Xihan Wu, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/195,545

(22) Filed: Aug. 21, 2008

(65) Prior Publication Data

US 2009/0054644 A1 Feb. 26, 2009

(30) Foreign Application Priority Data

Aug. 22, 2007 (EP) .................................. 07114790

(51) Int. Cl.
- *A61K 31/496* (2006.01)
- *A61K 31/454* (2006.01)
- *A61K 31/506* (2006.01)
- *A61K 31/5377* (2006.01)
- *C07D 207/12* (2006.01)
- *C07D 401/12* (2006.01)
- *C07D 403/12* (2006.01)
- *C07D 487/04* (2006.01)
- *C07D 491/107* (2006.01)

(52) U.S. Cl. ............... 514/235.5; 514/249; 514/252.19; 514/253.09; 514/254.02; 514/254.05; 514/278; 514/316; 514/326; 514/338; 544/130; 544/141; 544/58.2; 544/58.5; 544/295; 544/349; 544/354; 544/364; 544/370; 544/372; 546/15; 546/187; 546/194; 546/208; 546/276.7

(58) Field of Classification Search ........................ None
See application file for complete search history.

(56) References Cited

U.S. PATENT DOCUMENTS 5,576,333 A 11/1996 Miller

2006/0020011 A1 1/2006 Wu et al.

FOREIGN PATENT DOCUMENTS

| EP | 0714891 | 6/1996 |
|----|---------|--------|
| GB | 2000136 | 1/1979 |
| WO | WO 98/27086 | 6/1998 |

OTHER PUBLICATIONS

Tooney et al., Neurosci. Letters, 2000, vol. 283 pp. 185-188.
Giardina et al., Exp. Opin. Ther. Patents, 2000, vol. 10, pp. 939-960.
Jung et al., Neuroscience, 1996, vol. 74 pp. 403-414.
Leslie et al., Neuropeptides, 1998, vol. 32 pp. 481-488.
Kamali et al., Current Opinion in Investigational Drugs, 2001, vol. 2(7) pp. 950-956.
Dega-Szafran et al., J. Molecular Structure, 2001, vol. 560 p. 261.

*Primary Examiner*—Emily Bernhardt
(74) *Attorney, Agent, or Firm*—George W. Johnstone; Patricia S. Rocha-Tramaloni; Kimberly J. Prior

(57) ABSTRACT

The invention relates to a compound of general formula

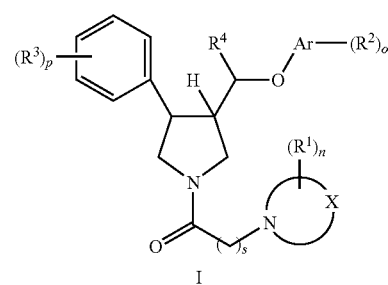

I wherein
Ar, $R^1$, $R^2$, $R^3$, $R^4$, n, o, p, s, X and

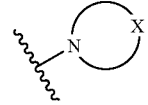

are as defined herein or to a pharmaceutically active salt thereof, including all stereoisomeric forms, individual diastereoisomers and enantiomers of the compound of formula (I) as well as racemic and non-racemic mixtures thereof. The compounds are high potential NK-3 receptor antagonists for the treatment of depression, pain, psychosis, Parkinson's disease, schizophrenia, anxiety and attention deficit hyperactivity disorder (ADHD).

16 Claims, No Drawings

PYRROLIDINE ARYL-ETHER AS NK3 RECEPTOR ANTAGONISTS

PRIORITY TO RELATED APPLICATION(S)

This application claims the benefit of European Patent Application No. 07114790.4, filed Aug. 22, 2007, which is hereby incorporated by reference in its entirety.

BACKGROUND OF THE INVENTION

The three main mammalian tachykinins, substance P (SP), neurokinin A (NKA) and neurokinin B (NKB) belong to the family of neuropeptides sharing the common COOH-terminal pentapeptide sequence of Phe-X-Gly-Leu-Met-$NH_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease schizophrenia and pain (*Neurosci. Letters*, 2000, 283, 185-188; *Exp. Opin. Ther. Patents* 2000, 10, 939-960; *Neuroscience*, 1996, 74, 403-414; *Neuropeptides*, 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs*, 2001, 2(7), 950-956 and *Psychiatric Disorders Study* 4, *Schizophrenia*, June 2003, Decision Recources, Inc., Waltham, Mass.). The proposed drug SR 142,801 has been shown in a phase II trial as active on positive symptoms of schizophrenia, such as altered behaviour, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 *and Current Opinion in Investigational Drugs*, 2001, 2(7), 950-956 956 *and Psychiatric Disorders Study* 4, *Schizophrenia*, June 2003, Decision Recources, Inc., Waltham, Mass.).

SUMMARY OF THE INVENTION

The invention provides a compound of formula

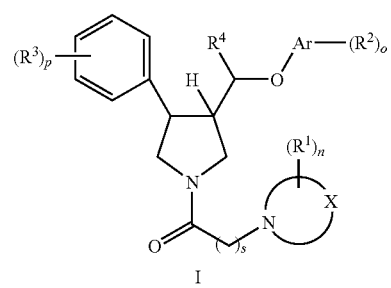

I wherein
Ar is aryl or a five or six membered heteroaryl;

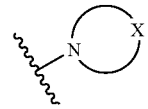

is a six to nine membered mono or bi-heterocyclic group, wherein X is a carbon atom, $SO_2$ or a further hetero atom, selected from the group consisting of N and O;
if X is a carbon atom, O, $SO_2$ or unsubstituted N, then
$R^1$ is hydrogen, hydroxy, cyano, —$(CH_2)_q$—OH, —$(CH_2)_q$—NRR', —$(CH_2)$q-CN, lower alkyl, —$S(O)_2$-lower alkyl, —NR—$S(O)_2$-lower alkyl, —C(O)-lower alkyl, —NR—C(O)-lower alkyl, phenyl, or piperidinyl-2-one;
if X is a N-atom, substituted by $R^1$, then
$R^1$ is hydrogen, —$(CH_2)_q$—OH, $(CH_2)_q$—NRR', —$(CH_2)$q-CN, lower alkyl, —$S(O)_2$-lower alkyl, aryl or a five or six membered heteroaryl or —C(O)-lower alkyl provided that q is 2 or 3.
R and R' are each independently hydrogen or lower alkyl;
$R^2$ is hydrogen, halogen, lower alkyl, cyano, lower alkoxy substituted by halogen, lower alkyl substituted by halogen or is a five or six membered heteroaryl;

R³ is hydrogen or halogen;
R⁴ is hydrogen or lower alkyl;
n is 1 or 2; where n is 2, R¹ is the same or different;
o is 1 or 2; where o is 2, R² is the same or different;
p is 1 or 2; where p is 2, R³ is the same or different;
q is 1, 2 or 3; and
s is 0, 1, 2, 3 or 4;
or to a pharmaceutically active salt thereof.

The invention includes all stereoisomeric forms, including individual diastereoisomers and enantiomers of the compound of formula (I) as well as racemic and non-racemic mixtures thereof.

The invention also provides pharmaceutical compositions containing a therapeutically effective amount of a compound of formula I and a pharmaceutically acceptable carrier. The invention further provides methods for the preparation of compounds and compositions of the invention.

The present compounds are high potential NK-3 receptor antagonists for the treatment of depression, pain, psychosis, Parkinson's disease, schizophrenia, anxiety and attention deficit hyperactivity disorder (ADHD).

The preferred indications using the compounds of the present invention are depression, psychosis, Parkinson's disease, schizophrenia, anxiety and attention deficit hyperactivity disorder (ADHD).

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon group containing from 1-8 carbon atoms, for example, methyl, ethyl, propyl, isopropyl, n-butyl, i-butyl, t-butyl and the like. Preferred lower alkyl groups are groups with 1-4 carbon atoms.

The term "halogen" denotes chlorine, iodine, fluorine and bromine.

The term "lower alkyl substituted by halogen" denotes an alkyl group as defined above, wherein at least one hydrogen atom is replaced by halogen, for example —CF₃, —CHF₂, —CH₂F, —CH₂CF₃, —CH₂CH₂CF₃, —CH₂CF₂CF₃ and the like. Preferred lower alkyl substituted by halogen groups are groups having 1-4 carbon atoms.

The term "lower alkoxy" denotes an alkyl group as defined above that is attached via an oxygen atom, for example, methoxy, ethoxy, propoxy, isopropoxy, n-butoxy, i-butoxy, 2-butoxy, t-butoxy and the like. Preferred alkoxy groups are groups with 1-4 carbon atoms.

The term "lower alkoxy substituted by halogen" denotes an alkoxy group as defined above wherein at least one hydrogen atom is replaced by halogen. Preferred lower alkoxy substituted by halogen groups are groups having 1-4 carbon atoms.

The term "aryl" denotes a cyclic aromatic hydrocarbon radical consisting of one or more fused rings containing 6-14 ring carbon atoms in which at feast one ring is aromatic in nature, for example phenyl, benzyl, naphthyl or indanyl. Preferred is the phenyl group.

The term "five or six membered heteroaryl" denotes a cyclic aromatic radical, which contains at least one heteroatom, selected from N, O and S, for example quinoxalinyl, pyrazinyl, pyrazolyl, pyridinyl, pyridyl, pyrimidinyl, oxadiazolyl, triazolyl, tetrazolyl, thiazolyl, thiadiazolyl, thiophenyl, isoxazolyl, pyrrolyl, furanyl or imidazolyl. Preferred heteroaryl groups are pyridyl, primidinyl or imidazolyl.

The term "six membered heterocyclic group, wherein X may be a carbon atom or a further hetero atom, selected from the group consisting of N, O and S" denotes the following groups: piperazinyl, morpholinyl, thiomorpholinyl, piperidinyl, 2-oxa-6-aza-spiro[3.3]hept-6-yl, 2-oxa-5-aza-bicyclo[2.2.1]hept-5-yl or hexahydro-pyrrolo[1.2-a]pyrazin-6-one.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

The following groups of compounds of formula I are preferred:
A compound of formula I, wherein (R³)$_p$ is 3,4-di-chloro.
A compound of formula I, wherein

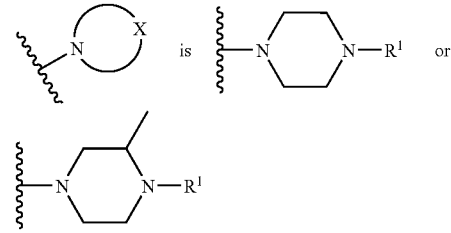

and Ar is phenyl, for example the following compounds
{(3RS,4SR)-3-(3,4-dichloro-phenyl)-4-[(RS)-1-(4-trifluoromethyl-phenoxy)-ethyl]-pyrrolidin-1-yl}-(4-methanesulfonyl-piperazin-1-yl)-methanone,
{(3RS,4SR)-3-(3,4-dichloro-phenyl)-4-[(SR)-1-(4-trifluoromethyl-phenoxy)-ethyl]-pyrrolidin-1-yl}-(4-methanesulfonyl-piperazin-1-yl)-methanone,
2-(4-acetyl-piperazin-1-yl)-1-{(3RS,4SR)-3-(3,4-dichloro-phenyl)-4-[(RS)-1-(4-trifluoromethyl-phenoxy)-ethyl]-pyrrolidin-1-yl}-ethanone,
{(3RS,4SR)-3-(3,4-dichloro-phenyl)-4-[(RS)-1-(4-trifluoromethyl-phenoxy)-ethyl]-pyrrolidin-1-yl}-((R)-4-methanesulfonyl-3-methyl-piperazin-1-yl)-methanone,
[(3SR,4RS)-3-[(RS)-1-(3,4-dichloro-phenoxy)-ethyl]-4-(3,4-dichloro-phenyl)-pyrrolidin-1-yl]-(4-methanesulfonyl-piperazin-1-yl)-methanone,
[(3RS,4SR)-3-(3,4-dichloro-phenyl)-4-((RS)-1-p-tolyloxy-ethyl)-pyrrolidin-1-yl]-(4-methanesulfonyl-piperazin-1-yl)-methanone,
4-{(RS)-1-[(3SR,4RS)-4-(3,4-dichloro-phenyl)-1-(4-methanesulfonyl-piperazine-1-carbonyl)-pyrrolidin-3-yl]-ethoxy}-benzonitrile,
{(3RS,4SR)-3-(3,4-dichloro-phenyl)-4-[(RS)-1-(4-fluoro-phenoxy)-ethyl]-pyrrolidin-1-yl}-(4-methanesulfonyl-piperazin-1-yl)-methanone,
[(3SR,4RS)-3-[(RS)-1-(4-chloro-phenoxy)-ethyl]-4-(3,4-dichloro-phenyl)-pyrrolidin-1-yl]-(4-methanesulfonyl-piperazin-1-yl)-methanone,

[(3SR,4RS)-3-[(RS)-1-(3-chloro-4-fluoro-phenoxy)-ethyl]-4-(3,4-dichloro-phenyl)-pyrrolidin-1-yl]-(4-methanesulfonyl-piperazin-1-yl)-methanone, 4-{(SR)-1-[(3SR,4RS)-4-(3,4-dichloro-phenyl)-1-(4-methanesulfonyl-piperazine-1-carbonyl)-pyrrolidin-3-yl]-ethoxy}-benzonitrile, {(3RS,4SR)-3-(3,4-dichloro-phenyl)-4-[(SR)-1-(4-fluoro-phenoxy)-ethyl]-pyrrolidin-1-yl}-(4-methanesulfonyl-piperazin-1-yl)-methanone,

[(3SR,4RS)-3-[(SR)-1-(4-chloro-phenoxy)-ethyl]-4-(3,4-dichloro-phenyl)-pyrrolidin-1-yl]-(4-methanesulfonyl-piperazin-1-3)-methanone, {(3RS,4SR)-3-(3,4-dichloro-phenyl)-4-[(RS)-1-(4-trifluoromethyl-phenoxy)-ethyl]-pyrrolidin-1-yl}-[4-(2-dimethylamino-ethyl)-piperazin-1-yl]-methanone, and 2-(4-acetyl-piperazin-1-yl)-1-[(3SR,4RS)-3-[(RS)-1-(4-chloro-phenoxy)-ethyl]-4-(3,4-dichloro-phenyl)-pyrrolidin-1-yl]-ethanone.

A compound of formula I, wherein

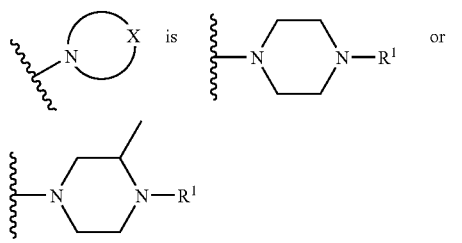

and Ar is pyridyl, for example

[(3SR,4RS)-3-[(RS)-1-(5-chloro-pyridin-2-yloxy)-ethyl]-4-(3,4-dichloro-phenyl)-pyrrolidin-1-yl]-(4-methanesulfonyl-piperazin-1-yl)-methanone,

[(3SR,4RS)-3-[(RS)-1-(5-chloro-pyridin-2-yloxy)-ethyl]-4-(3,4-dichloro-phenyl)-pyrrolidin-1-yl]-((R)-4-methanesulfonyl-3-methyl-piperazin-1-yl)-methanone,

[(3SR,4RS)-3-[(RS)-1-(5-chloro-pyridin-2-yloxy)-ethyl]-4-(3,4-dichloro-phenyl)-pyrrolidin-1-yl]-[4-(2-dimethylamino-ethyl)-piperazin-1-yl]-methanone, {(3RS,4SR)-3-(3,4-dichloro-phenyl)-4-[(SR)-1-(5-fluoro-pyridin-2-yloxy)-ethyl]-pyrrolidin-1-yl}-(4-methanesulfonyl-piperazin-1-yl)-methanone, {(3RS,4SR)-3-(3,4-dichloro-phenyl)-4-[(RS)-1-(5-fluoro-pyridin-2-yloxy)-ethyl]-pyrrolidin-1-yl}-(4-methanesulfonyl-piperazin-1-yl)-methanone,

[(3SR,4RS)-3-(5-chloro-pyridin-2-yloxymethyl)-4-(3,4-dichloro-phenyl)-pyrrolidin-1-yl]-(4-methanesulfonyl-piperazin-1-yl)-methanone, and {(3RS,4SR)-3-(3,4-dichloro-phenyl)-4-[(SR)-1-(5-trifluoromethyl-pyridin-2-yloxy)-ethyl]-pyrrolidin-1-yl}-(4-methanesulfonyl-piperazin-1-yl)-methanone.

A compound of formula I, wherein

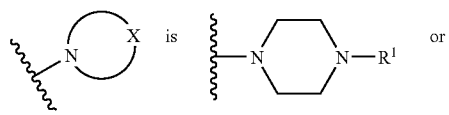

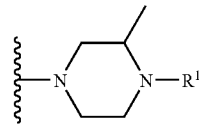

and Ar is pyrimidinyl, for example

{(3RS,4SR)-3-(3,4-dichloro-phenyl)-4-[(RS)-1 (pyrimidin-2-yloxy)-ethyl]-pyrrolidin-1-yl}-(4-methanesulfonyl-piperazin-1-yl)-methanone, {(3RS,4SR)-3-(3,4-dichloro-phenyl)-4-[(RS)-1-(5-fluoro-pyrimidin-2-yloxy)-ethyl]-pyrrolidin-1-yl}-(4-methanesulfonyl-piperazin-1-yl)-methanone, and

[(3SR,4RS)-3-[(RS)-1-(5-chloro-pyrimidin-2-yloxy)-ethyl]-4-(3,4-dichloro-phenyl)-pyrrolidin-1-yl]-(4-methanesulfonyl-piperazin-1-yl)-methanone.

A compound of formula I, wherein

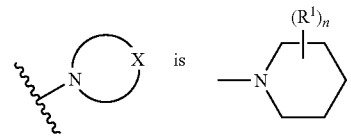

and Ar is phenyl, for example

N-(1-{(3RS,4SR)-3-(3,4-dichloro-phenyl)-4-[(RS)-1-(4-trifluoromethyl-phenoxy)-ethyl]-pyrrolidine-1-carbonyl}-piperidin-4-yl)-N-methyl-methanesulfonamide, N-[1-(2-{(3RS,4SR)-3-(3,4-dichloro-phenyl)-4-[(RS)-1-(4-trifluoromethyl-phenoxy)-ethyl]-pyrrolidin-1-yl}-2-oxo-ethyl)-piperidin-4-yl]-N-methyl-methanesulfonamide, N-[1-(2-{(3RS,4SR)-3-(3,4-dichloro-phenyl)-4-[(RS)-1-(4-trifluoromethyl-phenoxy)-ethyl]-pyrrolidin-1-yl}-2-oxo-ethyl)-piperidin-4-yl]-acetamide, N-(1-{2-[(3SR,4RS)-3-[(RS)-1-(4-chloro-phenoxy)-ethyl]-4-(3,4-dichloro-phenyl)-pyrrolidin-1-yl]-2-oxo-ethyl}-4-phenyl-piperidin-4-yl)-acetamide, N-(1-{2-[(3SR,4RS)-3-[(RS)-1-(4-chloro-phenoxy)-ethyl]-4-(3,4-dichloro-phenyl)-pyrrolidin-1-yl]-2-oxo-ethyl}-piperidin-4-yl)-N-methyl-acetamide, and 1-[(3SR,4RS)-3-[(RS)-1-(4-chloro-phenoxy)-ethyl]-4-(3,4-dichloro-phenyl)-pyrrolidin-1-yl]-2-(4-hydroxymethyl-piperidin-1-yl)-ethanone.

A compound of formula I, wherein

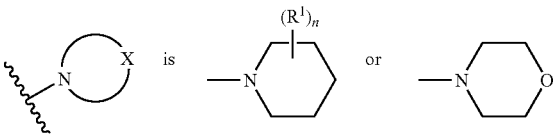

and Ar is pyridyl, for example

1-[(3SR,4RS)-3-[(RS)-1-(5-chloro-pyridin-2-yloxy)-ethyl]-4-(3,4-dichloro-phenyl)-pyrrolidin-1-yl]-5-morpholin-4-yl-pentan-1-one, 6-{(SR)-1-[(3RS,4SR)-1-[2-(4-cyano-piperidin-1-yl)-acetyl]-4-(3,4-dichloro-phenyl)-pyrrolidin-3-yl]-ethoxy}-nicotinonitrile, and 6-{(SR)-1-[(3RS,4SR)-1-(4-cyano-piperidine-1-carbonyl)-4-(3,4-dichloro-phenyl)-pyrrolidin-3-yl]-ethoxy}-nicotinonitrile.

A compound of formula I, wherein

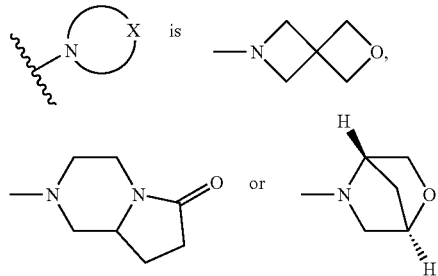 is and Ar is pyridyl, for example
[(3SR,4RS)-3-[(RS)-1-(5-chloro-pyridin-2-yloxy)-ethyl]-4-(3,4-dichloro-phenyl)-pyrrolidin-1-yl]-(2-oxa-6-aza-spiro[3.3]hept-6-yl)-methanone,
2-[(3SR,4RS)-3-[(RS)-1-(5-chloro-pyridin-2-yloxy)-ethyl]-4-(3,4-dichloro-phenyl)-pyrrolidine-1-carbonyl]-hexahydro-pyrrolo[1,2-a]pyrazin-6-one,
1-[(3S,4R)-3-[(R)-1-(5-chloro-pyridin-2-yloxy)-ethyl]-4-(3,4-dichloro-phenyl)-pyrrolidin-1-yl]-2-(2-oxa-5-aza-bicyclo[2.2.1]hept-5-yl)-ethanone, and
{(3SR,4RS)-3-(3,4-dichloro-phenyl)-4-[(SR)-1-(5-trifluoromethyl-pyridin-2-yloxy)-ethyl]-pyrrolidin-1-yl}-(2-oxa-5-aza-bicyclo[2.2.1]hept-5-yl)-methanone.

A further embodiment of the invention are compounds of formula

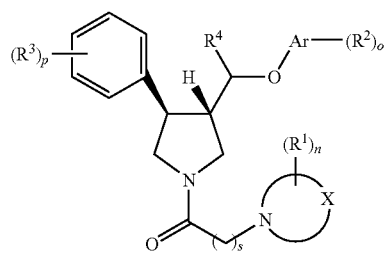

I-1 wherein
Ar is aryl or a five or six membered heteroaryl;

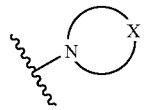

is a six or seven membered heterocyclic group, wherein X is a carbon atom, $SO_2$ or a further hetero atom, selected from the group consisting of N and O;
if X is a carbon atom, O, $SO_2$ or unsubstituted N, then
$R^1$ is hydrogen, hydroxy, cyano, —$(CH_2)_q$—OH, —$(CH_2)_q$—NRR', —$(CH_2)$q-CN, lower alkyl, —$S(O)_2$-lower alkyl, —NR—$S(O)_2$-lower alkyl, —C(O) lower alkyl, —NR—C(O)-lower alkyl, or a piperidinyl-2-one;
if X is a N-atom, substituted by $R^1$, then
$R^1$ is hydrogen, —$(CH_2)_q$—OH, —$(CH_2)_q$—NRR', —$(CH_2)$q-CN, lower alkyl, —$S(O)_2$-lower alkyl, aryl, a five or six membered heteroaryl, or —C(O)-lower alkyl, provided than q is 2, 3 or 4

R and R' are each independently hydrogen or lower alkyl;
$R^2$ is hydrogen, halogen, lower alkyl, cyano, lower alkoxy substituted by halogen, lower alkyl substituted by halogen or is a five or six membered heteroaryl;
$R^3$ is hydrogen or halogen;
$R^4$ is hydrogen or lower alkyl;
n is 1 or 2; in case n is 2, each $R^1$ is the same or different;
o is 1 or 2; in case o is 2, each $R^2$ is the same or different;
p is 1 or 2; in case p is 2, each $R^3$ is the same or different;
q is 1, 2 or 3; and
s is 0, 1, 2, 3 or 4;

or to a pharmaceutically active salt thereof.

The invention includes all stereoisomeric forms, including individual diastereoisomers and enantiomers of the compound of formula (I) as well as racemic and non-racemic mixtures thereof.

The preparation of compounds of formula I of the present invention can be carried out in sequential or convergent synthetic routes. Syntheses of the compounds of the invention are shown in the following schemes 1 to 4. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1-4, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by processes described below, which processes comprise a) reacting a compound of formula

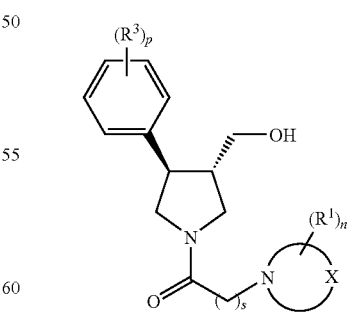

VII with a compound of formula

HO—Ar—$(R^2)_o$ to obtain a compound of formula

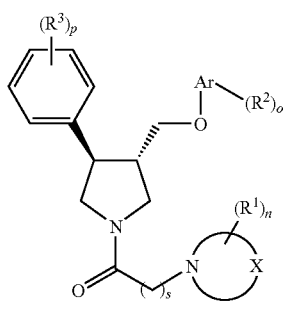

I-C wherein the definitions have same meanings as described above, or b) reacting a compound of formula

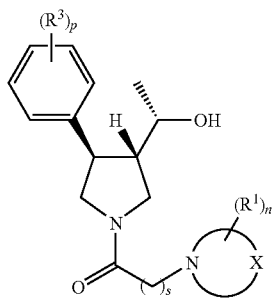

XII-B with a compound of formula

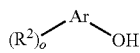

to obtain a compound of formula

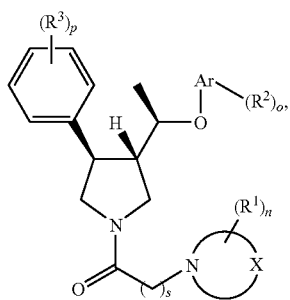

I-B wherein the definitions are as above, or c) reacting a compound of formula

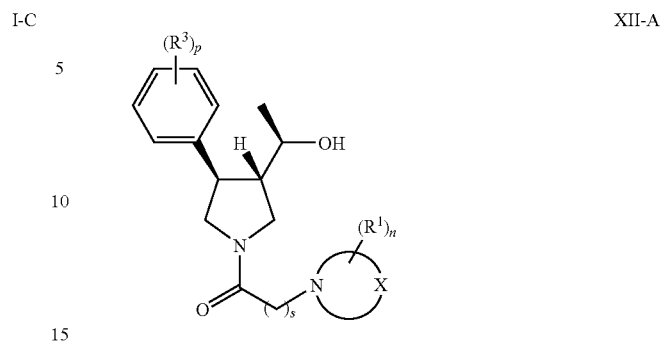

XII-A with a compound of formula

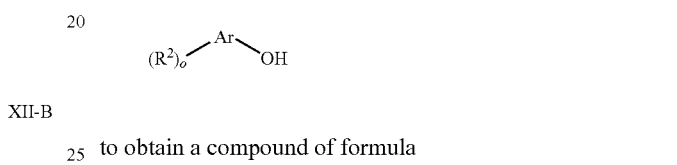

to obtain a compound of formula

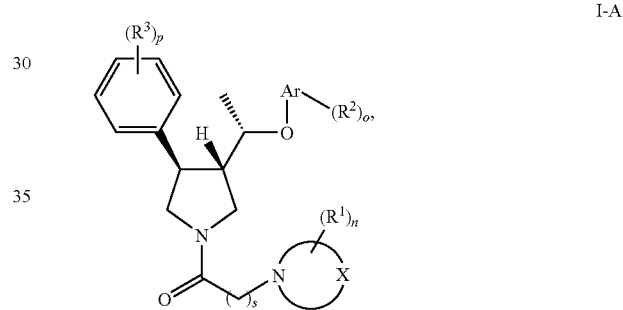

I-A wherein the definitions are as above, d) reacting a compound of formula

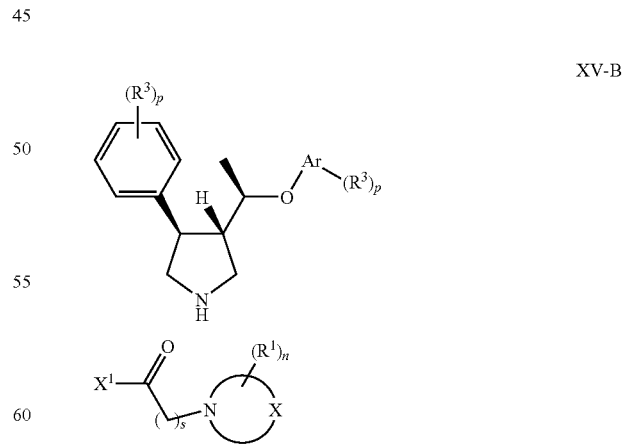

XV-B with a compound of formula to obtain a compound of formula

I-B

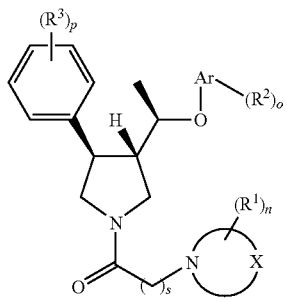

wherein $X^1$ is halogen, and the other definitions are as above, e) reacting a compound of formula

XVI-B

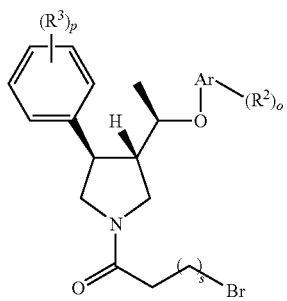

with a compound of formula

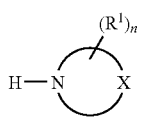

to obtain a compound of formula

I-D

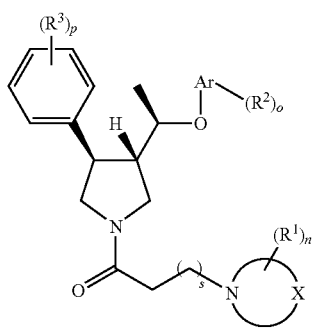

wherein the definitions are as above, and if desired, converting the compounds obtained into pharmaceutically acceptable acid addition salts.

The process is described in more detail in schemes 1 to 4 and in examples 1-73.

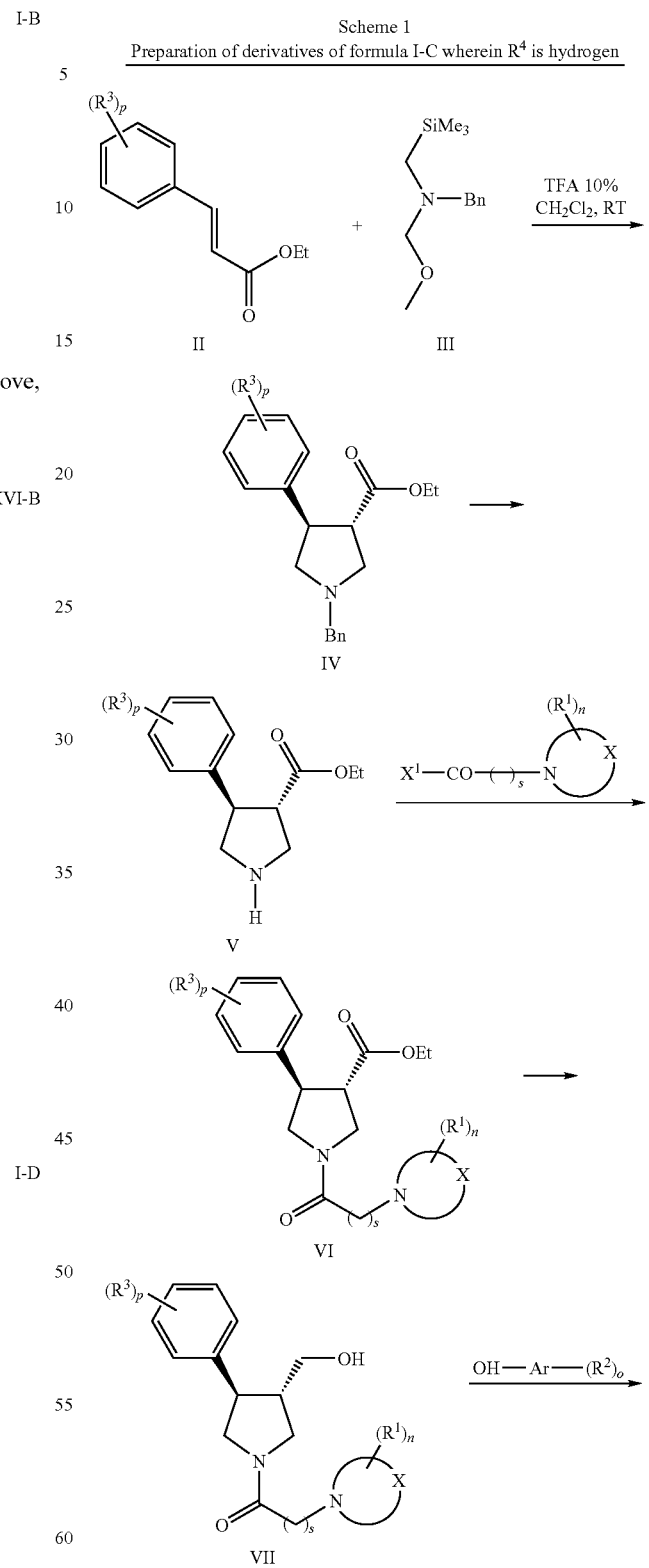

-continued

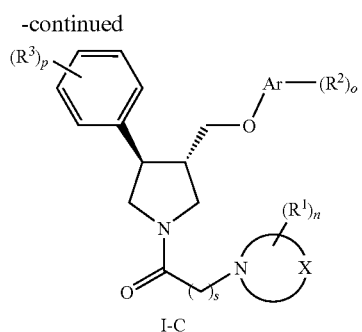

$X^1$ is halogen and the other definitions are as described above.

The 3,4-disubstituted pyrrolidines IV were prepared via a stereospecific 1,3-dipolar cycloaddition between the (E)-3-substituted phenyl-acrylic acid ethyl ester derivatives II and the azomethine ylide generated in situ from the N-(methoxymethyl)-N-(phenylmethyl)-N-(trimethylsilyl)methylamine III in the presence of a catalytic amount of acid, such as TFA. Selective N-debenzylation was then carried out using several known procedures which are compatible with the substitution patterns of the aromatic ring to afford V. A coupling with a suitable acid chloride, carboxylic acid or carbamoyl chloride using known methods gave VI. Reduction of the ester moiety using standard conditions for example LiBH$_4$ yielded the alcohol VII. Standard Mitsunobu reaction with for example a phenol, pyridin-ol or pyrimidin-ol gave the aryl-ether I-C.

Scheme 2
Preparation of derivatives of formula I-A and I-B wherein $R^4$ is methyl:

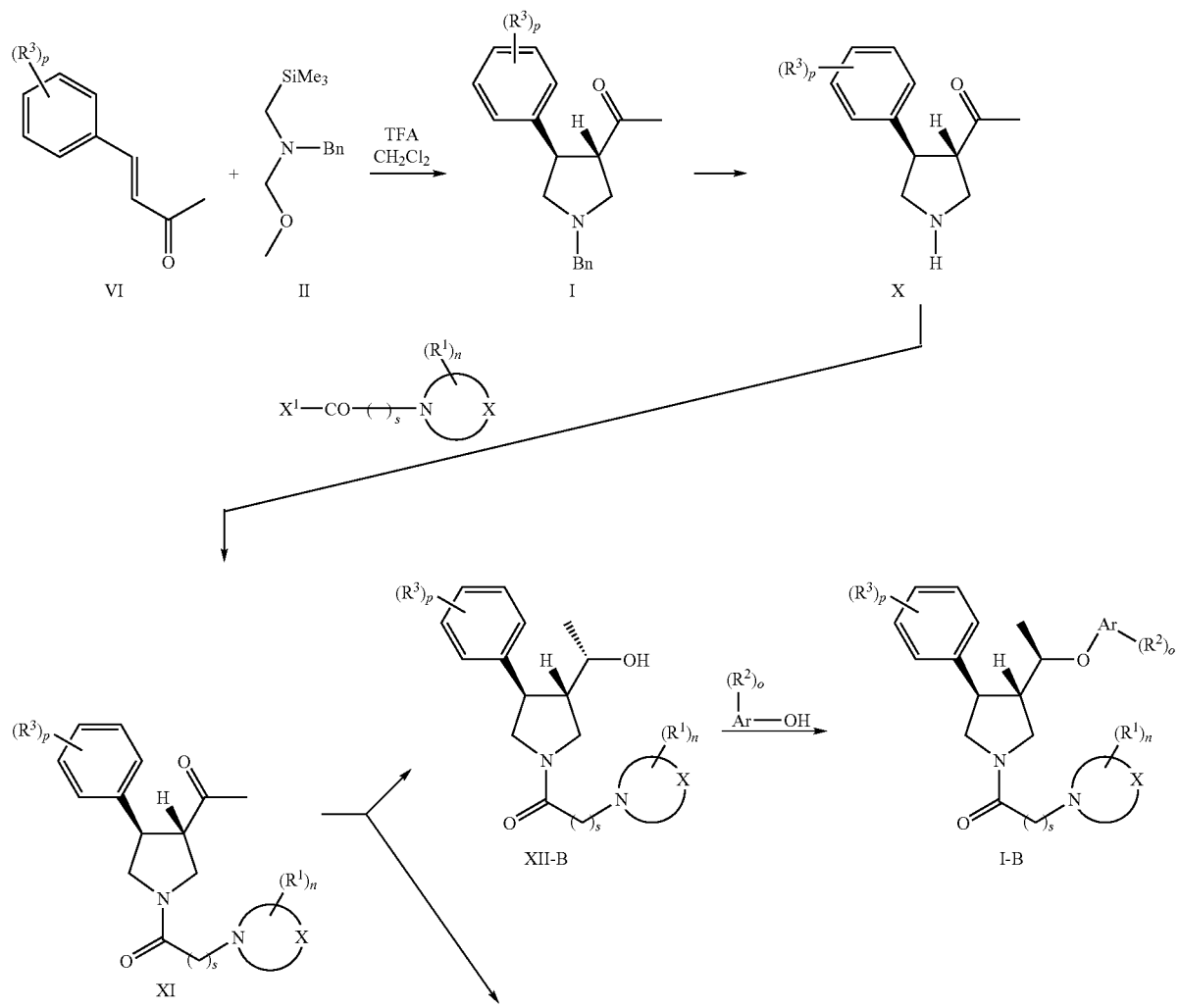

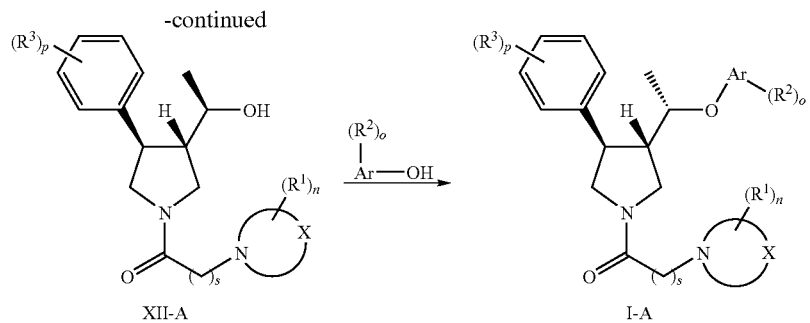

$X^1$ is halogen and the other definitions are as described above.

The 3,4-disubstituted pyrrolidines IX were prepared via a stereo specific 1,3-dipolar cycloaddition between substituted (E)-4-phenyl-but-3-en-2-one derivative VIII and the azomethine ylide generated in situ from the N-(methoxymethyl)-N-(phenylmethyl)-N-(trimethylsilyl)methylamine III in the presence of a catalytic amount of acid, such as TFA. Selective N-debenzylation was then carried out using several known procedures which are compatible with the substitution patterns of the aromatic ring to afford X. A coupling with a suitable acid chloride, carboxylic acid or carbamoyl chloride using known methods gave XI. Reduction of the acetyl moiety using standard conditions for example $LiBH_4$ yielded the two diasteroisomers XII-A and XII-B which were subsequently separated by column chromatography. Each of the diastereoisomers were then separately converted to the final derivatives I-A and I-B via a standard Mitsunobu reaction with for example a phenol, pyridin-ol or pyrimidin-ol.

Scheme 3
Preparation of derivatives of formula I-A and I-B wherein R⁴ is methyl:
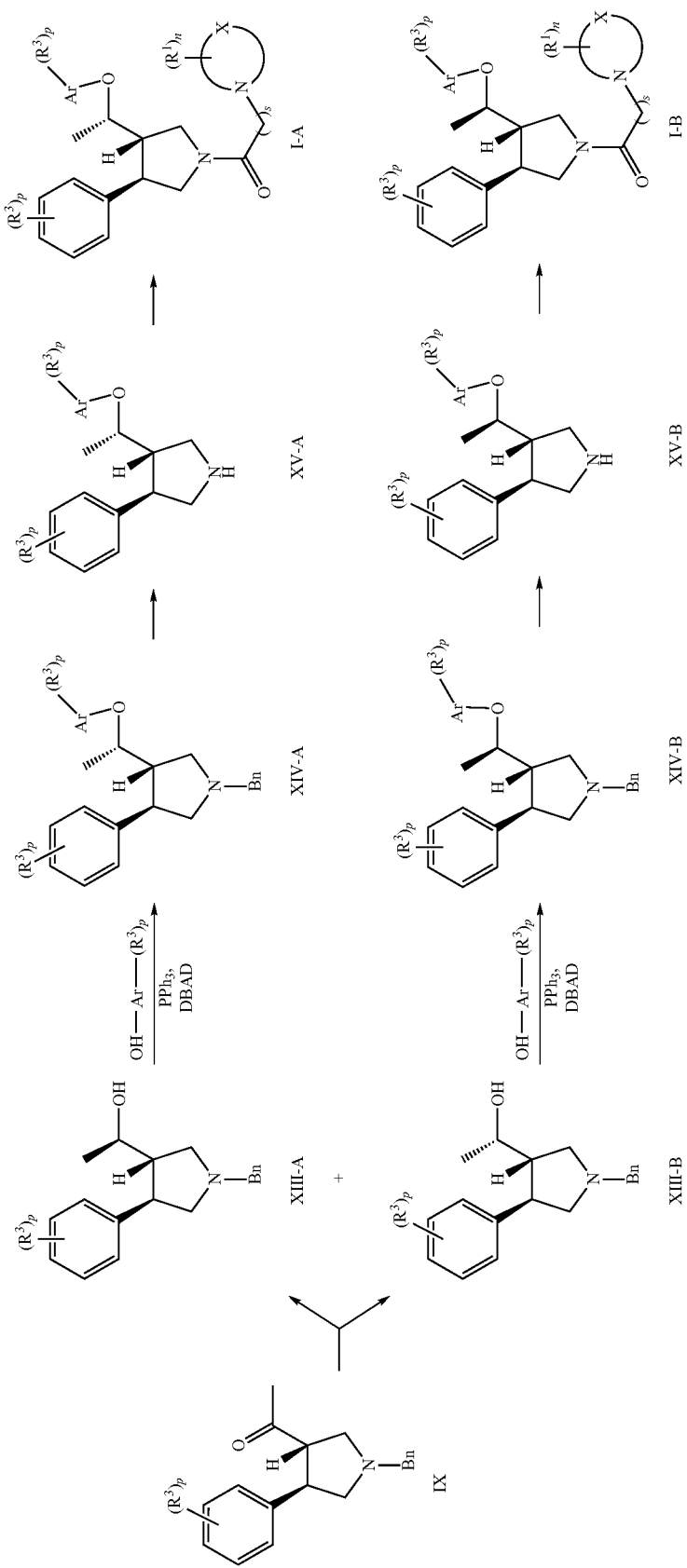

Alternatively, reduction of the acetyl moiety of TX was achieved with for instance LiAlH₄, and produced the two diastereoisomeres XIII-A and XIII-B which were separated by column chromatography. Both underwent a standard Mitsunobu reaction with for example a phenol, pyridin-ol or pyrimidin-ol to give the aryl-ether derivatives XIV-A and XIV-B. Selective N-debenzylation using several known procedures which are compatible with the substitution patterns of the aromatic rings to afforded respectively XV-A and XV-B. Coupling with a suitable acid chloride, carboxylic acid or carbamoyl chloride using known methods yielded respectively I-A and I-B.

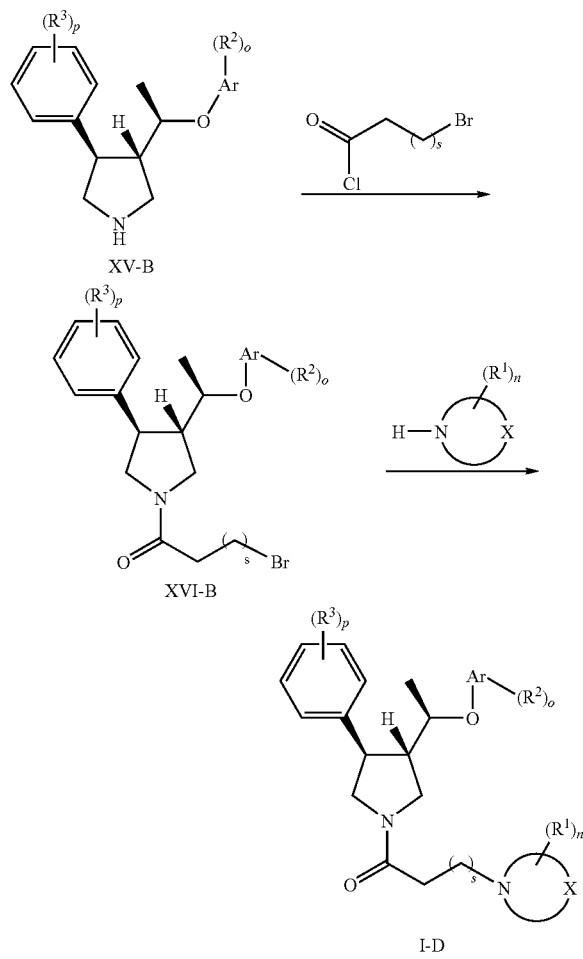

Scheme 4
Preparation of derivatives of formula I-D, wherein R⁴ is methyl

Alternatively, derivatives XV-B could react with bromoacetyl chloride to yield XVI-B.

Nucleophilic substitution reaction with primary or secondary amines gave derivatives of general formula I-D.

Abbreviations:

$CH_2Cl_2$=dichloromethane;

DMAP=dimethylaminopyridine;

HOBt=1-hydroxy-benzotriazol hydrat;

EDC=1-(3-dimethylaminopropyl)-3-ethylcarbodiimide hydrochloride;

$Et_3N$=triethylamine;

EtOAc=ethyl acetate;

H=hexane;

RT=room temperature;

$PPh_3$=triphenylphosphine;

DBAD=di-tert-butyl azodicarboxylate

General Procedure I

Amid Coupling (Pyrrolidine V, X or XV and Carboxylic Acid)

To a stirred solution of a carboxylic acid derivative (commercially available or known in the literature) (1 mmol) in 10 mL of $CH_2Cl_2$ was added (1.3 mmol) of EDC, (1.3 mmol) of HOBt and $Et_3N$ (1.3 mmol). After one hour at RT, was added a pyrrolidine intermediate of general formula (XII). The mixture was stirred at RT overnight and then poured onto water and extracted with $CH_2Cl_2$. The combined organic phases were dried over $Na_2SO_4$ and concentrated under vacuo. Flash chromatography or preparative HPLC afforded the title compound.

General Procedure II

Coupling Between a Compound of Formula V, X or XV and an Acid Chloride or Carbamoyl Chloride A solution of the pyrrolidine (1 mmol) of formula (V, X, XV) in $CH_2Cl_2$ (10 mL) was treated with $Et_3N$ (1.2 mmol) and an acid chloride or carbamoyl chloride (1.2 mmol) and stirred at RT overnight. The reaction mixture was then poured onto water and extracted with $CH_2Cl_2$. The combined organic phases were dried over $Na_2SO_4$ and concentrated under vacuo. Purification by preparative HPLC yielded the title compound.

General Procedure III

Mitsunobu Reaction $PPh_3$ bound on resin (2.2 mmol) was put in suspension in THF (50 mL). Then the DBAD (1.6 mmol) and the phenol, pyridin-ol or pyrimidin-ol (1.5 mmol) were added. After 5 min at RT, the alcohol of formula VII, XII or XIII was added and stirring was continued at RT overnight. The reaction mixture was filtered on celite and then concentrated under vacuo. The crude was dissolved in EtOAc, washed with aq. NaOH (1M) and the organic phase was dried over $Na_2SO_4$. Column chromatography or preparative HPLC yielded the title compound.

General Procedure IV

Nucleophilic Substitution Reaction: Coupling of XVI-B and an Primary or Secondary Amine ($NR^4R^5$)

To a stirred solution of the bromide intermediate XVI-B (1 mmol) in $CH_2Cl_2$ (20 mL) at RT were added the amine of formula $NR^4R^5$ (3 mmol) and $Et_3N$ (4 mmol). Stirring was continued overnight. The reaction mixture was washed $H_2O$ and the organic phase was dried over $Na_2SO_4$. Column chromatography or preparative HPLC yielded the title compound.

The salt formation is effected at room temperature in accordance with methods which are known per se and which are familiar to any person skilled in the art. Not only sat with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

As mentioned earlier, the compounds of formula I and their pharmaceutically usable addition salts possess valuable pharmacological properties. The compounds of the present invention are antagonists of neurokinin 3 (NK-3) receptors. The compounds were investigated in accordance with the tests given hereinafter.

[$^3$H]SR142801 Competition Binding Assay hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM MnCl$_2$, 1 µM phosphoramidon, 0.1% BSA binding buffer at pH 7.4 to a final assay concentration of 5 µg protein/well. For inhibition experiments, membranes were incubated with [$^3$H] SR142801 at a concentration equal to K$_D$ value of radioligand and 10 concentrations of the inhibitory compound (0.0003-10 µM) (in a total reaction volume of 500 µl) for 75 min at room temperature (RT). At the end of the incubation, membranes were filtered onto unit filter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 µM SB222200 for both radioligands. The radioactivity on the filter was counted (5 min) on a Packard Top-count microplate scintillation counter with quenching correction after addition of 45 µl of microscint 40 (Canberra Packard S. A., Zürich, Switzerland) and shaking for 1 h. Inhibition curves were fitted according to the Hill equation: $y=100/(1+(x/IC_{50})^{nH})$, where $n_H$=slope factor using Excel-fit 4 software (Microsoft). IC$_{50}$ values were derived from the inhibition curve and the affinity constant (K$_i$) values were calculated using the Cheng-Prussoff equation $K_i=IC_{50}/(1+[L]/K_D)$ where [L] is the concentration of radioligand and K$_D$ is its dissociation constant at the receptor, derived from the saturation isotherm. All experiments were performed in duplicate and the mean±standard error (SEM) of the individual K$_i$ values was calculated.

The results of some representative compounds of the hNK-3 receptor affinity are shown in the following Table 1.

TABLE 1

| Example No. | K$_i$ NK3 h (µM) |
|---|---|
| 16 | 0.0288 |
| 17 | 0.0468 |
| 18 | 0.0779 |
| 20 | 0.0595 |
| 24 | 0.0589 |
| 25 | 0.0597 |
| 27 | 0.0096 |
| 30 | 0.0796 |
| 31 | 0.0589 |
| 33 | 0.0756 |
| 34 | 0.0401 |

TABLE 1-continued

| Example No. | K$_i$ NK3 h (µM) |
|---|---|
| 36 | 0.0211 |
| 39 | 0.0029 |
| 41 | 0.049 |
| 42 | 0.0699 |
| 45 | 0.0954 |
| 46 | 0.0497 |
| 48 | 0.068 |
| 51 | 0.0237 |
| 52 | 0.0425 |
| 53 | 0.0068 |
| 54 | 0.002 |
| 55 | 0.02 |
| 56 | 0.0026 |
| 57 | 0.0647 |
| 59 | 0.0126 |
| 61 | 0.039 |
| 62 | 0.024 |
| 63 | 0.012 |
| 64 | 0.019 |
| 65 | 0.02 |
| 66 | 0.011 |
| 67 | 0.053 |
| 68 | 0.027 |
| 69 | 0.0056 |
| 70 | 0.086 |
| 71 | 0.0087 |
| 73 | 0.093 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the inventions contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatin capsules, solutions, emulsions, or suspensions. The pharmaceutical compositions also can be administered rectally, for example, in the form of suppositories, or parenterally, for example, in the form of injectable solutions.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

Example A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch firstly can be mixed in a mixer and then in a comminuting machine. The mixture can be returned to the mixer, the talc added thereto and mixed thoroughly. The mixture can be filled by machine into hard gelatin capsules.

Example C

Suppositories of the following composition are manufactured:

|  | mg/supp. |
| --- | --- |
| Active substance | 15 |
| Suppository mass | 1285 |
| Total | 1300 |

The suppository mass can be melted in a glass or steel vessel, mixed thoroughly and cooled to 45° C. Thereupon, the finely powdered active substance can be added thereto and stirred until it has dispersed completely. The mixture can be poured into suppository moulds of suitable size and left to cool. The suppositories then can be removed from the moulds and packed individually in wax paper or metal foil.

Description of Pyrrolidine Intermediates Formula VII, XII-A, XII-B, XV-B, XVI-B

Pyrrolidine Intermediates of Formula VII

Pyrroline VII-1

[(3RS,4SR)-3-(3,4-Dichloro-phenyl)-4-hydroxymethyl-pyrrolidin-1-yl]-(4-methanesulfonyl-piperazin-1-yl)-methanone

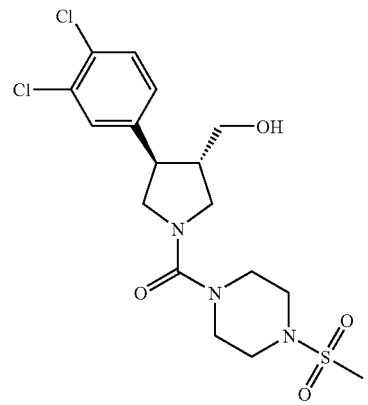

VII-1 a) (3SR,4RS)-1-Benzyl-4-(3,4-dichloro-phenyl)-pyrrolidine-3-carboxylic acid ethyl ester A solution of N-(methoxymethyl)-N-(phenylmethyl)-N-(trimethylsilyl)methylamine (2.46 g, 10.4 mmol) in $CH_2Cl_2$ (15 mL) was added dropwise, over a 30 minutes period, to a stirred solution of (E)-3-(3,4-dichloro-phenyl)-acrylic acid ethyl ester (2.40 g, 10.4 mmol) and trifluoroacetic acid (0.08 mL, 1 mmol) in $CH_2Cl_2$ (10 mL) at 0° C. The ice bath was removed, and the solution was stirred at 25° C. for an additional 48 h. It was then concentrated and purification by flash chromatography ($SiO_2$, EtOAc/H 1:4) afforded 2.48 g (66%) of the title compound as a yellow oil. ES-MS m/e: 379.3 (M+H$^+$).

b) (3SR,4RS)-4-(3,4-Dichloro-phenyl)-pyrrolidine-3-carboxylic acid ethyl ester

To a solution of (3SR,4RS)-1-benzyl-4-(3,4-dichloro-phenyl)-pyrrolidine-3-carboxylic acid ethyl ester 2.50 g (6.61 mmol) dissolved in $CH_3CN$ (55 mL) was added 1.34 mL (9.91 mmol) of 2,2,2-trichloroethyl chloroformate and stirring was continued for 4 hours at RT. Volatiles were removed under vacuo, and the residue was dissolved in AcOH (25 mL) before a total of 1.20 g of Zn dust was added portion wise. After three hours at RT, the reaction mixture was filtered on celite, the solvent removed under vacuo, followed by an extraction with EtOAc/aq. $NaHCO_3$ (basic pH). The organic phases were dried on $Na_2SO_4$ and column chromatography ($SiO_2$, $CH_2Cl_2$/MeOH 9:1) yielded 1.85 g (97%) of the title compound as a light yellow oil. ES-MS m/e: 288.1 (M+H$^+$).

c) (3SR,4RS)-4-(3,4-Dichloro-phenyl)-1-(4-methanesulfonyl-piperazine-1-carbonyl)-pyrrolidine-3-carboxylic acid ethyl ester Using the general procedure II, the coupling between (3SR,4RS)-4-(3,4-Dichloro-phenyl)-pyrrolidine-3-carboxylic acid ethyl ester (1.89 g, 6.55 mmol) and 4-methanesulfonyl-piperazine-1-carbonyl chloride (1.63 g, 7.2 mmol) yielded the title product (2.40 g, 77%) as a colorless oil after purification by flash chromatography (SiO$_2$, EtOAc). ES-MS m/e: 478.1 (M+H$^+$).

4-Methanesulfonyl-piperazine-1-carbonyl chloride

To a stirred solution of carbonic acid ditrichloromethyl ester (triphosgene) (1.81 g, 6.09 mmol) in CH$_2$Cl$_2$ (30 mL) at 0° C., was added a solution of 1-methanesulfonyl-piperazine (2.0 g, 12.2 mmol) and pyridine (1.08 mL) 13.4 mmol) in CH$_2$Cl$_2$ (5 mL) over 30 minutes. The temperature was raised to RT, and stirring was continued over night. The organic phase was washed with H$_2$O, dried over Na$_2$SO$_4$. Purification by flash chromatography (SiO$_2$, EtOAc) yielded 2.20 g (79%) of the title compound as white solid.

d) [(3RS,4 SR)-3-(3,4-Dichloro-phenyl-4-hydroxymethyl-pyrrolidin-1-yl]-(4-methanesulfonyl-piperazin-1-yl)-methanone To a stirred solution of (3SR,4RS)-4-(3,4-Dichloro-phenyl)-1-(4-methanesulfonyl-piperazine-1-carbonyl)-pyrrolidine-3-carboxylic acid ethyl ester (2.39 g, 5.00 mmol) in MeOH (80 mL) at RT was added LiBH$_4$ (434 mg, 19.9 mmol). After 2 hours, addition of a second portion of LiBH$_4$ (1.30 g, 59.7 mmol) and stirring was continued for 2 days. The reaction mixture was poured on H$_2$O, extracted with EtOAc and the combined organic phases were dried over Na$_2$SO$_4$. Flash chromatography (SiO$_2$, EtOAc, then EtOAc/MeOH 9:1) yielded the title product 1.76 g (81%) as a white solid. ES-MS m/e: 436.1 (M+H$^+$).

Pyrrolidine Intermediates of Formula XII

Pyrrolidine XII-A-1 and XII-B-1

[(3RS,4SR)-3-(3,4-Dichloro-phenyl)-4-((RS)-1-hydroxy-ethyl)-pyrrolidin-1-yl]-(4-methanesulfonyl-piperazin-1-yl)-methanone (XII-A-1)

and

[(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1)

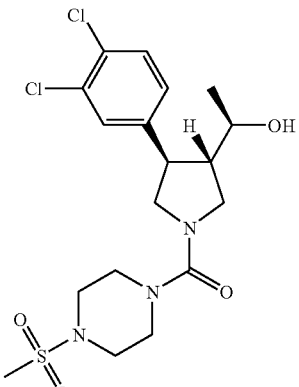

XII-A-1

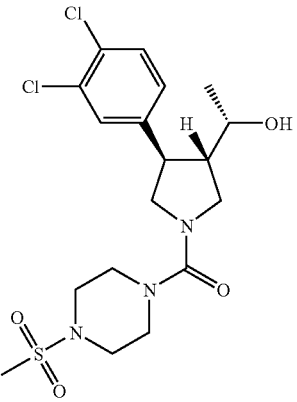

XII-B-1 a) 1-[(3SR,4RS-1-Benzyl-4-(3,4-dichloro-phenyl)-pyrrolidin-3-yl]-ethanone (IX-1)

A solution of N (methoxymethyl)-N-(phenylmethyl)-N-(trimethylsilyl)methylamine (32.78 g, 0.138 mol) in CH$_2$Cl$_2$ (50 mL) was added drop wise, over a 30 minutes period, to a stirred solution of (E)-4-(3,4-dichloro-phenyl)-but-3-en-2-one (19.80 g, 0.092 mol) and trifluoroacetic acid (1.05 mL, 0.009 mol) in CH$_2$Cl$_2$ (100 mL) at 0° C. The ice bath was removed, and the solution was stirred at 25° C. for an additional 48 h. It was then concentrated and purification by flash chromatography (SiO$_2$, CH$_2$Cl$_2$/MeOH 98:2) afforded 28.3 g (88%) of the title compound as a yellow oil. ES-MS m/e: 348.2 (M+H$^+$).

b) 1-[(3SR,4RS)-4-(3,4-Dichloro-phenyl)-pyrrolidin 3-yl]-ethanone (X-1)

To a solution of 1-[(3SR,4RS)-1-benzyl-4-(3,4-dichloro-phenyl)-pyrrolidin-3-yl]-ethanone 4.00 g (9.20 mmol) dissolved in CH$_3$CN (50 mL) was added 2.48 mL (18.40 mmol) of 2,2,2-trichloroethyl chloroformate and stirring was continued for 3 hours at RT. Volatiles were removed under vacuo, and the residue was dissolved in AcOH (30 mL) before a total of 1.5 g of Zn dust was added portion wise. After three hours at RT, the reaction mixture was filtered on celite, the solvent removed under vacuo, followed by extraction with EtOAc/aq. NaHCO$_3$ (basic pH). The organic phases were dried on Na$_2$SO$_4$ and column chromatography (SiO$_2$, CH$_2$Cl$_2$/MeOH 9:1 to 8:2) yielded 1.50 g (63%) of the title compound as a colorless oil. ES-MS m/e: 258.0 (M+H$^+$).

c) 1-[(3SR,4RS)-4-(3,4-Dichloro-phenyl)-1-(4-methanesulfonyl-piperazine-1-carbonyl)-pyrrolidin-3-yl]-ethanone (XI-1)

Using the general procedure II, the coupling between 1-[(3SR,4RS)-4-(3,4-dichloro-phenyl)-pyrrolidin-3-yl]-ethanone (1.88 g, 7.28 mmol) and 4-methanesulfonyl-piperazine-1-carbonyl chloride (1.98 g, 8.74 mmol) yielded the title product (2.40 g, 74%) as a colorless oil after purification by flash chromatography (SiO$_2$, EtOAc).

d) [(3RS,4SR)-3-(3,4-Dichloro-phenyl)-4-((RS)-1-hydroxy-ethyl)-pyrrolidin-1-yl]-(4-methanesulfonyl-piperazin-1-yl)-methanone (XII-A-1) and (3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1)

To a stirred solution of 1-[(3SR,4RS)-4-(3,4-dichloro-phenyl)-1-(4-methanesulfonyl-piperazine-1-carbonyl)-pyrrolidin-3-yl]-ethanone (XI-1) (2.00 g, 4.46 mmol) in MeOH (40 mL) at −78° C. was added LiBH$_4$ (0.13 g, 4.68 mmol). The temperature was slowly raised to RT (over 1 hour), and the reaction mixture was quenched by addition of H$_2$O. The product was extracted with EtOAc, the combined organic phases were dried over Na$_2$SO$_4$. The two diastereoisomers were separated by column chromatography (SiO$_2$) to yield 0.31 g (16%) of [(3RS,4SR)-3-(3,4-dichloro-phenyl)-4-((RS)-1 hydroxy-ethyl)-pyrrolidin-1-yl]-(4-methanesulfonyl-piperazin-1-yl)-methanone (XII-A-1) as a white solid ES-MS m/e: 450.1 (M+Ht) and 1.02 g (51%) of [(3RS,4SR)-3-(3,4-dichloro-phenyl)-4-((SR)-1-hydroxy-ethyl)-pyrrolidin-1-yl]-(4 methanesulfonyl-piperazin-1-yl)-methanone (XII-1-B-1) as a white solid ES-MS m/e: 450.1 (M+H$^+$).

Pyrrolidine Intermediates of Formula XV

Pyrrolidine XV-B-1

(3RS,4SR)-3-(3,4-Dichloro-phenyl)-4-[(RS)-1-(4-trifluoromethyl-phenoxy)-ethyl]-pyrrolidine

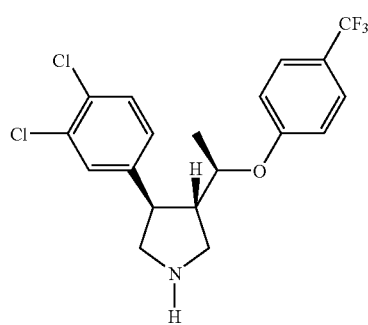

XV-B-1 a) (RS)-1-[(3SR,4RS)-4-(3,4-Dichloro-phenyl)-pyrrolidin-3-yl]-ethanol (XIII-A-1) and (SR)-1-[(3SR,4RS)-4-(3,4-Dichloro-phenyl)-pyrrolidin-3-yl]-ethanol (XIII-B-1)

To a solution of 1-[(3SR,4RS) 1-benzyl-4-(3,4-dichloro-phenyl)-pyrrolidin-3-yl]-ethanone (IX-1) (14.90 g, 0.043 mol) in THF (300 mL) at 0° C. were added portionwise LiAlH$_4$ (2.05 g 0.051 mol). Stirring was continued for one hour, and the reaction mixture was carefully quenched by addition of aq. NH$_4$Cl, concentrated under vacuo and the product extracted with EtOAC. The combined organic phases were dried on Na$_2$SO$_4$ and concentrated under vacuo. The two diastereoisomeres were separated by column chromatography (SiO$_2$, EtOAc/H, 1:1) to yield (SR)-1-[(3SR,4RS)-1-benzyl-4-(3,4-dichloro-phenyl)-pyrrolidin-3-yl]-ethanol (XIII-B-1) 4.69 g (31%) as a white solid ES-MS m/e: 350.2 (M+H$^+$) and (RS)-1-[(3SR,4RS)-1-benzyl-4-(3,4-dichloro-phenyl)-pyrrolidin-3-yl]-ethanol (XIII-A-1) 5.30 g (35%) as a white solid ES-MS m/e: 350.2 (M+H$^+$).

b) (3RS,4SR)-1-Benzyl-3-(3,4-dichloro-phenyl-4-[(RS)-1-(4-trifluoromethyl-ethyl]-pyrrolidine (XIV-B-1)

To a suspension of PPh$_3$ (PPh$_3$ polymer bound, 3 mmol PPh$_3$/g resin) (1.80 g, 5.59 mmol) in THF (40 mL) at 0° C. were added 4-trifluoromethyl-phenol (0.618 g, 3.81 mmol) and then DBAD (0.936 g, 4.07 mmol). After 5 minutes was added (SR)-1-[(3SR,4RS)-1-benzyl-4-(3,4-dichloro-phenyl)-pyrrolidin-3-yl]-ethanol (XIII-B-1) (0.89 g, 2.54 mol). The reaction mixture was stirred over night at RT, filtered on celite and concentrated under vacuo. Extraction with EtOAc/aq.NaOH 1M, followed by column chromatography (SiO$_2$, EtOAc/H, 1:6) yielded 0.990 g (79%) of the title compound as a colorless oil. ES-MS m/e: 493.0 (M+H$^+$).

c) (3RS,4SR)-3-(3,4-Dichloro-phenyl)-4-[(RS)-1-(4-trifluoromethyl-phenoxy)-ethyl]pyrrolidine (XV-B-1)

To a solution of (3RS,4SR)-1-benzyl-3-(3,4-dichloro-phenyl)-4-[(RS)-1-(4-trifluoromethyl-phenoxy)-ethyl]-pyrrolidine (XIV-B-1) 0.99 g (2.00 mmol) dissolved in CH$_3$CN (25 mL) was added 0.40 mL (3.00 mmol) of 2,2,2-trichloroethyl chloroformate and stirring was continued for 4 hours at RT. Volatiles were removed under vacuo, and the crude was dissolved in AcOH (20 mL) before a total of 800 mg of Zn dust was added portion wise. After three hours at RT, the reaction mixture was filtered on celite, the solvent removed under vacuo, followed by an extraction with EtOAc/aq. NaHCO$_3$ (basic pH). The organic phases were dried on Na$_2$SO$_4$ and column chromatography (SiO$_2$, CH$_2$Cl$_2$/MeOH 9:1) yielded 0.54 g (67%) of the title compound as a colorless oil. ES-MS m/e: 404.2 (M+H$^+$).

Pyrrolidine XV-B-2

5-Chloro-2-{(RS)-1-[(3SR,4RS)-4-(3,4-dichloro-phenyl)-pyrrolidin-3-yl]-ethoxy}-pyridine

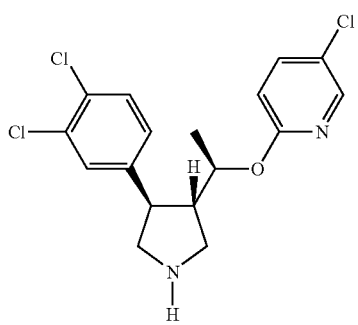

XV-B-2

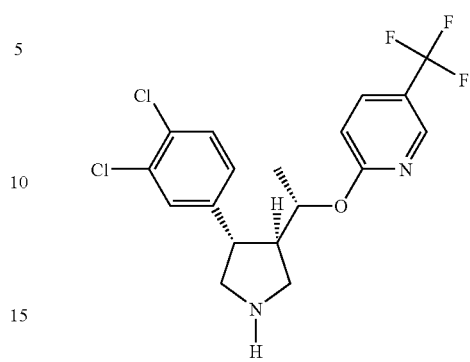

XV-B-3 a) 2-{(RS)-1-(3SR,4RS)-1-Benzyl-4-(3,4-dichloro-phenyl)-pyrrolidin-3-yl}-ethoxy-5-chloro-pyridine (XIV-B-2)

To a suspension of PPh$_3$ (PPh$_3$ polymer bound, 3 mmol PPh$_3$/g resin) (3.05 g, 9.17 mmol) in THF (50 mL) at 0° C. were added 5-chloro-pyridin-2-ol (0.81 g, 6.25 mmol) and then DBAD (1.53 g, 6.67 mmol). After 5 minutes was added (SR)-1-[(3SR,4RS)-1-benzyl-4-(3,4-dichloro-phenyl)-pyrrolidin-3-yl]-ethanol (XIII-B-1) (1.46 g, 4.17 mmol). The reaction mixture was stirred over night at RT, filtered on celite and concentrated under vacuo. Extraction with EtOAc/aq.NaOH 1M, followed by column chromatography (SiO$_2$, EtOAc/H, 1:6) yielded 1.57 g (82%) of the title compound as a colorless oil. ES-MS m/e: 461.2 (M+H$^+$).

c) 5-Chloro-2-{(RS)-1-[(3SR,4RS)-4-(3,4-dichloro-phenyl)-pyrrolidin-3-yl]-ethoxy}-pyridine (XV-B-2)

To a solution of 2-{(RS)-1-[(3SR,4RS)-1-benzyl-4-(3,4-dichloro-phenyl)-pyrrolidin-3-yl]-ethoxy}-5-chloro-pyridine (XIV-B-2) 1.57 g (3.40 mmol) dissolved in CH$_3$CN (40 mL) was added 1.08 mL (5.10 mmol) of 2,2,2-trichloroethyl chloroformate and stirring was continued for 3 hours at RT. Volatiles were removed under vacuo, and the residue was dissolved in AcOH (30 mL) before a total of 1.20 g of Zn dust was added portion wise. After three hours at RT, the reaction mixture was filtered on celite, the solvent removed under vacuo, followed by an extraction with EtOAc/aq. NaHCO$_3$ (basic pH). The organic phases were dried on Na$_2$SO$_4$ and column chromatography (SiO$_2$, CH$_2$Cl$_2$/MeOH 9:1) yielded 0.54 g (67%) of the title compound as a colorless oil. ES-MS m/e: 356.3 (M+H$^+$).

Pyrrolidine XV-B-3

2-{(SR)-1-[(3RS,4SR)-4-(3,4-Dichloro-phenyl)-pyrrolidin-3-yl]-ethoxy}-5-trifluoromethyl-pyridine a) 2-{(SR)-1-[(3RS,4SR)-1-Benzyl-4-(3,4-dichloro-phenyl)-pyrrolidin-3-yl]-ethoxy}-5-trifluoromethyl-pyridine (XIV-B-3)

To a suspension of PPh$_3$ (PPh$_3$ polymer bound, 3 mmol PPh$_3$/g resin) (0.77 g) in THF (25 mL) at 0° C. were added 5-trifluoromethyl-pyridin-2-ol (0.28 g, 1.75 mmol) and then DBAD (0.43 g). After 5 minutes was added (RS)-1-[(3RS,4SR)-1-benzyl-4-(3,4-dichloro-phenyl)-pyrrolidin-3-yl]-ethanol (0.41 g, 1.17 mmol, described herein above). The reaction mixture was stirred over night at RT, filtered on celite and concentrated under vacuo. Extraction with EtOAc/aq.NaOH 1M, followed by column chromatography (SiO$_2$, EtOAc/H, 1:4) yielded 0.45 g (78%) of the title compound as a colorless oil. ES-MS m/e: 495.8 (M+H$^+$).

b) 2-{(SR)-1-[(3RS,4SR)-4-3,4-Dichloro-phenyl)-pyrrolidin-3-yl]-ethoxy}-5-trifluoromethyl-pyridine (XV-B-3)

To a solution of 2-{(SR)-1-[(3RS,4SR)-1-benzyl-4-(3,4-dichloro-phenyl)-pyrrolidin-3-yl]-ethoxy}-5-trifluorom-ethyl-pyridine 0.45 g (0.91 mmol) dissolved in toluene (5 mL) were added 0.30 mL (2.7 mmol) of 1-chloroethyl chloroformate and 0.46 mL of Hunig's base. The reaction mixture was heated at 100° C. for one hour. After cooling down to RT, volatiles were removed under vacuo and the crude was dissolved in MeOH (5 mL). The reaction mixture was heated at 85° C. for 30 minutes and after cooling down to RT, volatiles were removed under vacuo and the residue was directly purified on column chromatography (SiO$_2$, CH$_2$CO$_2$/MeOH 9:1) yielded 0.32 g (87%) of the title compound as a light yellow oil. ES-MS m/e: 405.9 (M+H$^+$).

Pyrrolidine XV-B-4

6-{(SR)-1-[(3RS,4SR)-4-(3,4-Dichloro-phenyl)-pyrrolidin-3-yl]-ethoxy}-nicotinonitrile

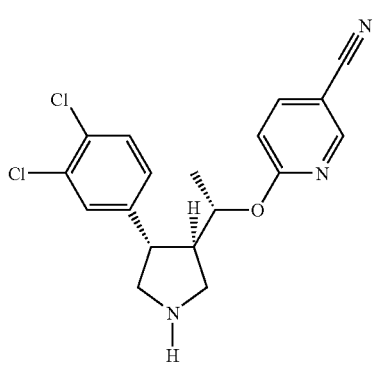

XV-B-4

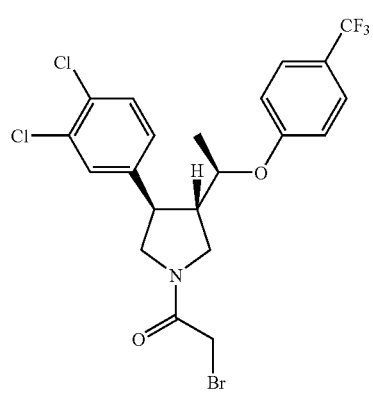

XVI-B-1 a) 6-{(SR)-1-[(3RS,4SR)-1-Benzyl-4-(3,4-dichloro-phenyl)-pyrrolidin-3-yl]-ethoxy}-nicotinonitrile (XVI-B-4)

To a suspension of PPh₃ (PPh₃ polymer bound, 3 mmol PPh₃/g resin) (1.97 g) in THF (300 mL) at 0° C. were added 6-hydroxy-nicotinonitrile (0.61 g, 5.1 mmol) and then DBAD (1.10 g). After 5 minutes was added (RS)-1-[(3RS,4SR)-1-benzyl-4-(3,4-dichloro-phenyl)-pyrrolidin-3-yl]-ethanol (1.20 g, 3.4 mmol, described herein above). The reaction mixture was stirred over night at RT, filtered on celite and concentrated under vacuo. Extraction with EtOAc/aq.NaOH 1M, followed by column chromatography (SiO₂, EtOAc/H, 1:4) yielded 1.02 g (66%) of the title compound as a colorless oil. ES-MS m/e: 452.0 (M+H⁺).

b) 6-{(SR)-1-[(3RS,4SR)-4-(3,4-Dichloro-phenyl)-pyrrolidin-3-yl]-ethoxy}-nicotinonitrile (XV-B-4)

To a solution of 6-{(SR)-1-[(3RS,4SR)-1-benzyl-4-(3,4-dichloro-phenyl)-pyrrolidin-3-yl]-ethoxy}-nicotinonitrile 0.75 g (1.70 mmol) dissolved in CH₃CN (50 mL) was added 0.56 mL (4.14 mmol) of 2,2,2-trichloroethyl chloroformate and stirring was continued for 4 hours at RT. Volatiles were removed under vacuo) and the crude was dissolved in AcOH (30 mL) before a total of 0.45 g of Zn dust was added portion wise. After three hours at RT, the reaction mixture was filtered on celite, the solvent removed under vacuo, followed by an extraction with EtOAc/aq. NaHCO₃ (basic pH). The organic phases were dried on Na₂SO₄ and column chromatography (SiO₂, CH₂Cl₂/MeOH 9:1) yielded 0.36 g (60%) of the title compound as a colorless oil. ES-MS m/e: 362.3 (M+H⁺).

Pyrrolidine Intermediates of Formula XVI

Pyrrolidine XVI-B-1

2-Bromo-1-{(3RS,4SR)-3-(3,4-dichloro-phenyl)-4-[(RS)-1-(4-trifluoromethyl-phenoxy)-ethyl]-pyrrolidin-1-yl}-ethanone To a stirred solution of (3RS,4SR)-3-(3,4-dichloro-phenyl)-4-[(RS)-1-(4-trifluoromethyl-phenoxy)-ethyl]-pyrrolidine (XV-B-1) 0.25 g (0.62 mmol) in CH₂Cl₂ (30 mL) at RT, 0.10 ml (0.74 mmol) of Et₃N and 0.062 mL (0.74 mmol) of bromo-acetyl chloride were added. Stirring was continued over night and then concentrated under vacuo. The crude residue was dissolved in EtOAc, washed with H₂O. The organic phase was dried over Na₂SO₄ and the product was purified by flash chromatography (SiO₂, EtOAc) to yield the title product 0.275 g (85%) as a colorless oil.

Pyrrolidine XVI-B-2

2-Bromo-1-[(3SR,4RS)-3-[(RS)-1 (5-chloro-pyridin-2-yloxy)-ethyl]-4-(3,4-dichloro-phenyl)-pyrrolidin-1-yl]-ethanone

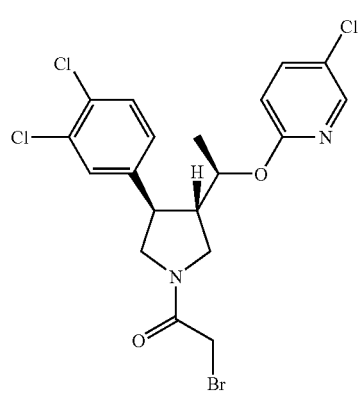

XVI-B-2

To a stirred solution of 5-chloro-2-{(RS)-1-[(3SR,4RS)-4-(3,4-dichloro-phenyl)-pyrrolidin-3-yl]-ethoxy}-pyridine (XV-B-2) 0.12 g (0.32 mmol) in CH₂Cl₂ (10 mL) at RT, 0.055 ml (0.38 mmol) of Et₃N and 0.032 mL (0.33 mmol) of bromo-acetyl chloride were added. Stirring was continued over night and then concentrated under vacuo. The crude residue was dissolved in EtOAc, washed with H₂O. The organic phase Pyrrolidine XVI-B-4

6-{(SR)-1-[(3RS,4SR)-1-(2-Bromo-acetyl)-4-(3,4-dichloro-phenyl)-pyrrolidin-3-yl]-ethoxy}-nicotinonitrile

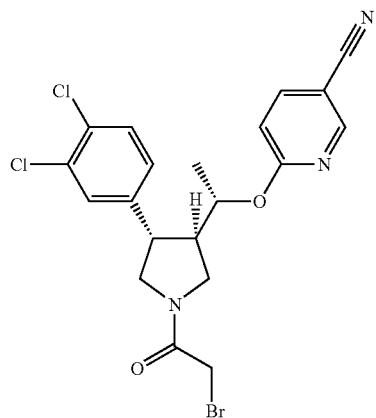

XVI-B-4

To a stirred solution of 6-{(SR)-1-[(3RS,4SR)-4-(3,4-Dichloro-phenyl)-pyrrolidin-3-yl]-ethoxy}-nicotinonitrile (XV-B-4) 30 mg (0.083 mmol) in CH$_2$Cl$_2$ (3 mL) at RT, 0.013 ml (0.01 mmol) of Et$_3$N and 0.0083 mL (0.01 mmol) of bromo-acetyl chloride were added. Stirring was continued over night and then concentrated under vacuo. The crude residue was dissolved in EtOAc, washed with H$_2$O. The organic phase was dried over Na$_2$SO$_4$ and the product was purified by flash chromatography (SiO$_2$, EtOAc) to yield the title product 34 mg (85%) as a colorless oil.

Example 1

[(3SR,4RS)-3-(4-Chloro-phenoxymethyl)-4-(3,4-dichloro-phenyl)-pyrrolidin-1-yl]-(4-methanesulfonyl-piperazin-1-yl)-methanone

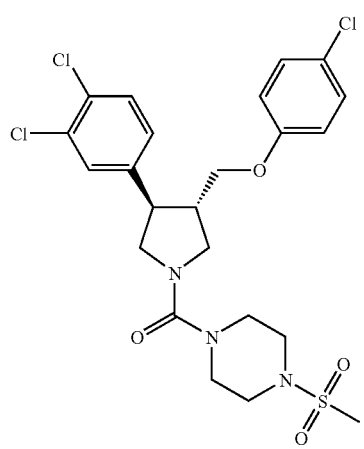

Mitsunobu Reaction According to General Procedure III:

Pyrrolidine intermediate: [(3RS,4SR)-3-(3,4-Dichloro-phenyl)-4-hydroxyethyl-pyrrolidin-1-yl]-(4-methanesulfonyl-piperazin-1-yl)-methanone (VII-1), Phenol: 4-Chloro-phenol (commercially available), ES-MS m/e: 545.7 (M+H$^+$).

Example 2

[(3RS,4SR)-3-(3,4-Dichloro-phenyl)-4-(4-trifluoromethyl-phenoxyethyl)-pyrrolidin-1-yl]-(4-methanesulfonyl-piperazin-1-yl)-methanone

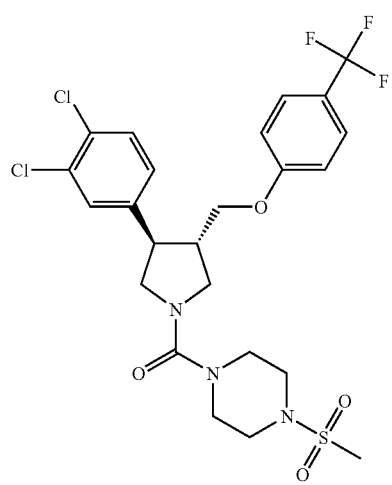

Mitsunobu Reaction According to General Procedure III:

Pyrrolidine intermediate: [(3RS,4SR)-3 (3,4-Dichloro-phenyl)-4-hydroxymethyl-pyrrolidin-1-yl]-(4-methanesulfonyl-piperazin-1-yl)-methanone (VII-1), Phenol: 4-Trifluoromethyl-phenol (commercially available), ES-MS m/e: 581.0 (M+H$^+$).

Example 3

[(3SR,4RS)-3-(2-Chloro-4-trifluoromethyl-phenoxymethyl)-4-(3,4-dichloro-phenyl)-pyrrolidin-1-yl]-(4-methanesulfonyl-piperazin-1-yl)-methanone

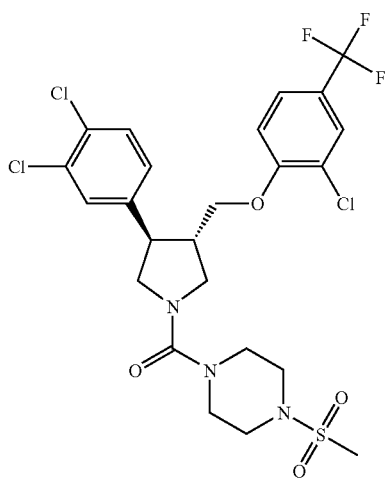

Mitsunobu Reaction According to General Procedure III:
Pyrrolidine intermediate: [(3RS,4SR)-3-(3,4-Dichloro-phenyl)-4-hydroxymethyl-pyrrolidin-1-yl]-(4-methane-sulfonyl-piperazin-1-yl)-methanone (VII-1),
Phenol: 2-Chloro-4-trifluoromethyl-phenol (commercially available),
ES-MS m/e: 616.0 (M+H$^+$).

Example 4

[(3SR,4RS)-3-(2-Chloro-3-trifluoromethyl-phenoxymethyl) 4-(3,4-dichloro-phenyl)-pyrrolidin-1-yl]-(4-methanesulfonyl-piperazin-1-yl)-methanone

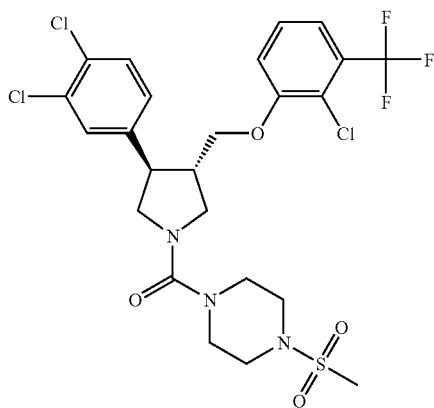

Mitsunobu Reaction According to General Procedure III:
Pyrrolidine intermediate: [(3RS,4SR)-3-(3,4-Dichloro-phenyl)-4-hydroxymethyl-pyrrolidin-1-yl]-(4-methane-sulfonyl-piperazin-1-yl)-methanone (VII-1),
Phenol: 2-Chloro-3-trifluoromethyl-phenol (commercially available),
ES-MS m/e: 616.0 (M+H$^+$).

Example 5

[(3RS,4SR)-3-(3,4-Dichloro-phenyl)-4-(2-fluoro-5-trifluoromethyl-phenoxymethyl)-pyrrolidin-1-yl]-(4-methanesulfonyl-piperazin-1-yl)-methanone

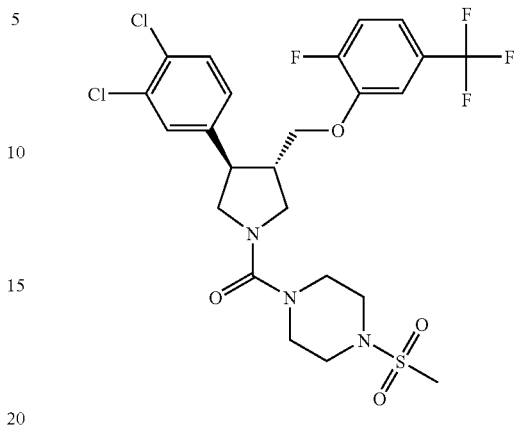

Mitsunobu Reaction According to General Procedure III:
Pyrrolidine intermediate: [(3RS,4SR)-3-(3,4-Dichloro-phenyl)-4-hydroxymethyl-pyrrolidin-1-yl]-(4-methane-sulfonyl-piperazin-1-yl)-methanone (VII-1),
Phenol: 2-Fluoro-5-trifluoromethyl-phenol (commercially available),
ES-MS m/e: 598.2 (M+4H$^+$).

Example 6

4-[(3SR,4RS)-4-(3,4-Dichloro-phenyl)-1-(4-methanesulfonyl-piperazin-1-carbonyl)-pyrrolidin-3-yl-methoxy]-benzonitrile

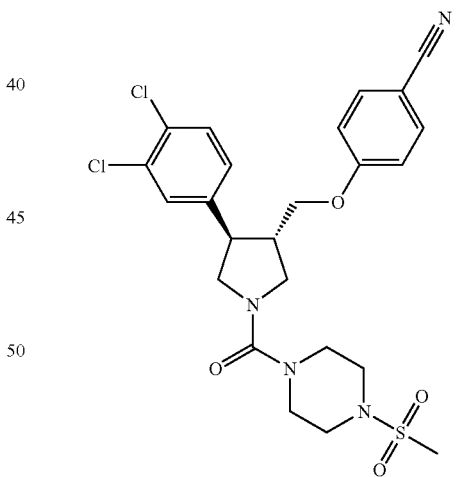

Mitsunobu Reaction According to General Procedure III:
Pyrrolidine intermediate: [(3RS,4SR)-3-(3,4-Dichloro-phenyl)-4-hydroxymethyl-pyrrolidin-1-yl]-(4-methane-sulfonyl-piperazin-1-yl)-methanone (VII-1),
Phenol: 4-Hydroxy-benzonitrile (commercially available),
ES-MS m/e: 537.2 (M+H$^+$).

Example 7

[(3RS,4SR)-3-(3,4-Dichloro-phenyl)-4-(3-trifluoromethyl-phenoxymethyl)-pyrrolidin-1-yl]-(4-methanesulfonyl-piperazin-1-yl)-methanone

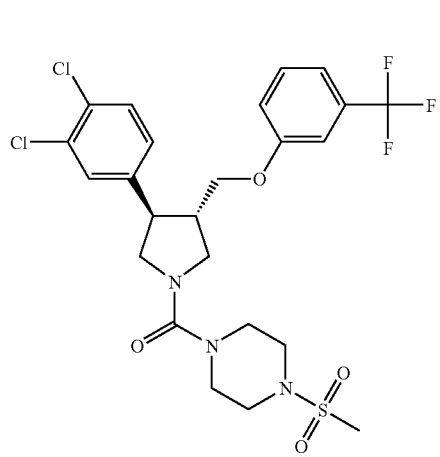

Mitsunobu Reaction According to General Procedure III:
Pyrrolidine intermediate: [(3RS,4SR)-3-(3,4-Dichloro-phenyl)-4-hydroxymethyl-pyrrolidin-1-yl]-(4-methane-sulfonyl)-piperazin-1-yl)-methanone (VII-1),
Phenol: 3-Trifluoromethyl-phenol (commercially available),
ES-MS m/e: δ 1.0 (M+H$^+$).

Example 8

[(3RS,4SR)-3-(3,4-Dichloro-phenyl)-4-p-tolyloxymethyl-pyrrolidin-1-yl]-(4-methanesulfonyl-piperazin-1-yl)-methanone

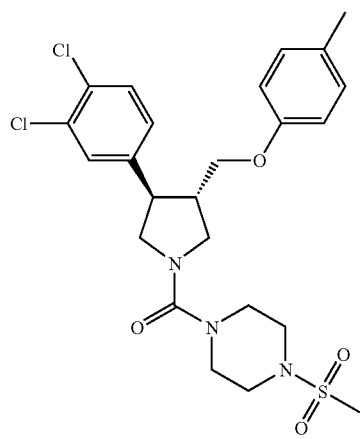

Mitsunobu Reaction According to General Procedure III:
Pyrrolidine intermediate: [(3RS,4SR)-3-(3,4-Dichloro-phenyl)-4-hydroxymethyl-pyrrolidin-1-yl]-(4-methane-sulfonyl-piperazin-1-yl)-methanone (VII-1),
Phenol: 4-Methyl-phenol (commercially available),
ES-MS m/e: 525.8 (M+H$^+$).

Example 9

[(3RS,4SR)-3-(3,4-Dichloro-phenyl)-4-(4-fluoro-phenoxymethyl)-pyrrolidin-1-yl]-(4-methanesulfonyl-piperazin-1-yl)-methanone

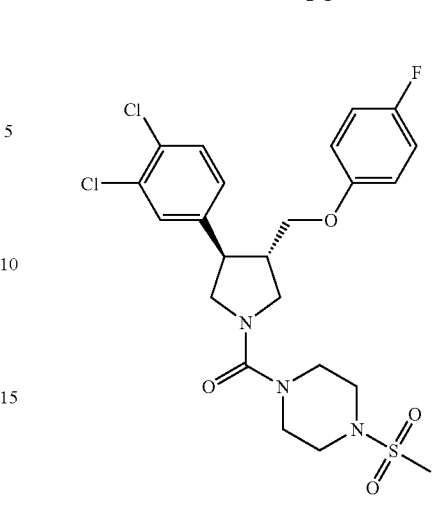

Mitsunobu Reaction According to General Procedure III:
Pyrrolidine intermediate: [(3RS,4SR)-3-(3,4-Dichloro-phenyl)-4-hydroxymethyl-pyrrolidin-1-yl]-(4-methane-sulfonyl-piperazin-1-yl)-methanone (VII-1),
Phenol: 4-Fluoro-phenol (commercially available),
ES-MS m/e: 529.7 (M+H$^+$).

Example 10

[(3RS,4SR)-3-(3,4-Dichloro-phenyl)-4-m-tolyloxymethyl-pyrrolidin-1-yl]-(4-methanesulfonyl-piperazin-1-yl)-methanone

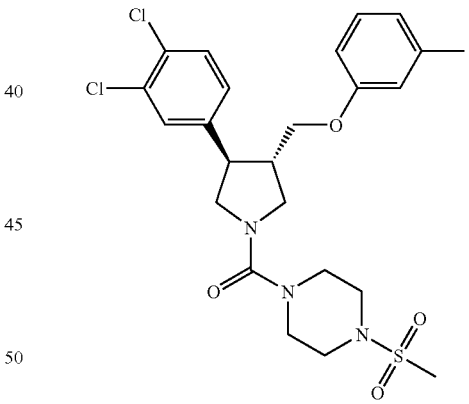

Mitsunobu Reaction According to General Procedure III:
Pyrrolidine intermediate: [(3RS,4SR)-3-(3,4-Dichloro-phenyl)-4-hydroxymethyl-pyrrolidin-1-yl]-(4-methane-sulfonyl-piperazin-1-yl)-methanone (VII-1),
Phenol: 3-Methyl-phenol (commercially available),
ES-MS m/e: 525.8 (M+H$^+$), Example 11

[(3RS,4SR)-3-(3,4-Dichloro-phenyl)-4-(3,5-dimethyl-phenoxymethyl)-pyrrolidin-1-yl]-(4-methane-sulfonyl-piperazin-1-yl)-methanone

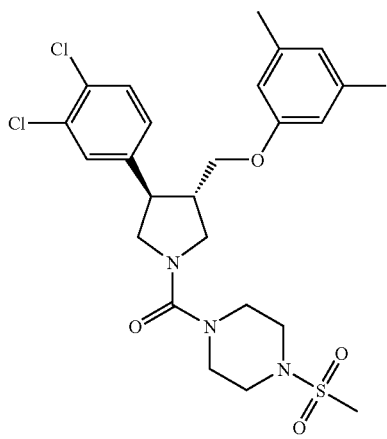

Mitsunobu Reaction According to General Procedure III:

Pyrrolidine intermediate: [(3RS,4SR)-3-(3,4-Dichloro-phenyl)-4-hydroxymethyl-pyrrolidin-1-yl]-(4-methane-sulfonyl-piperazin-1-yl)-methanone (VII-1), Phenol: 3,5-Dimethyl-phenol (commercially available), ES-MS m/e: 539.7 (M+H$^+$).

Example 12

[(3RS,4SR)-3-(3,4-Dichloro-phenyl)-4-(3-trifluoromethoxy-phenoxymethyl)-pyrrolidin-1-yl]-(4-methanesulfonyl-piperazin-1-yl)-methanone

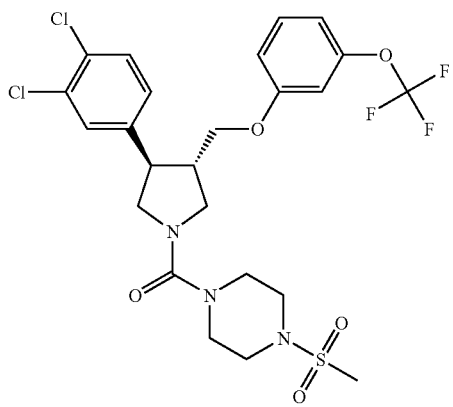

Mitsunobu Reaction According to General Procedure III:

Pyrrolidine intermediate: [(3RS,4SR)-3-(3,4-Dichloro-phenyl)-4-hydroxymethyl-pyrrolidin-1-yl]-(4-methane-sulfonyl-piperazin-1-yl)-methanone (VII-1), Phenol: 3-Trifluoromethoxy-phenol (commercially available), ES-MS m/e: 595.6 (M+H$^+$).

Example 13

[(3SR,4RS)-3-(4-Chloro-3-fluoro-phenoxymethyl)-4-(3,4-dichloro-phenyl)-pyrrolidin-1-yl]-(4-methanesulfonyl-piperazin-1-yl)-methanone

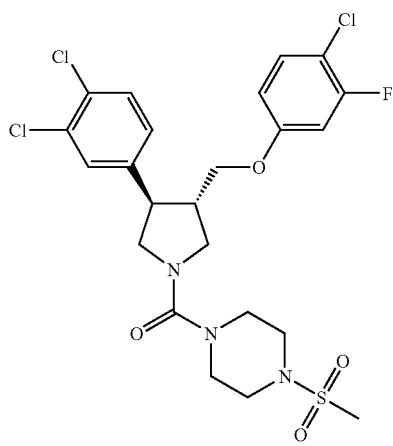

Mitsunobu Reaction According to General Procedure III:

Pyrrolidine intermediate: [(3RS,4SR)-3-(3,4-Dichloro-phenyl)-4-hydroxymethyl-pyrrolidin-1-yl]-(4-methane-sulfonyl-piperazin-1-yl)-methanone VII-1), Phenol: 4-Chloro-3-fluoro-phenol (commercially available), ES-MS m/e: 565.7 (M+H$^+$).

Example 14

[(3RS,4SR)-3-(3,4-Dichloro-phenyl)-4-(4-imidazol-1-yl-phenoxymethyl)-pyrrolidin-1 yl]-(4-methanesulfonyl-piperazin-1-yl)-methanone

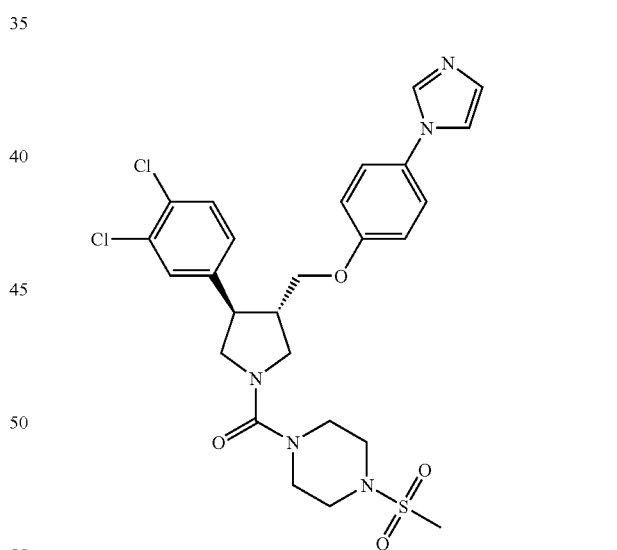

Mitsunobu Reaction According to General Procedure III:

Pyrrolidine intermediate: [(3RS,4SR)-3-(3,4-Dichloro-phenyl)-4-hydroxymethyl-pyrrolidin-1-yl]-(4-methane-sulfonyl-piperazin-1-yl)-methanone (VII-1), Phenol: 4-Imidazol-1-yl-phenol (commercially available), ES-MS m/e: 577.6 (M+H$^+$).

Example 15

[(3RS,4SR)-3-(3,4-Dichloro-phenyl)-4-(4-trifluoromethoxy-phenoxymethyl)-pyrrolidin-1-yl]-(4- methanesulfonyl-piperazin-1-yl)-methanone

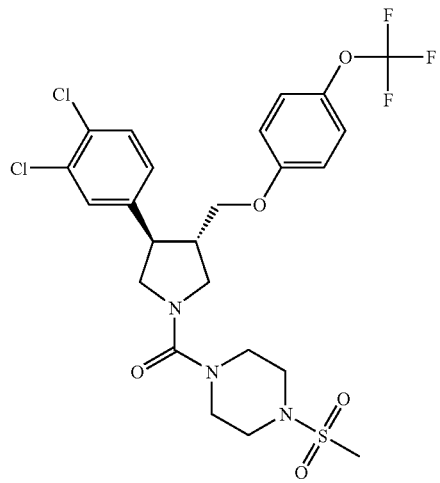

Mitsunobu Reaction According to General Procedure III:

Pyrrolidine intermediate: [(3RS,4SR)-3-(3,4-Dichloro-phenyl)-4-hydroxymethyl-pyrolidin-1-yl]-(4-methanesulfonyl-piperazin-1-yl)-methanone (VII-1), Phenol: 4-Trifluoromethoxy-phenol (commercially available), ES-MS m/e: 595.6 (M+H$^+$).

Example 16

{(3RS,4SR)-3-(3,4-Dichloro-phenyl)-4-[(RS)-1-(4-trifluoromethyl-phenoxy)-ethyl]-pyrrolidin-1-yl}-(4-methanesulfonyl-piperazin-1-yl)-methanone

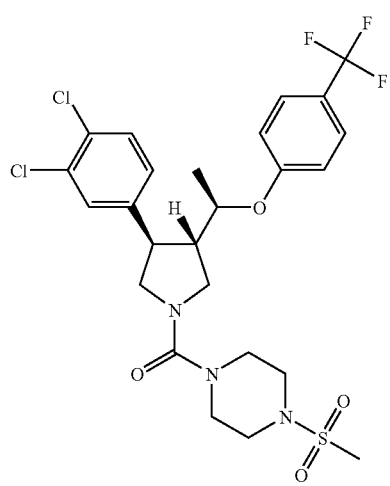

Mitsunobu Reaction According to General Procedure III:

Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1), Phenol: 4-Trifluoromethyl-phenol (commercially available), ES-MS m/e: 594.2 (M+H$^+$).

Example 17

{(3RS,4SR)-3-(3,4-Dichloro-phenyl)-4-[(SR)-1 (4-trifluoromethyl-phenoxy)-ethyl]-pyrrolidin-1-yl}-(4-methanesulfonyl-piperazin-1-yl)-methanone

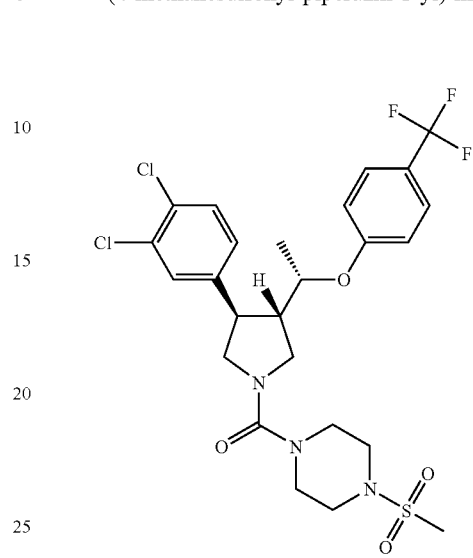

Mitsunobu Reaction According to General Procedure III:

Pyrrolidine intermediate: [(3RS,4SR)-3-(3,4-Dichloro-phenyl)-4-((RS)-1-hydroxy-ethyl)-pyrrolidin-1-yl]-(4-methanesulfonyl-piperazin-1-yl)-methanone (XII-A-1), Phenol: 4-Trifluoromethyl-phenol (commercially available), ES-MS m/e: 594.2 (M+H$^+$).

Example 18

N-(1-{(3RS,4SR)-3-(3,4-Dichloro-phenyl)-4-[(RS)-1-(4-trifluoromethyl-phenoxy)-ethyl]-pyrrolidine-1-carbonyl}-piperidin-4-yl)-N-methyl-methane-sulfonamide

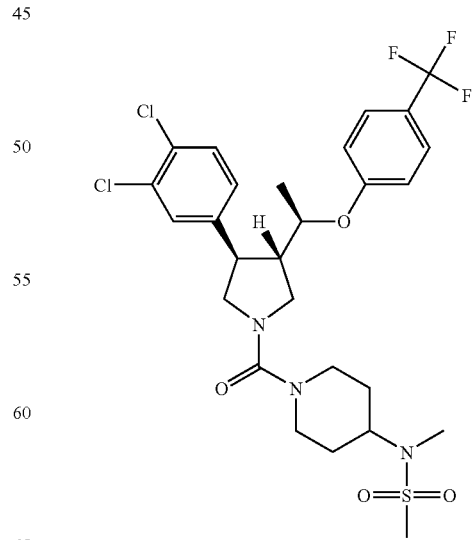

Coupling Reaction According to General Procedure II:

Pyrrolidine intermediate: (3RS,4SR)-3-(3,4-Dichlorophenyl)-4-[(R S)-1-(4-trifluoromethyl-phenoxy)-ethyl]-pyrrolidine (XV-B-1), Carbamoyl chloride: 4-(Methanesulfonyl-methyl-amino)-piperidine-1-carbonyl chloride, ES-MS m/e: 623.6 (M+H$^+$).

4-(Methanesulfonyl-methyl-amino)-piperidine-1-carbonyl chloride

To a stirred solution of carbonic acid ditrichloromethyl ester (triphosgene) (0.61 g, 2.08 mmol) in $CH_2Cl_2$ (30 mL) at −78° C., was added a solution of N-Methyl-N-piperidin-4-yl-methanesulfonamide (preparation described in the patent GB2000136) (1.00 g, 5.20 mmol) and pyridine (0.92 mL, 11.4 mmol) in $CH_2Cl_2$ (20 mL) over 1 hour. The temperature was raised to RT, and stirring was continued over night. The organic phase was washed with $H_2O$, dried over $Na_2SO_4$. Concentration under vacuo yielded 0.53 g (40%) of the title compound as a light yellow solid.

Example 19

{(3RS,4SR)-3-(3,4-Dichloro-phenyl)-4-[(RS)-1 (4-trifluoromethyl-phenoxy)-ethyl]-pyrrolidin-1-yl}-morpholin-4-yl-methanone

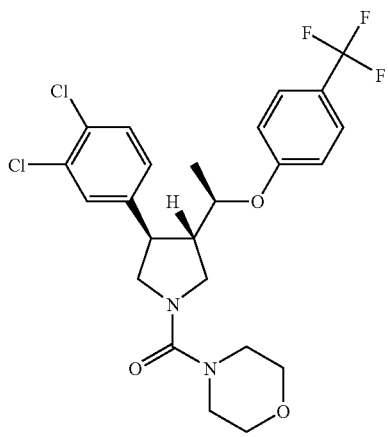

Coupling Reaction According to General Procedure II:

Pyrrolidine intermediate: (3RS,4SR)-3-(3,4-Dichlorophenyl)-4-[(RS)-1-(4-trifluoromethyl-phenoxy)-ethyl]-pyrrolidine (XV-B-1), Carbamoyl chloride: Morpholine-4-carbonyl chloride (commercially available), ES-MS m/e: 516.8 (M+H$^+$).

Example 20

N-[1-(2-{(3RS,4SR)-3-(3,4-Dichloro-phenyl)-4-[(RS)-1-(4-trifluoromethyl-phenoxy)-ethyl]-pyrrolidin-1-yl}-2-oxo-ethyl)-piperidin-4-yl]-N-methyl-methanesulfonamide

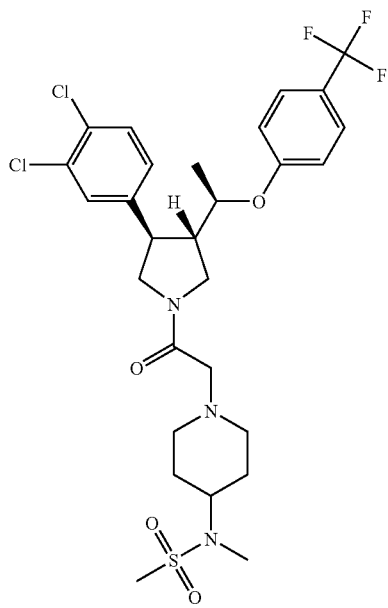

Coupling Reaction According to General Procedure IV:

Pyrrolidine intermediate: 2-Bromo-1-{(3RS,4SR)-3-(3,4-dichloro-phenyl)-4-[(RS)-1-(4-trifluoromethyl-phenoxy)-ethyl]-pyrrolidin-1-yl}-ethanone (XVI-B-1), Amine: N-Methyl-N-piperidin-4-yl-methanesulfonamide (preparation described in the patent GB2000136), ES-MS m/e: 635.6 (M+H$^+$).

Example 21

1'-(2-{(3RS,4SR)-3-(3,4-Dichloro-phenyl)-4-[(RS)-1-(4-trifluoromethyl-phenoxy)-ethyl]-pyrrolidin-1-yl}-2-oxo-ethyl)-[1,4']bipiperidinyl-2-one

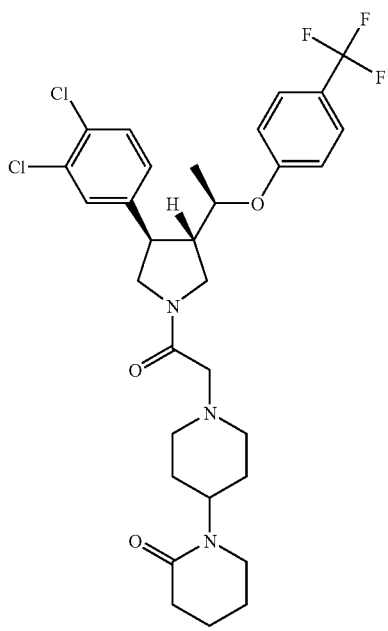

Coupling Reaction According to General Procedure IV:

Pyrrolidine intermediate: 2-Bromo-1-{(3RS,4SR)-3-(3,4-dichloro-phenyl)-4-[(RS)-1-(4-trifluoromethyl-phenoxy)-ethyl]-pyrrolidin-1-yl}-ethanone (XVI-B-1), Amine: [1,4']Bipiperidinyl-2-one (commercially available), ES-MS m/e: 625.8 (M+H$^+$).

Example 22

N-[1-(2-{(3RS,4SR)-3-(3,4-Dichloro-phenyl)-4-[(RS)-1-(4-trifluoromethyl-phenoxy)-ethyl]-pyrrolidin-1-yl}-2-oxo-ethyl)-piperidin-4-yl]-N-methyl-acetamide

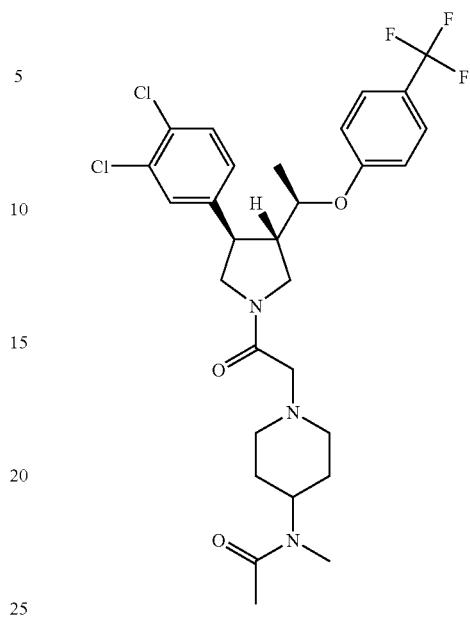

Coupling Reaction According to General Procedure IV:

Pyrrolidine intermediate: 2-Bromo-1-{(3RS,4SR)-3-(3,4-dichloro-phenyl)-4-[(RS)-1-(4-trifluoromethyl-phenoxy)-ethyl]-pyrrolidin-1-yl}-ethanone (XVI-B-1), Amine: N-Methyl-N-piperidin-4-yl-acetamide (preparation described in the U.S. Pat. No. 5,576,333), ES-MS m/e: 599.7 (M+H$^+$).

Example 23

1-{(3RS,4SR)-3-(3,4-Dichloro-phenyl)-4-[(RS)-1-(4-trifluoromethyl-phenoxy)-ethyl]-pyrrolidin-1-yl}-2-(4-methanesulfonyl-piperazin-1-yl)-ethanone

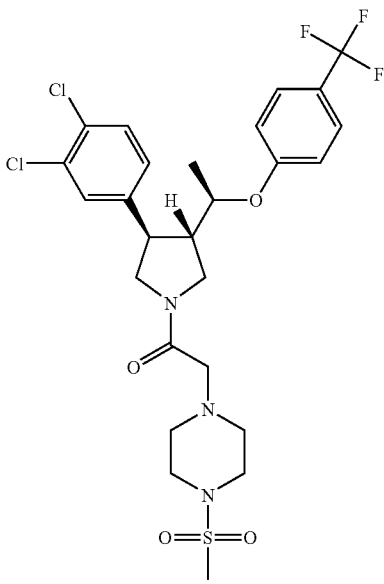

Coupling Reaction According to General Procedure IV:

Pyrrolidine intermediate: 2-Bromo-1-{(3RS,4SR)-3-(3,4-dichloro-phenyl)-4-[(RS)-1-(4-trifluoromethyl-phenoxy)-ethyl]-pyrrolidin-1-yl}-ethanone (XVI-B-1), Amine: 1-Methanesulfonyl-piperazine (commercially available), ES-MS m/e: 609.4 (M+H⁺).

Example 24

2-(4-Acetyl-piperazin-1-yl)-1-{(3RS,4SR)-3-(3,4-dichloro-phenyl)-4-[(RS)-1-(4-trifluoromethyl-phenoxy)-ethyl]-pyrrolidin-1-yl}-ethanone

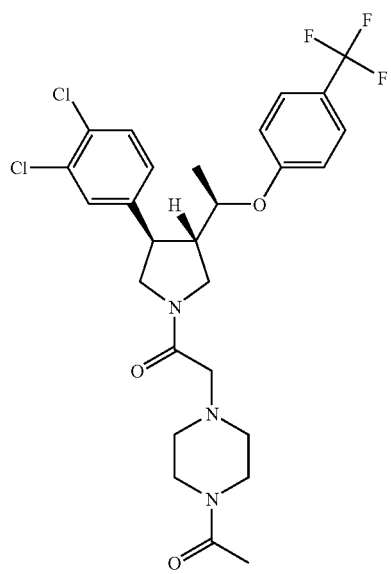

Coupling Reaction According to General Procedure IV:

Pyrrolidine intermediate: 2-Bromo-1-{(3RS,4SR)-3-(3,4-dichloro-phenyl)-4-[(RS)-1-(4-trifluoromethyl-phenoxy)-ethyl]-pyrrolidin-1-yl}-ethanone (XVI-B-1), Amine: 1-piperazin-1-yl-ethanone (commercially available), ES-MS m/e: 573.6 (M+H⁺).

Example 25

N-[1-(2-{(3RS,4SR)-3-(3,4-Dichloro-phenyl)-4-[(RS)-1-(4-trifluoromethyl-phenoxy)-ethyl]-pyrrolidin-1-yl}-2-oxo-ethyl)-piperidin-4-yl]-acetamide

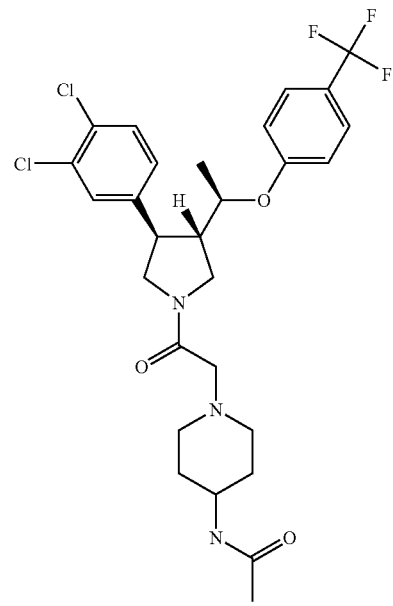

Coupling Reaction According to General Procedure IV:

Pyrrolidine intermediate: 2-Bromo 1-{(3RS,4SR)-3-(3,4-dichloro-phenyl)-4-[(RS)-1-(4-trifluoromethyl-phenoxy)-ethyl]-pyrrolidin-1-yl}-ethanone (XVI-B-1), Amine: N-Piperidin-4-yl-acetamide (commercially available), ES-MS m/e: 587.7 (M+H⁺).

Example 26

1-{(3RS,4SR)-3-(3,4-Dichloro-phenyl)-4-[(RS)-1-(4-trifluoromethyl-phenoxy)-ethyl]-pyrrolidin-1-yl}-2-(4-hydroxy-piperidin-1-yl)-ethanone

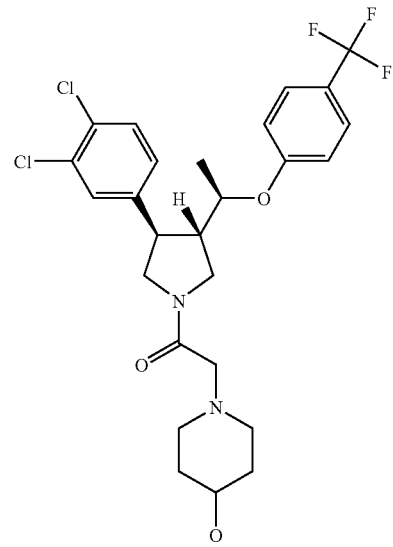

Coupling Reaction According to General Procedure IV:

Pyrrolidine intermediate: 2-Bromo-1-[(3RS,4SR)-3-(3,4-dichloro-phenyl)-4-[(RS)-1-(4-trifluoromethyl-phenoxy)-ethyl]-pyrrolidin-1-yl]-ethanone (XVI-B-1),
Amine: Piperidin-4-ol (commercially available),
ES-MS m/e: 545.2 (M+H$^+$).

Example 27

{(3RS,4SR)-3-(3,4-Dichloro-phenyl)-4-[(RS)-1-(4-trifluoromethyl-phenoxy)-ethyl]-pyrrolidin-1-yl}-((R)-4-methanesulfonyl-3-methyl-piperazin-1-yl)-methanone

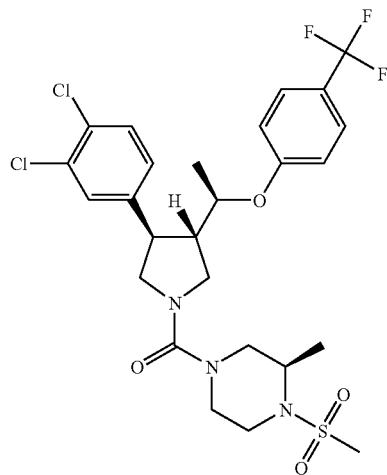

Coupling Reaction According to General Procedure II:
Pyrrolidine intermediate: (3RS,4SR)-3-(3,4-Dichloro-phenyl)-4-[(RS)-1-(4-trifluoromethyl-phenoxy)-ethyl]-pyrrolidine (XV-B-1),
Carbamoyl chloride: (R)-4-Methanesulfonyl-3-methyl-piperazine-1-carbonyl chloride,
ES-MS m/e: 609.6 (M+H$^+$).

(R)-4-Methanesulfonyl-3-methyl-piperazine-1-carbonyl chloride

First step: To a stirred solution of commercially available (R)-3-methyl-piperazine-1-carboxylic acid tert-butyl ester (8.78 g, 44 mmol) in CH$_2$Cl$_2$ (80 mL) at 0° C. were added Et$_3$N (12.15 mL, 88 mmol) and methanesulfonyl chloride (5.09 mL, 66 mmol). Stirring was continued at RT overnight, the reaction was poured onto water and extracted with CH$_2$Cl$_2$. The combined organic phases were dried on Na$_2$SO$_4$ and concentrated under vacuo. The crude product was dissolved in CH$_2$Cl$_2$ (50 mL) and TFA (15 mL) was added. After 2 hours at RT, the volatiles were removed under vacuo, the crude was dissolved in CH$_2$Cl$_2$ and washed with aq. NaHCO$_3$ (until pH=8). The organic phase was dried on Na$_2$SO$_4$ and concentrated under vacuo to yield 2.63 g (34%) of (R)-1-methanesulfonyl-2-methyl-piperazine as a light yellow oil.

Second step: To a stirred solution of carbonic acid ditrichloromethyl ester (triphosgene) (1.17 g, 3.95 mmol) in CH$_2$Cl$_2$ (20 mL) at −78° C., was added a solution of (R)-1-methanesulfonyl-2-methyl-piperazine (1.76 g, 9.9 mmol) and pyridine (1.60 mL, 20 mmol) in CH$_2$Cl$_2$ (20 mL) over 1 hour. The temperature was raised to RT, and stirring was continued over night. The organic phase was washed with H$_2$O, dried over Na$_2$SO$_4$. Concentration under vacuo and flash chromatography (SiO$_2$, EtOAc/H, 1:1) yielded 1.70 g (71%) of (R)-4-methanesulfonyl-3-methyl-piperazine-1-carbonyl chloride as a light yellow solid.

Example 28

{(3RS,4SR)-3-(3,4-Dichloro-phenyl)-4-[(RS)-1-(4-trifluoromethyl-phenoxy)-ethyl]-pyrrolidin-1-yl}-((S)-4-methanesulfonyl-3-methyl-piperazin-1-yl)-methanone

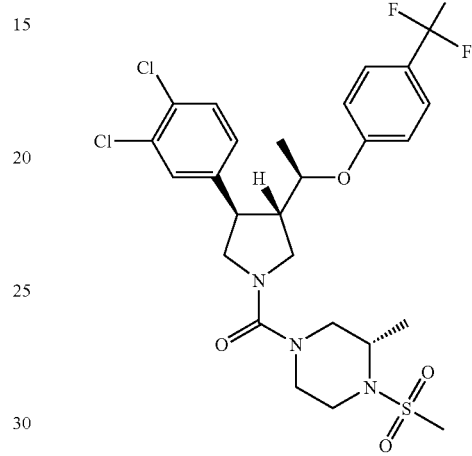

Coupling Reaction According to General Procedure II:
Pyrrolidine intermediate: (3RS,4SR)-3-(3,4-Dichloro-phenyl)-4-[(RS)-1-(4-trifluoromethyl-phenoxy)-ethyl]-pyrrolidine (XV-B-1),
Carbamoyl chloride: (S)-4-Methanesulfonyl-3-methyl-piperazine-1-carbonyl chloride,
ES-MS m/e: 609.6 (M+H$^+$).

(S)-4-Methanesulfonyl-3-methyl-piperazine-1-carbonyl chloride

First step: To a stirred solution of commercially available (S)-3-methyl-piperazine-1-carboxylic acid tert-butyl ester (2.38 g, 12 mmol) in CH$_2$Cl$_2$ (25 mL) at 0° C. were added pyridine (1.91 mL, 24 mmol) and methanesulfonyl chloride (0.92 mL, 12 mmol). Stirring was continued at RT overnight, the reaction was poured onto water and extracted with CH$_2$Cl$_2$. The combined organic phases were dried on Na$_2$SO$_4$ and concentrated under vacuo. The crude product was dissolved in CH$_2$Cl$_2$ (20 mL) and TFA (4 mL) was added. After 2 hours at RT, the volatiles were removed under vacuo, the crude was dissolved in CH$_2$Cl$_2$ and washed with aq. NaHCO$_3$ (until pH=8). The organic phase was dried on Na$_2$SO$_4$ and concentrated under vacuo to yield 0.83 g (39%) of (s)-1-methanesulfonyl-2-methyl-piperazine as a light yellow oil.

Second step: To a stirred solution of carbonic acid ditrichloromethyl ester (triphosgene) (560 mg, 1.88 mmol) in CH$_2$Cl$_2$ (10 mL) at −78° C., was added a solution of (S)-1-methanesulfonyl-2-methyl-piperazine (838 mg, 4.70 mmol) and pyridine (0.74 mL, 9.4 mmol) in CH$_2$Cl$_2$ (10 mL) over 1 hour. The temperature was raised to RT, and stirring was continued over night. The organic phase was washed with H$_2$O, dried over Na$_2$SO$_4$. Concentration under vacuo and flash chromatography (SiO$_2$) EtOAc/H, 1:1) yielded 0.70 g (62%) of (S)-4-methanesulfonyl-3-methyl-piperazine-1-carbonyl chloride as a light yellow solid.

Example 29

1-{(3RS,4SR)-3-(3,4-Dichloro-phenyl)-4-[(RS)-1-(4-trifluoromethyl-phenoxy)-ethyl]-pyrrolidin-1-yl}-5-morpholin-4-yl-pentan-1-one

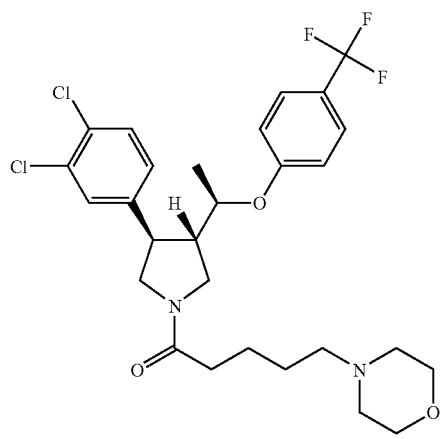

Amide Coupling According to General Procedure I:
Pyrrolidine intermediate: (3RS,4SR)-3-(3,4-Dichloro-phenyl)-4-[(RS)-1-(4-trifluoromethyl-phenoxy)-ethyl]-pyrrolidine (XV-B-1),
Carboxylic acid: 5-Morpholin-4-yl-pentanoic acid (described in *J. Molecular Structure,* 2001, 560, p. 261),
ES-MS m/e: 573.1 (M+H⁺).

Example 30

[(3SR,4RS)-3-[(RS)-1-(3,4-Dichloro-phenoxy)-ethyl]-4-(3,4-dichloro-phenyl)-pyrrolidin-1-yl]-(4-methanesulfonyl-piperazin-1-yl)-methanone

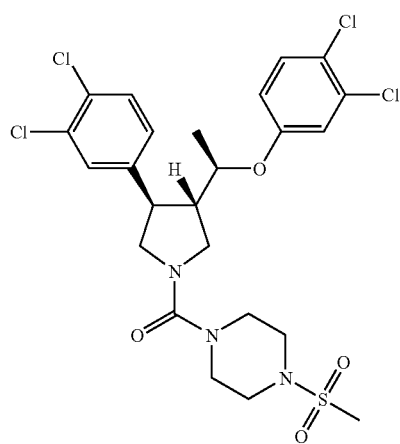

Mitsunobu Reaction According to General Procedure III:
Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1),
Phenol: 3,4-Dichloro-phenol (commercially available),
ES-MS m/e: 594.1 (M+H⁺).

Example 31

[(3RS,4SR)-3-(3,4-Dichloro-phenyl)-4-((RS)-1-p-tolyloxy-ethyl)-pyrrolidin-1-yl]-(4-methanesulfonyl-piperazin-1-yl)-methanone

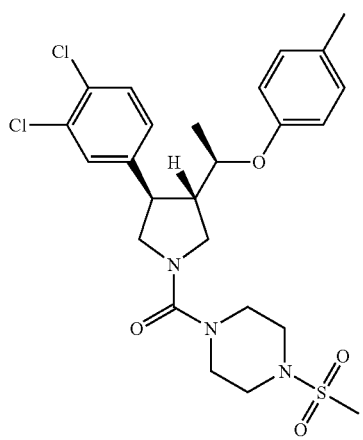

Mitsunobu Reaction According to General Procedure III:
Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1),
Phenol: 4-Methyl-phenol (commercially available),
ES-MS m/e: 540.2 (M+H⁺).

Example 32

[(3RS,4SR)-3-(3,4-Dichloro-phenyl)-4-((RS)-1-m-tolyloxy-ethyl)-pyrrolidin-1-yl]-(4-methanesulfonyl-piperazin-1-yl-methanone

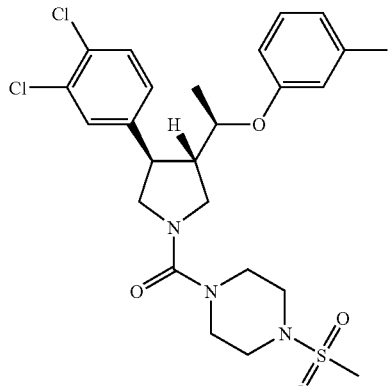

Mitsunobu Reaction According to General Procedure III:
Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1),
Phenol: 3-Methyl-phenol (commercially available),
ES-MS m/e: 540.2 (M+H⁺).

Example 33

4-{(RS)-1-[(3SR,4RS)-4-(3,4-Dichloro-phenyl)-1-(4-methanesulfonyl-piperazine-1-carbonyl)-pyrrolidin-3-yl]ethoxy}-benzonitrile

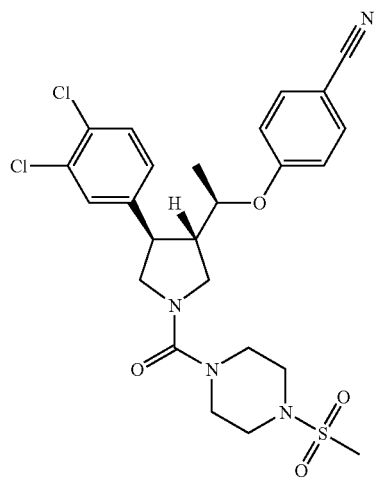

Mitsunobu Reaction According to General Procedure III:
Pyrrolidine intermediate: [(3RS,4SR)-3-(3,4-Dichlorophenyl)-4-((SR)-1-hydroxy-ethyl)-pyrrolidin-1-yl]-(4-methanesulfonyl-piperazin-1-yl)-methanone (XII-B-1),
Phenol: 4-Hydroxy-benzonitrile (commercially available),
ES-MS m/e: 551.3 (M+H$^+$).

Example 34

{(3RS,4SR)-3-(3,4-Dichloro-phenyl)-4-[(RS)-1-(4-fluoro-phenoxy)-ethyl]-pyrrolidin-1-yl}-(4-methanesulfonyl-piperazin-1-yl)-methanone

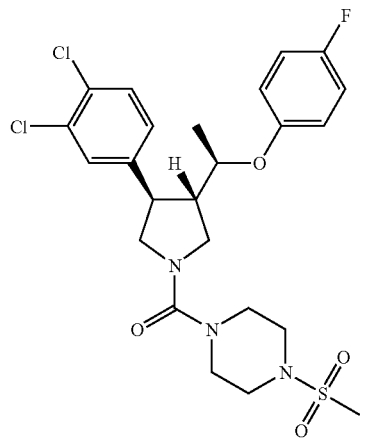

Mitsunobu Reaction According to General Procedure III:
Pyrrolidine intermediate: [(3RS,4SR)-3-(3,4-Dichlorophenyl)-4-((SR)-1-hydroxy-ethyl)-pyrrolidin-1-yl]-(4-methanesulfonyl-piperazin-1-yl)-methanone (XII-B-1),
Phenol, 4-Fluoro-phenol (commercially available),
ES-MS m/e: 544.3 (M+H$^+$).

Example 35

{(3RS,4SR)-3-(3,4-Dichloro-phenyl)-4-[(RS)-1(3-fluoro-phenoxy)-ethyl]-pyrrolidin-1-yl}-(4-methanesulfonyl-piperazin-1-yl)-methanone

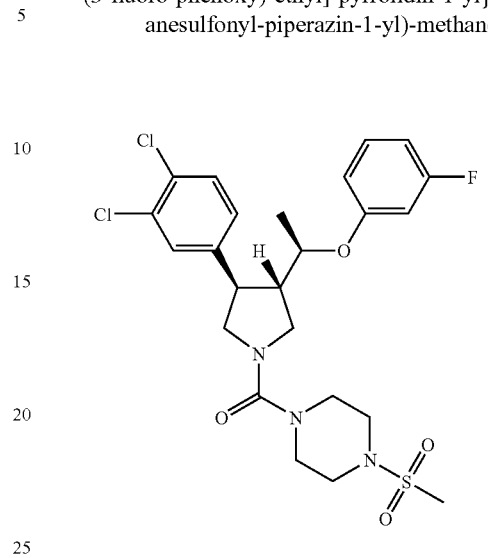

Mitsunobu Reaction According to General Procedure III:
Pyrrolidine intermediate: [(3RS,4SR)-3-(3,4-Dichlorophenyl)-4-((SR)-hydroxy-ethyl)-pyrrolidin-1-yl]-(4-methanesulfonyl-piperazin-1-yl)-methanone (XII-B-1),
Phenol: 3-Fluoro-phenol (commercially available),
ES-MS m/e: 544.3 (M+H$^+$).

Example 36

[(3SR,4RS)-3-[(R)-1-(4-Chloro-phenoxy)-ethyl]-4-(3,4-dichloro-phenyl)-pyrrolidin-1-yl]-(4-methanesulfonyl-piperazin-1-yl)-methanone

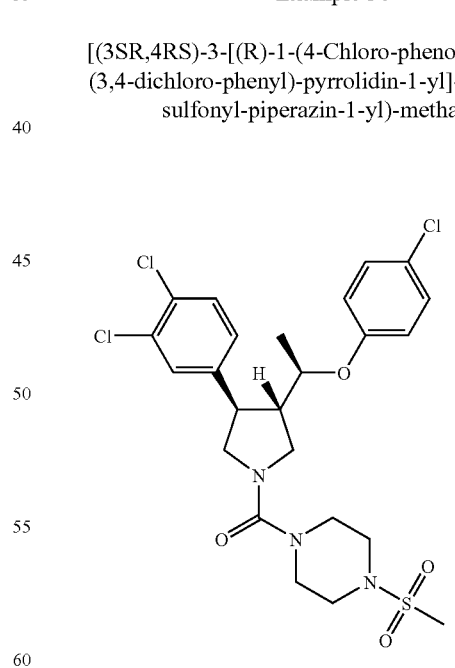

Mitsunobu Reaction According to General Procedure III:
Pyrrolidine intermediate: [(3RS,4SR)-3-(3,4-Dichlorophenyl)-4-((SR)-1-hydroxy-ethyl)-pyrrolidin-1-yl]-(4-methanesulfonyl-piperazin-1-yl)-methanone (XII-B-1),
Phenol: 4-Chloro-phenol (commercially available), ES-MS m/e: 560.2 (M+H$^+$).

Example 37

[(3SR,4RS)-3-[(RS)-1-(3-Chloro-phenoxy)-ethyl]-4-(3,4-dichloro-phenyl)-pyrrolidin-1-yl]-(4-methanesulfonyl-piperazin-1-yl)-methanone

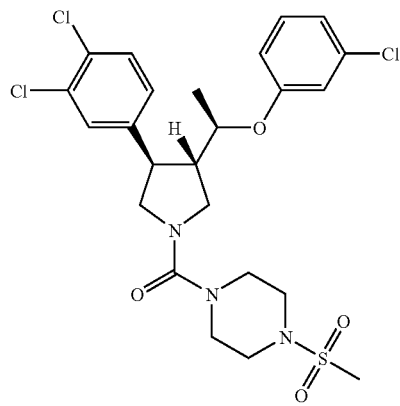

Mitsunobu Reaction According to General Procedure III:
Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1),
Phenol, 3-Chloro-phenol (commercially available),
ES-MS m/e: 562.2 (M+H$^+$).

Example 38

{(3RS,4SR)-3-(3,4-Dichloro-phenyl)-4-[(RS)-1-(4-methoxy-phenoxy)-ethyl]-pyrrolidin-1-yl}-(4-methanesulfonyl-piperazin-1-yl)-methanone

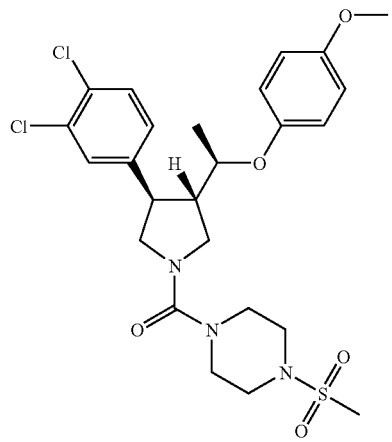

Mitsunobu Reaction According to General Procedure III:
Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1),
Phenol: 4-Methoxy-phenol (commercially available),
ES-MS m/e: 558.3 (M+H$^+$).

Example 39

[(3SR,4RS)-3-[(RS)-1-(5-Chloro-pyridin-2-yloxy)-ethyl]-4-(3,4-dichloro-phenyl)-pyrrolidin-1-yl]-(4-methanesulfonyl-piperazin-1-yl)-methanone

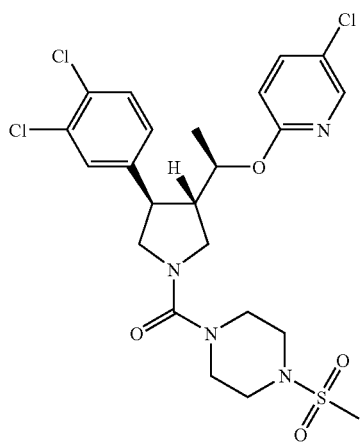

Mitsunobu Reaction According to General Procedure III:
Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1),
Pyridinol: 5-Chloro-pyridin-2-ol (commercially available),
ES-MS m/e: 561.2 (M+H$^+$).

Example 40

[(3SR,4RS)-3-[(RS)-1-(6-Chloro-pyridin-3-yloxy)-ethyl]-4-(3,4-dichloro-phenyl)-pyrrolidin-1-yl]-(4-methanesulfonyl-piperazin-1-yl)-methanone

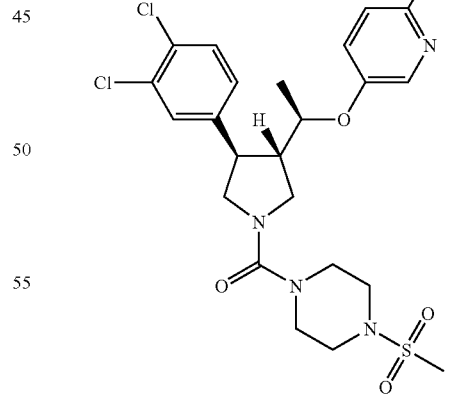

Mitsunobu Reaction According to General Procedure III:
Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1),
Pyridinol: 6-Chloro-pyridin-3-ol (commercially available), ES-MS m/e: 563.1 (M+H$^+$).

Example 41

[(3SR,4RS)-3-[(RS)-1-(3-Chloro-4-fluoro-phenoxy)-ethyl]-4-(3,4-dichloro-phenyl)-pyrrolidin-1-yl]-(4-methanesulfonyl-piperazin-1-yl)-methanone

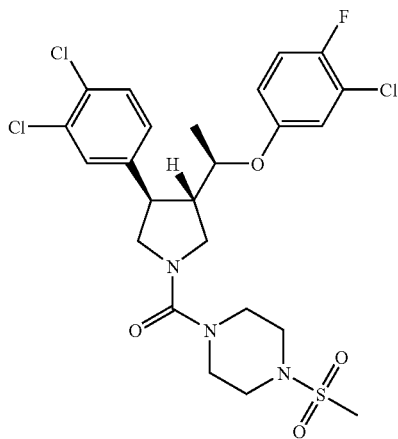

Mitsunobu Reaction According to General Procedure III:
Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1),
Phenol: 3-Chloro-4-fluoro-phenol (commercially available),
ES-MS m/e: 579.0 (M+H$^+$).

Example 42

[(3RS,4SR)-3-(3,4-Dichloro-phenyl)-4-[(RS)-1-(pyrimidin-2-yloxy)-ethyl]-pyrrolidin-1-yl}-(4-methanesulfonyl-piperazin-1-yl)-methanone

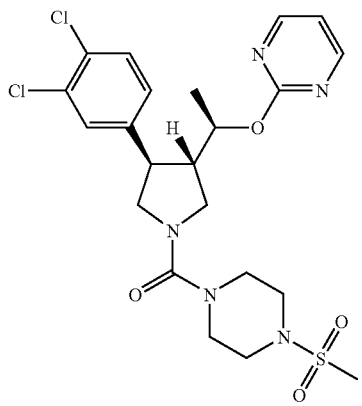

Mitsunobu Reaction According to General Procedure III:
Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1),
Pyrimidinol: Pyrimidin-2-ol (commercially available),
ES-MS m/e: 528.0 (M+H$^+$).

Example 43

{(3RS,4SR)-3-(3)-4-Dichloro-phenyl)-4-[(RS)-1-(4-imidazol-1-yl-phenoxy)-ethyl}-pyrrolidin-1-yl]-(4-methanesulfonyl-piperazin-1-yl)-methanone

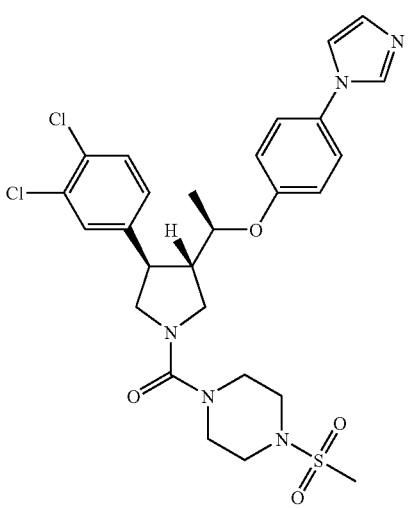

Mitsunobu Reaction According to General Procedure III:
Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1),
Phenol: 4-Imidazol-1-yl-phenol (commercially available),
ES-MS m/e: 592.1 (M+H$^+$).

Example 44

{(3RS,4SR)-3-(3,4-Dichloro-phenyl)-4-[(RS)-1-(3-trifluoromethyl-phenoxy)-ethyl]-pyrrolidin-1-yl}-(4-methanesulfonyl-piperazin-1-yl)-methanone

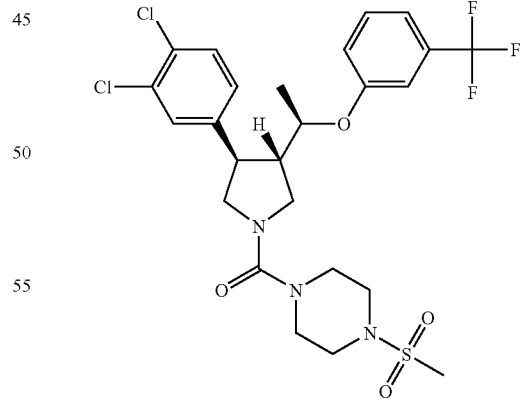

Mitsunobu Reaction According to General Procedure III:
Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1),
Phenol: 3-Trifluoromethyl-phenol (commercially available), ES-MS m/e: 594.2 (M+H$^+$).

Example 45

4-{(SR)-1-[(3SR,4RS)-4-(3,4-Dichloro-phenyl)-1-(4-methanesulfonyl-piperazine-1-carbonyl)-pyrrolidin-3-yl]-ethoxy}-benzonitrile

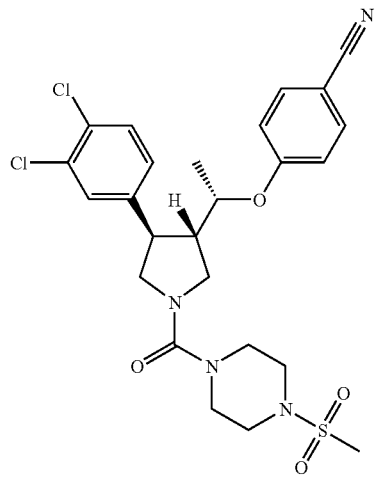

Mitsunobu Reaction According to General Procedure III:
Pyrrolidine intermediate: [(3RS,4SR)-3-(3,4-Dichloro-phenyl)-4-((RS)-1-hydroxy-ethyl)-pyrrolidin-1-yl]-(4-methanesulfonyl-piperazin-1-yl)-methanone (XII-A-1),
Phenol: 4-Hydroxy-benzonitrile (commercially available),
ES-MS m/e: 551.2 (M+H$^+$).

Example 46

{(3RS,4SR)-3-(3,4-Dichloro-phenyl)-4-[(SR)-1-(4-fluoro-phenoxy)-ethyl]-pyrrolidin-1-yl}-(4-methanesulfonyl-piperazin-1-yl)-methanone

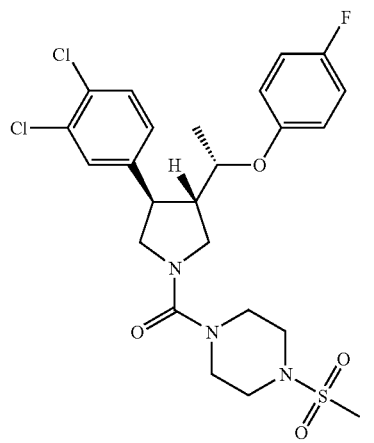

Mitsunobu Reaction According to General Procedure III:
Pyrrolidine intermediate: [(3RS,4SR)-3-(3,4-Dichloro-phenyl)-4-((RS)-1-hydroxy-ethyl)-pyrrolidin-1-yl]-(4-methanesulfonyl-piperazin-1-yl)-methanone (XII-A-1),
Phenol: 4-Fluoro-phenol (commercially available), ES-MS m/e: 546.2 (M+H$^+$).

Example 47

{(3RS,4SR)-3-(3,4-Dichloro-phenyl)-4-[(SR)-1-(3-fluoro-phenoxy)-ethyl]-pyrrolidin-1-yl}-(4-methanesulfonyl-piperazin-1-yl)-methanone

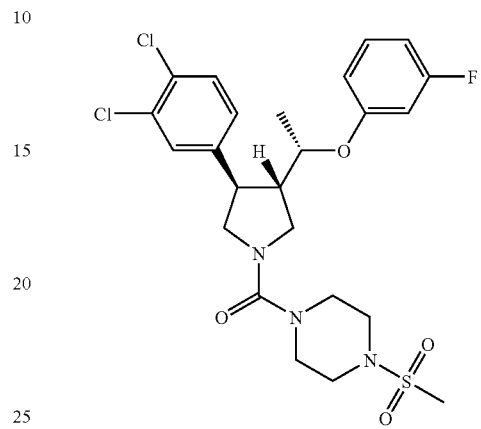

Mitsunobu Reaction According to General Procedure III:
Pyrrolidine intermediate; [(3RS,4SR)-3-(3,4-Dichloro-phenyl)-4-((RS)-1-hydroxy-ethyl)-pyrrolidin-1-yl]-(4-methanesulfonyl-piperazin-1-yl)-methanone (XII-A-1),
Phenol: 3-Fluoro-phenol (commercially available),
ES-MS m/e: 544.3 (M+H$^+$).

Example 48

[(3SR,4RS)-3-[(SR)-1-(4-Chloro-phenoxy)-ethyl]-4(3,4-dichloro-phenyl)-pyrrolidin-1-yl]-(4-methanesulfonyl-piperazin-1-yl)-methanone

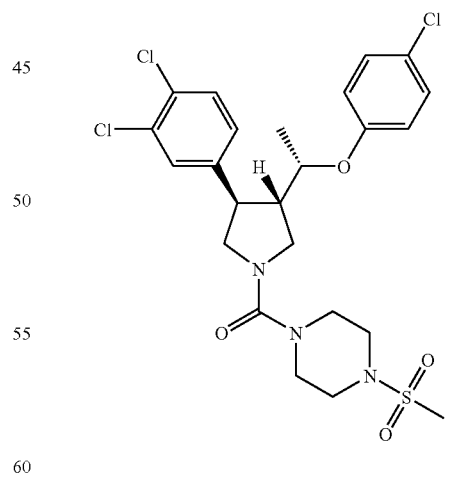

Mitsunobu Reaction According to General Procedure III:
Pyrrolidine intermediate: [(3RS,4SR)-3-(3,4-Dichloro-phenyl)-4-((RS)-1-hydroxy-ethyl)-pyrrolidin-1-yl]-(4-methanesulfonyl-piperazin-1-yl)-methanone (XII-A-1),
Phenol: 4-Chloro-phenol (commercially available),
ES-MS m/e: 562.2 (M+H$^+$).

Example 49

{(3RS,4SR)-3-(3,4-Dichloro-phenyl)-4-[(SR)-1-(3-trifluoromethyl-phenoxy)-ethyl]-pyrrolidin-1-yl}-4-methanesulfonyl-piperazin-1-yl)-methanone

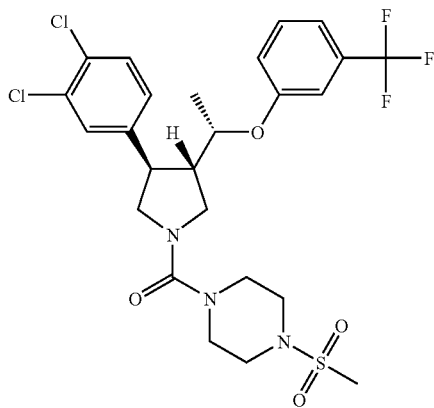

Mitsunobu Reaction According to General Procedure III:
Pyrrolidine intermediate: [(3RS,4SR)-3-(3,4-Dichloro-phenyl)-4-((RS)-1-hydroxy-ethyl)-pyrrolidin-1-yl]-(4-methanesulfonyl-piperazin-1-yl)-methanone (XII-A-1),
Phenol: 3-Trifluoromethyl-phenol (commercially available),
ES-MS m/e: 594.2 (M+H$^+$).

Example 50

1-{(3RS,4SR)-3-(3,4-Dichloro-phenyl)-4-[(RS)-1-(4-trifluoromethyl-phenoxy)-ethyl]-pyrrolidin-1-yl}-2-[4-(3-hydroxypropyl)-piperazin-1-yl]-ethanone

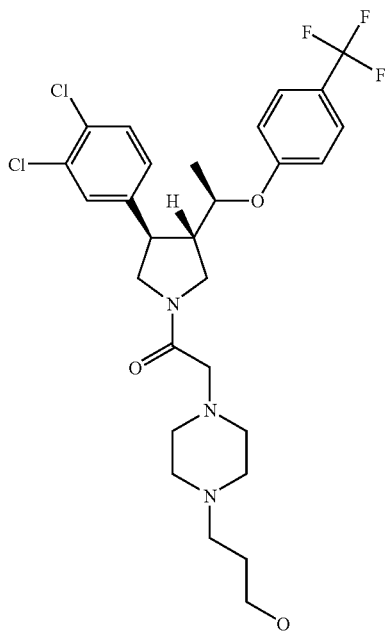

Coupling Reaction According to General Procedure IV:
Pyrrolidine intermediate: 2-Bromo-1-{(3RS,4SR)-3-(3,4-dichloro-phenyl)-4-[(RS)-1 (4-trifluoromethyl-phenoxy)-ethyl]-pyrrolidin-1-yl}-ethanone (XVI-B-1),
Amine: 3-piperazin-1-yl-propan-1-ol (commercially available),
ES-MS m/e: 588.1 (M+H$^+$).

Example 51

{(3RS,4SR)-3-(3,4-Dichloro-phenyl)-4-[(RS)-1-(5-fluoro-pyrimidin-2-yloxy)-ethyl]-pyrrolidin-1-yl}-(4-methanesulfonyl-piperazin-1-yl)-methanone

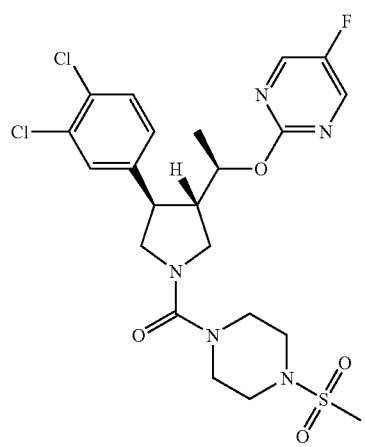

Mitsunobu Reaction According to General Procedure III:
Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1),
Pyrimidinol: 5-Fluoro-pyrimidin-2-ol (commercially available),
ES-MS m/e: 545.7 (M+H$^+$).

Example 52

{(3RS,4SR)-3-(3,4-Dichloro-phenyl)-4-[(RS)-1-(4-trifluoromethyl-phenoxy)-ethyl]-pyrrolidin-1-yl}-[4-(2-diethylamino-ethyl)-piperazin-1-yl]-methanone

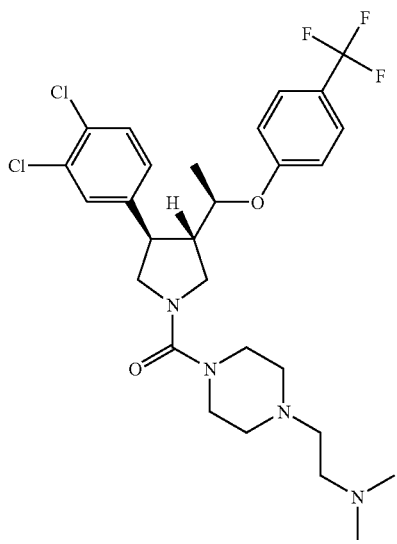

a) (3RS,4SR)-3-(3,4-Dichloro-phenyl)-4-[(RS)-1-(4-trifluoromethyl-phenoxy)-ethyl]-pyrrolidine-1-carbonyl chloride To a stirred solution of carbonic acid ditrichloromethyl ester (triphosgene) (29 mg, 0.098 mmol) in CH$_2$Cl$_2$ (2 mL) at −78° C., was added a solution of (3RS,4SR)-3-(3,4-dichloro-phenyl)-4-[(RS)-1-(4-trifluoromethyl-phenoxy)-ethyl]-pyrrolidine (intermediate XV-B-1) (100 mg, 0.25 mmol) and pyridine (0.043 mL, 0.54 mmol) in CH$_2$Cl$_2$ (2 mL) over 30 minutes. The temperature was raised to RT, and stirring was continued over night. The organic phase was washed with H$_2$O, dried over Na$_2$SO$_4$. Concentration under vacuo yielded 58 mg (50%) of the title compound as a light yellow solid.

b) {(3RS,4SR)-3-(3,4-Dichloro-phenyl)-4-[(RS)-1-(4-trifluoromethyl-phenoxy)-ethyl]pyrrolidin-1-yl}-[4-(2-dimethylamino-ethyl)-piperazin-1-yl]-methanone To a stirred solution of (3RS,4SR)-3-(3,4-dichloro-phenyl)-4-[(RS)-1-(4-trifluoromethyl-phenoxy)-ethyl]-pyrrolidine-1-carbonyl chloride (58 mg, 0.12 mmol) in CH$_2$Cl$_2$ (2 ml) were added Et$_3$N (0.02 mL, 0.15 mmol) and dimethyl-(2-piperazin-1-yl-ethyl)-amine (0.03 mL) (commercially available). Stirring was continued overnight, and the reaction mixture was concentrated under vacuo and directly purified by flash chromatography (SiO$_2$, CH$_2$Cl$_2$/MeOH/NH$_3$, 9/4/1) to yield 46 mg (63%) of the title compound as light yellow oil. ES-MS m/e: 587.3 (M+H$^+$).

Example 53

[(3SR,4RS)-3-[(RS)-1-(5-Chloro-pyrimidin-2-yloxy)-ethyl]-4-(3,4-dichloro-phenyl)-pyrrolidin-1-yl]-(4-methanesulfonyl-piperazin-1-yl)-methanone

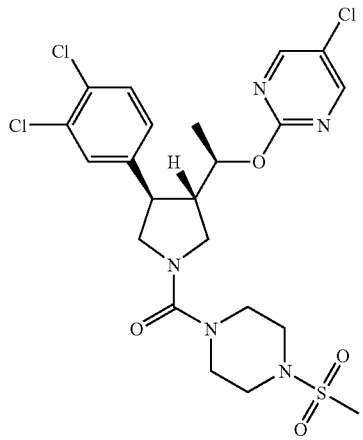

Mitsunobu Reaction According to General Procedure III:
Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1),
Pyrimidinol: 5-Chloro-pyrimidin-2-ol (commercially available),
ES-MS m/e: 562.7 (M+H$^+$).

Example 54

[(3SR,4RS)-3-[(RS)-1-(5-Chloro-pyridin-2-yloxy)-ethyl]-4-(3,4-dichloro-phenyl)-pyrrolidin-1-yl]-((R)-4-methanesulfonyl-3-methyl-piperazin-1-yl)-methanone

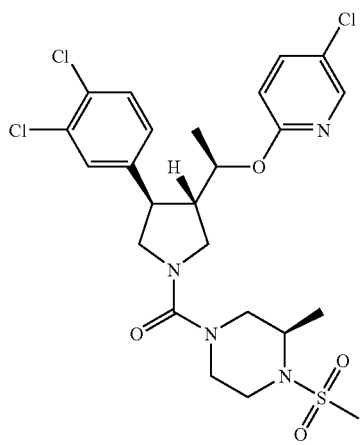

Coupling Reaction According to General Procedure II:
Pyrrolidine intermediate: 5-Chloro-2-{(RS)-1-[(3SR,4RS)-4-(3,4-dichloro-phenyl)-pyrrolidin-3-yl]-ethoxy}-pyridine (XV-B-2),
Carbamoyl chloride: (R)-4-Methanesulfonyl-3-methyl-piperazine-carbonyl chloride,
ES-MS m/e: 577.2 (M+H$^+$).

Example 55

1-[(3SR,4RS)-3-[(RS)-1-(5-Chloro-pyridin-2-yloxy)-ethyl]-4-(3,4-dichloro-phenyl)-pyrrolidin-1- yl]-5-morpholin-4-yl-pentan-1-one

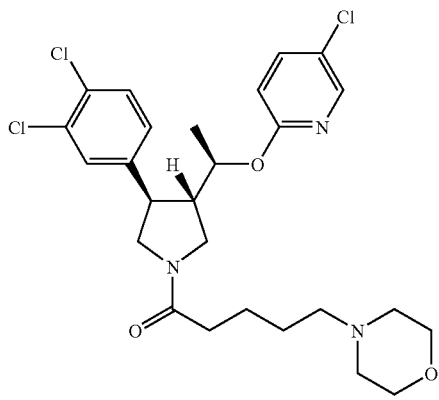

Amid Coupling According to General Procedure I:

Pyrrolidine intermediate: 5-Chloro-2-{(RS)-1-[(3SR,4RS)-4-(3,4-dichloro-phenyl)-pyrrolidin-3-yl]-ethoxy}-pyridine (XV-B-2), Carboxylic acid: 5-Morpholin-4-yl-pentanoic acid (described in *J. Molecular Structure*, 2001, 560, p. 261), ES-MS m/e: 542.3 (M+H$^+$).

Example 56

[(3SR,4RS)-3-[(RS)-1-(5-Chloro-pyridin-2-yloxy)-ethyl]-4-(3,4-dichloro-phenyl)-pyrrolidin-1-yl]-[4-(2-dimethylamino-ethyl)-piperazin-1-yl]-methanone

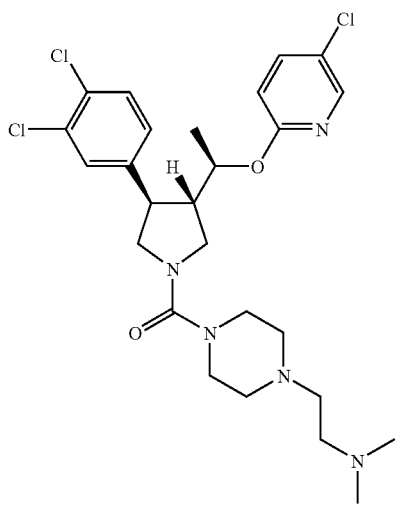

a) (3SR,4RS)-3-[(RS)-1-(5-Chloro-pyridin-2-yloxy)-ethyl]-4-(3,4-dichloro-phenyl)-pyrrolidine-1-carbonyl chloride To a stirred solution of carbonic acid ditrichloromethyl ester (triphosgene) (22 mg, 0.074 mmol) in CH$_2$Cl$_2$ (3 mL) at −78° C., was added a solution of 5-chloro-2-{(RS)-1-[(3SR,4RS)-4-(3,4-dichloro-phenyl)-pyrrolidin-3-yl]-ethoxy}-pyridine (intermediate XV-B-2) (70 mg, 0.19 mmol) and pyridine (0.033 mL, 0.41 mmol) in CH$_2$Cl$_2$ (2 mL) over 30 minutes. The temperature was raised to RT, and stirring was continued over night. The organic phase was washed with H$_2$O, dried over Na$_2$SO$_4$. Concentration under vacuo yielded and column chromatography (SiO$_2$, EtOAc/H, 1:1) yielded 80 mg (98%) of the title compound as a light yellow solid.

b) [(3SR,4RS)-3-[(RS)-1-(5-Chloro-pyridin-2-yloxy)-ethyl]-4-(3,4-dichloro-phenyl)-pyrrolidin-1-yl]-[4-(2-dimethylamino-ethyl)-piperazin-1-yl]-methanone To a stirred solution of (3SR,4RS)-3-[(RS)-1-(5-chloro-pyridin-2-yloxy)-ethyl]-4-(3,4-dichloro-phenyl)-pyrrolidine-1-carbonyl chloride (80 mg, 0.18 mmol) in CH$_2$Cl$_2$ (2 mL) were added Et$_3$N (0.03 mL, 0.15 mmol) and dimethyl-(2-piperazin-1-yl-ethyl)-amine (0.035 mL) (commercially available). Stirring was continued overnight, and the reaction mixture was concentrated under vacuo and directly purified by flash chromatography (SiO$_2$, CH$_2$Cl$_2$/MeOH/NH$_3$, 9/4/1) to yield 36 mg (35%) the title compound as light yellow oil. ES-MS m/e: 553.8 (M+H$^+$).

Example 57

{(3RS,4SR)-3-(3,4-Dichloro-phenyl)-4-[(SR)-1-(5-fluoro-pyridin-2-yloxy)-ethyl]-pyrrolidin-1-yl}-(4-methanesulfonyl-piperazin-1-yl)-methanone

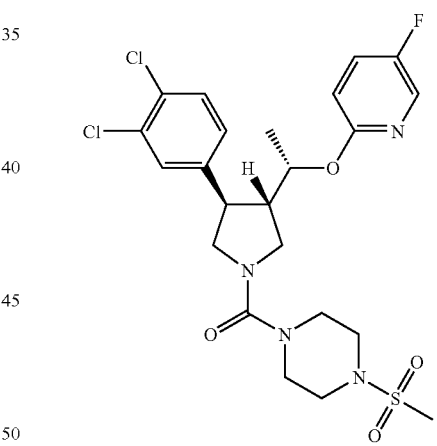

Mitsunobu Reaction According to General Procedure III:

Pyrrolidine intermediate: [(3RS,4SR)-3-(3,4-Dichloro-phenyl)-4-((RS)-1-hydroxy-ethyl)-pyrrolidin-1-yl]-(4-methanesulfonyl-piperazin-1-yl)-methanone (XII-A-1), Pyridinol, 5-Fluoro-pyridin-2-ol (commercially available), ES-MS m/e: 545.1 (M+H$^+$).

Example 58

{(3RS,4SR)-3-(3,4-Dichloro-phenyl)-4-[(SR)-1-(5-methyl-pyridin-2-yloxy)-ethyl]-pyrrolidin-1-yl}-(4-methanesulfonyl-piperazin-1-yl)-methanone

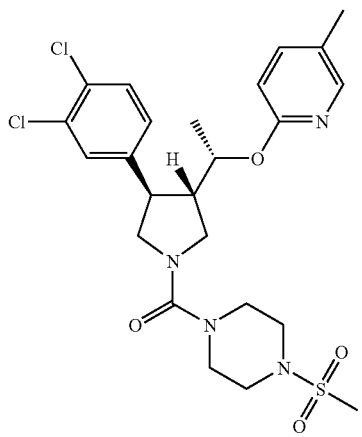

Mitsunobu Reaction According to General Procedure III:

Pyrrolidine intermediate: [(3RS,4SR)-3-(3,4-Dichloro-phenyl)-4-((RS)-1-hydroxy-ethyl)-pyrrolidin-1-yl]-(4-methanesulfonyl-piperazin-1-yl)-methanone (XII-A-1), Pyridinol: 5-Methyl-pyridin-2-ol (commercially available), ES-MS m/e: 542.7 (M+H$^+$).

Example 59

{(3RS,4SR)-3-(3,4-Dichloro-phenyl)-4-[(RS)-1-(5-fluoro-pyridin-2-yloxy)-ethyl]-pyrrolidin-1-yl}-(4-methanesulfonyl-piperazin-1-yl)-methanone

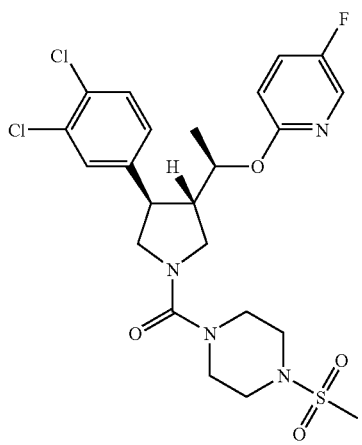

Mitsunobu Reaction According to General Procedure III:

Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin 1-yl)-methanone (XII-B-1), Pyridinol: 5-Fluoro-pyridin-2-ol (commercially available), ES-MS m/e: 546.8 (M+H$^+$).

Example 60

6-{(RS)-1-[(3SR,4RS)-4-(3,4-Dichloro-phenyl)-1-(4-methanesulfonyl-piperazine-1-carbonyl)-pyrrolidin-3-yl]-ethoxy}-3-nicotinonitrile

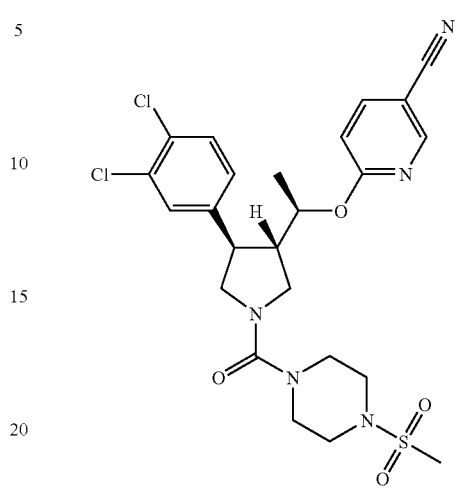

Mitsunobu Reaction According to General Procedure III:

Pyrrolidine intermediate: [(3RS,4SR)-3-(3,4-Dichloro-phenyl)-4-((SR)-1-hydroxy-ethyl)-pyrrolidin-1-yl]-(4-methanesulfonyl-piperazin-1-yl)-methanone (XII-B-1), Pyridinol: 6-Hydroxy-nicotinonitrile (commercially available), ES-MS m/e: 551.7 (M+H$^+$).

Example 61

[(3SR,4RS)-3-[(RS)-1-(5-Chloro-pyridin-2-yloxy)-ethyl]-4-(3,4-dichloro-phenyl)-pyrrolidin-1-yl]-(2-oxa-6-aza-spiro[3.3]hept-6-yl)-methanone

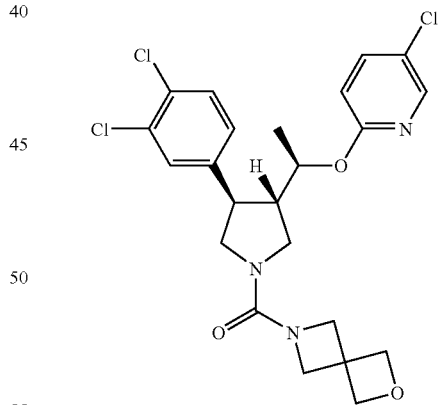

a) 3SR,4RS)-3-[(RS)-1-(5-Chloro-pyridin-2-yloxy)-ethyl]-4-(3,4-dichloro-phenyl)-pyrrolidine-1-carbonyl chloride To a stirred solution of carbonic acid ditrichloromethyl ester (triphosgene) (48 mg, 0.16 mmol) in CH$_2$Cl$_2$ (10 mL) at −78° C., was added a solution of 5-chloro-2-{(RS)-1-[(3SR, 4RS)-4-(3,4-dichloro-phenyl)-pyrrolidin-3-yl]-ethoxy}-pyridine (intermediate XV-B-2) (150 mg, 0.40 mmol) and pyridine (0.072 mL, 0.88 mmol) in CH$_2$Cl$_2$ (5 mL) over 30 minutes. The temperature was raised to RT, and stirring was continued over night. The organic phase was washed with H₂O, dried over Na₂SO₄. Concentration under vacuo yielded and column chromatography (SiO2, EtOAc/H, 1:1) yielded 90 mg (50%) of the title compound as a viscous colorless oil.

b) [(3SR,4RS)-3-[(RS)-1-(5-Chloro-pyridin-2-yloxy)-ethyl]-4-(3,4-chloro-phenyl)-pyrolidin-1-yl]-(2-oxa-6-aza-spiro[3.3]hept-6-yl)-methanone To a stirred solution of (3SR,4RS)-3-[(RS)-1-(5-chloro-pyridin-2-yloxy)-ethyl]-4-(3,4-dichloro-phenyl)-pyrrolidine-1-carbonyl chloride (22 mg, 0.051 mmol) in CH₂Cl₂ (3 mL) were added Et₃N (0.022 mL, 0.16 mmol) aid 2-oxa-6-aza-spiro[3.3]heptane (6 mg, 0.060 mmol). Stirring was continued overnight, and the reaction mixture was concentrated under vacuo and directly purified by flash chromatography (SiO₂, EtOAc) to yield 7 mg (28%) the title compound as light yellow oil. ES-MS m/e: 497.1 (M+H⁺).

Example 62

2-[(3SR,4RS)-3-[(RS)-1-(5-Chloro-pyridin-2-yloxy)-ethyl]-4-(3,4-dichloro-phenyl)-pyrrolidine-1-carbonyl]-hexahydro-pyrrolo[1,2-a]pyrazin-6-one

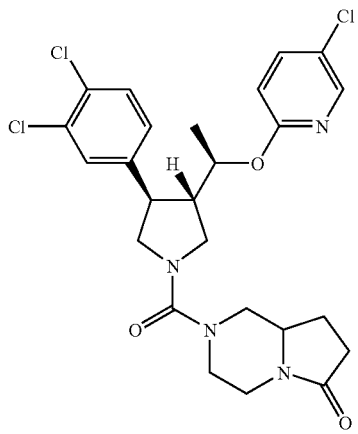

a) (3SR,4RS)-3-[(RS)-1-(5-Chloro-pyridin-2-yloxy)-ethyl]-4-(3,4-dichloro-phenyl)-pyrrolidine-1-carbonyl chloride To a stirred solution of carbonic acid ditrichloromethyl ester (triphosgene) (48 mg, 0.16 mmol) in CH₂Cl₂ (10 mL) at −78° C., was added a solution of 5-chloro-2-{(RS)-1-[(3SR,4RS)-4-(3,4-dichloro-phenyl)-pyrrolidin-3-yl]-ethoxy}-pyridine (intermediate XV-B-2) (150 mg, 0.40 mmol) and pyridine (0.072 mL, 0.88 mmol) in CH₂Cl₂ (5 ML) over 30 minutes. The temperature was raised to RT, and stirring was continued over night. The organic phase was washed with H₂O, dried over Na₂SO₄. Concentration under vacuo yielded and column chromatography (SiO₂, EtOAc/H, 1:1) yielded 90 mg (50%) of the title compound as a viscous colorless oil.

b) 2-[(3SR,4RS)-3-[(RS)-1-(5-Chloro-pyridin-2-yloxy)-ethyl]-4-(3,4-dichloro-phenyl)-pyrrolidine-1-carbonyl]-hexahydro-pyrrolo[1,2-a]pyrazin-6-one To a stirred solution of (3SR,4RS)-3-[(RS)-1-(5-chloro-pyridin-2-yloxy)-ethyl]-4-(3,4-dichloro-phenyl)-pyrrolidine-1-carbonyl chloride (22 mg, 0.051 mmol) in CH₂Cl₂ (3 mL) were added Et₃N (0.015 ml, 0.11 mmol) and hexahydro-pyrrolo[1,2-a]pyrazin-6-one (commercially available) (9 mg, 0.064 mmol). Stirring was continued overnight, and the reaction mixture was concentrated under vacuo and directly purified by flash chromatography (SiO₂, EtOAc) to yield 7 mg (25%) the title compound as light yellow oil. ES-MS m/e: 539.2 (M+H⁺).

Example 63

[(3SR,4RS)-3-(5-Chloro-pyridin-2-yloxymethyl-4-(3,4-dichloro-phenyl)-pyrrolidin-1-yl]-(4-methane-sulfonyl-piperazin-1-yl)-methanone

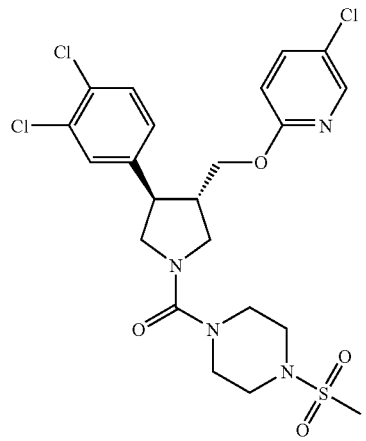

Mitsunobu Reaction According to General Procedure III:

Pyrrolidine intermediate: [(3RS,4SR)-3-(3,4-Dichloro-phenyl)-4-hydroxymethyl-pyrrolidin-1-yl]-(4-methane-sulfonyl-piperazin-1-yl)-methanone (VII-1), Phenol: 5-Chloro-pyridin-2-ol (commercially available),
ES-MS m/e, 549.2 (M+H⁺).

Example 64

N-(1-{2-[(3SR,4RS)-3-[(RS)-1-(4-Chloro-phenoxy)-ethyl]-4-(3,4-dichloro-phenyl)-pyrrolidin-1-yl]-2-oxo-ethyl}-4-phenyl-piperidin-4-yl)-acetamide

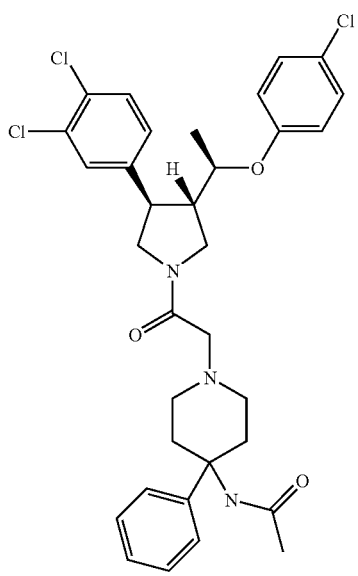

Coupling Reaction According to General Procedure IV:
Pyrrolidine intermediate: 2-Bromo-1-[(3SR,4RS)-3-[(RS)-1-(5-chloro-pyridin-2-yloxy)-ethyl]-4-(3,4-dichloro-phenyl)-pyrrolidin-1-yl]-ethanone (XVI-B-2),
Amine: N-(4-Phenyl-piperidin-4-yl)-acetamide (commercially available),
ES-MS m/e: 630.9 (M+H$^+$).

Example 65

N-(1-{2-[(3SR,4RS)-[3-(RS)-1-(4-Chloro-phenoxy)-ethyl]-4-(3,4-dichloro-phenyl)-pyrrolidin-1-yl]-2-oxo-ethyl}-piperidin-4-yl)-N-methyl-acetamide

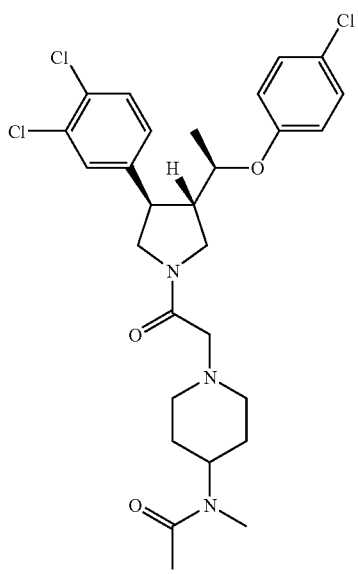

Coupling Reaction According to General Procedure IV:
Pyrrolidine intermediate: 2-Bromo-1-[(3SR,4RS)-3-[(RS)-1-(5-chloro-pyridin-2-yloxy)-ethyl]-4-(3,4-dichloro-phenyl)-pyrrolidin-1-yl)]-ethanone (XVI-B-2), Amine: N-Methyl-N-piperidin-4-yl-acetamide (commercially available),
ES-MS m/e: 568.7 (M+H$^+$).

Example 66

2-(4-Acetyl-piperazin-1-yl)-1-[(3SR,4RS)-3-[(RS)-1-(4-chloro-phenoxy)-ethyl]-4-(3,4-dichloro-phenyl)-pyrrolidin-1-yl]-ethanone

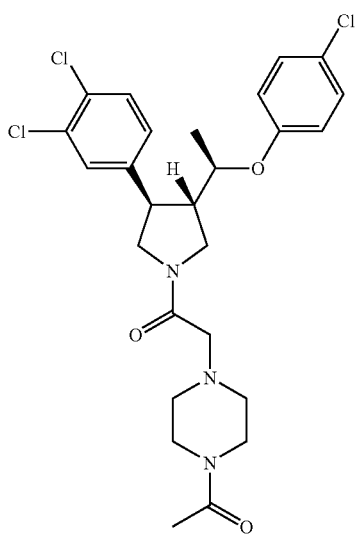

Coupling Reaction According to General Procedure IV:
Pyrrolidine intermediate: 2-Bromo-1-[(3SR,4RS)-3-[(RS)-1-(5-chloro-pyridin-2-yloxy)-ethyl]-4-(3,4-dichloro-phenyl)-pyrrolidin-1-yl]-ethanone (XVI-B-2),
Amine: 1-piperazin-1-yl-ethanone (commercially available),
ES-MS m/e 538.8 (M+H$^+$).

Example 67

1-[(3SR,4RS)-3-[(RS)-1-(4-Chloro-phenoxy)-ethyl]-4-(3,4-dichloro-phenyl)-pyrrolidin-1-yl]-2-(4-hydroxymethyl-piperidin-1-yl)-ethanone

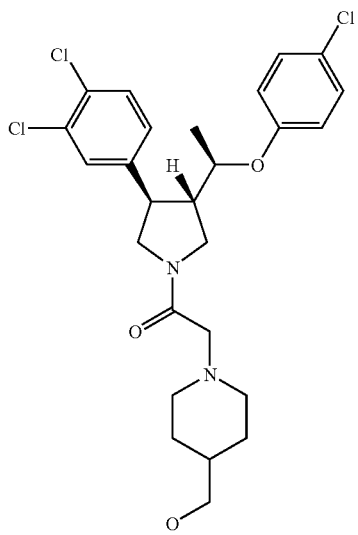

Coupling Reaction According to General Procedure IV:

Pyrrolidine intermediate: 2-Bromo-1-[(3SR,4RS)-3-[(RS)-1-(5-chloro-pyridin-2-yloxy)-ethyl]-4-(3,4-dichloro-phenyl)-pyrrolidin-1-yl]-ethanone (XVI-B-2), Amine: Piperidin-4-yl-methanol (commercially available), ES-MS m/e: 527.6 (M+H⁺).

Example 68

1-[(3S,4R)-3-[(R)-1-(5-Chloro-pyridin-2-yloxy)-ethyl]-4-(3,4-dichloro-phenyl)-pyrrolidin-1-yl]-2-(2-oxa-5-aza-bicyclo[2.2.1]hept-5-yl)-ethanone

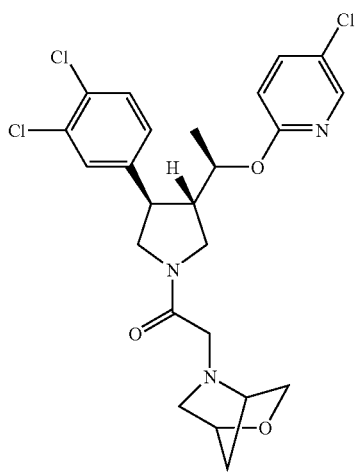

Coupling Reaction According to General Procedure IV:

Pyrrolidine intermediate: 2-Bromo-1-[(3SR,4RS)-3-[(RS)-1-(5-chloro-pyridin-2-yloxy)-ethyl]-4-(3,4-dichloro-phenyl)-pyrrolidin-1-yl]-ethanone (XVI-B-2), Amine: 2-Oxa-5-aza-bicyclo[2.2.1]heptane (commercially available), ES-MS m/e: 512.0 (M+H⁺).

Example 69

{(3SR,4RS)-3-(3,4-Dichloro-phenyl)-4-[(SR)-1-(5-trifluoromethyl-pyridin-2-yloxy)ethyl]-pyrrolidin-1-yl}-(4-methanesulfonyl-piperazin-1-yl)-methanone

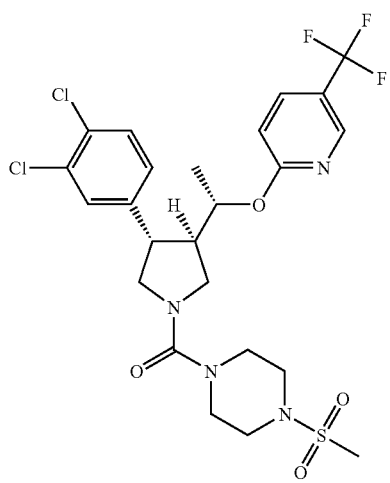

Coupling Reaction According to General Procedure II:

Pyrrolidine intermediate: 2-{(SR)-1-[(3RS,4SR)-4-(3,4-Dichloro-phenyl)-pyrrolidin-3-yl]-ethoxy}-5-trifluoromethyl-pyridine (XV-B-3), Carbamoyl chloride: 4-Methanesulfonyl-piperazine-1-carbonyl chloride (described herein above), ES-MS m/e: 595.2 (M+H⁺).

Example 70

6-{(SR)-1-[(3RS,4SR)-1-[2-(4-Cyano-piperidin-1-yl)-acetyl]-4-(3,4-dichloro-phenyl)-pyrrolidin-3-yl]-ethoxy}-nicotinonitrile

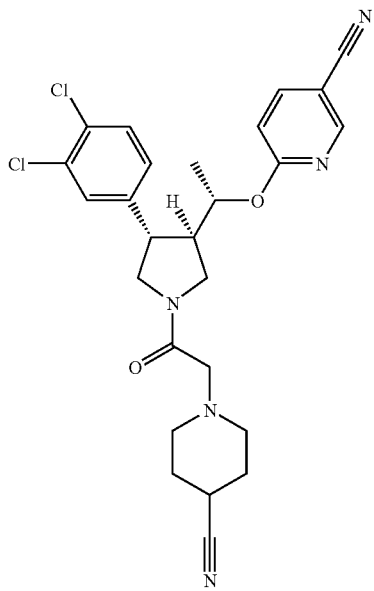

Coupling Reaction According to General Procedure IV:

Pyrrolidine intermediate: 6-{(SR)-1-[(3RS,4SR)-1-(2-Bromo-acetyl)-4-(3,4-dichloro-phenyl)-pyrrolidin-3-yl]-ethoxy-}nicotinonitrile (XVI-B-4), Amine: Piperidine-4-carbonitrile (commercially available), ES-MS m/e: 512.0 (M+H$^+$).

Example 71

6-{((SR)-1-[(3RS,4SR)-1-(4-Cyano-piperidine-1-carbonyl)-4-(3,4-dichloro-phenyl)-pyrrolidin-3-yl-]ethoxy}-nicotinonitrile

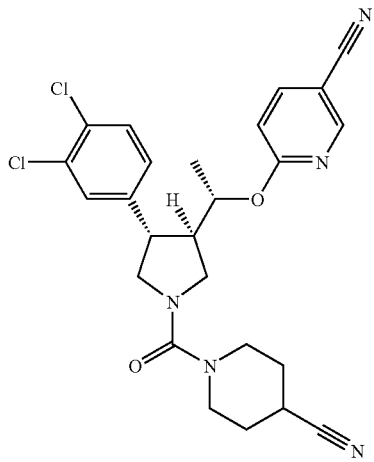

a) (3RS,4SR)-3-[(SR)-1-(5-Cyano-pyridin-2-yloxy)-ethyl]-4-(3,4-dichloro-phenyl)-pyrrolidine-1-carbonyl chloride To a stirred solution of carbonic acid ditrichloromethyl ester (triphosgene) (67 mg, 0.22 mmol) in CH$_2$Cl$_2$ (14 ml) at −78° C., was added a solution of 6-{(SR)-1-[(3RS,4SR)-4-(3,4-dichloro-phenyl)-pyrrolidin-3-yl]-ethoxy}-nicotinonitrile (intermediate XV-B-4) (210 mg, 0.56 mmol) and pyridine (0.10 ml, 1.23 mmol) in CH$_2$Cl$_2$ (7 mL) over 30 minutes. The temperature was raised to RT, and stirring was continued over night. The organic phase was washed with H$_2$O, dried over Na$_2$SO$_4$. Concentration under vacuo yielded and column chromatography (SiO2, EtOAc/H, 1:1) yielded 144 mg (57%) of the title compound as a viscous colorless oil.

b) 6-{(SR)-1-[(3RS,4SR)-1-(4-Cyano-piperidine-1-carbonyl)-4-(3,4-dichloro-phenyl)-pyrrolidin-3-yl]-ethoxy}-nicotinonitrile To a stirred solution of (3RS,4SR)-3-[(SR)-1-(5-Cyano-pyridin-2-yloxy)-ethyl]-4-(3,4-dichloro-phenyl)-pyrrolidine-1-carbonyl chloride (30 mg, 0.070 mmol) in CH$_2$Cl$_2$ (4 mL) were added Et$_3$N (0.015 mL, 0.11 mmol) and piperidine-4-carbonitrile (commercially available) (9 mg, 0.084 mmol). Stirring was continued overnight, and the reaction mixture was concentrated under vacuo and directly purified by flash chromatography (SiO$_2$, EtOAc) to yield 24 mg (69%) the title compound as light yellow oil. ES-MS m/e: 498.0 (M+H$^+$).

Example 72

(3SR,4RS)-3-(3,4-Dichloro-phenyl)-4-[(SR)-1-(5-trifluoromethyl-pyridin-2-yloxy)-ethyl]-pyrrolidine-1-carboxylic acid (3-methyl-3H-imidazol-4-ylmethyl)-amide (not encompassed by formula I)

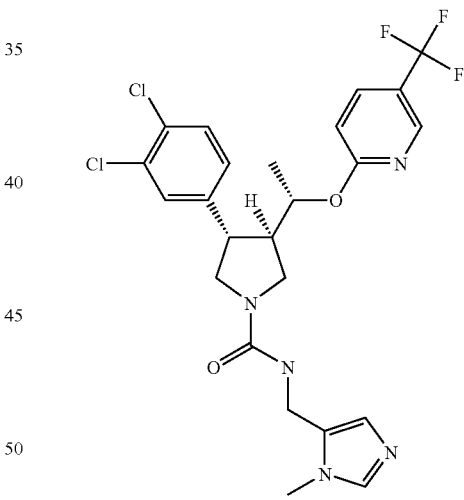

a) (3SR,4RS)-3-(3,4-Dichloro-phenyl)-4-[(SR)-1-(5-trifluoromethyl-pyridin-2-yloxy)-ethyl]-pyrrolidine-1-carbonyl chloride To a stirred solution of carbonic acid ditrichloromethyl ester (triphosgene) (22 mg 0.074 mmol) in CH$_2$Cl$_2$ (3 mL) at −78° C., was added a solution of 2-{(SR)-1-[(3RS,4SR)-4-(3,4-dichloro-phenyl)pyrrolidin-3-yl]-ethoxy}-5-trifluoromethyl-pyridine (intermediate XV-B-3) (76 mg, 0.19 mmol) and pyridine (0.03 mL, 0.42 mmol) in CH$_2$Cl$_2$ (1 mL) over 30 minutes. The temperature was raised to RT, and stirring was continued over night. The organic phase was washed with H$_2$O, dried over Na$_2$SO$_4$. Concentration under vacuo yielded and column chromatography (SiO2, EtOAc/H, 1:4) yielded 36 mg (41%) of the title compound as a viscous colorless oil.

b) (3SR,4RS)-3-(3,4-Dichloro-phenyl)-4-[(SR)-1-(5-trifluoromethyl-pyridin-2-yloxy)-ethyl]-pyrrolidine-1-carboxylic acid (3-methyl-3H-imidazol-4-ylmethyl)-amide To a stirred solution of (3SR,4RS)-3-(3,4-dichloro-phenyl)-4-[(SR)-1-(5-trifluoromethyl-pyridin-2-yloxy)-ethyl]-pyrrolidine-1-carbonyl chloride (30 mg, 0.064 mmol) in CH$_2$Cl$_2$ (3 mL) were added Et$_3$N (0.015 mL, 0.11 mmol) and C-(3-Methyl-3H-imidazol-4-yl)-methylamine (commercially available) (8 mg, 0.070 mmol). Stirring was continued overnight, and the reaction mixture was concentrated under vacuo and directly purified by flash chromatography (SiO$_2$, CH$_2$Cl$_2$/MeOH 98/2) to yield 14 mg (40%) the title compound as a white solid. ES-MS m/e: 542.2 (M+H$^+$).

Example 73

{(3SR,4RS)-3-(3,4-Dichloro-phenyl)-4-[(SR)-1-(5-trifluoromethyl-pyridin-2-yloxy)-ethyl]-pyrrolidin-1-yl}-(2-oxa-5-aza-bicyclo[2.2.1]hept-5-yl)-methanone

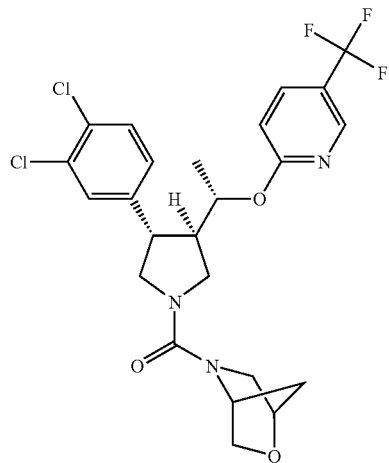

a) (3SR,4RS)-3-(3,4-Dichloro-phenyl)-4-[(SR)-1-(5-trifluoromethyl-pyridin-2-yloxy)-ethyl]-pyrrolidine-1-carbonyl chloride To a stirred solution of carbonic acid ditrichloromethyl ester (triphosgene) (22 mg, 0.074 mmol) in CH$_2$Cl$_2$ (3 mL) at −78° C., was added a solution of 2-{(SR)-1-[(3RS,4SR)-4-(3,4-dichloro-phenyl)-pyrrolidin-3-yl]-ethoxy}-5-trifluoromethyl-pyridine-(intermediate XV-B-3) (76 mg, 0.19 mmol) and pyridine (0.03 mL 0.42 mmol) in CH$_2$Cl$_2$ (1 mL) over 30 minutes. The temperature was raised to RT, and stirring was continued over night. The organic phase was washed with H$_2$O, dried over Na$_2$SO$_4$. Concentration under vacuo yielded and column chromatography (SiO$_2$, EtOAc/H, 1:4) yielded 36 mg (41%) of the title compound as a viscous colorless oil.

b) {(3SR,4RS)-3-(3,4-Dichloro-phenyl)-4-[(SR)-1-(5-trifluoromethyl-pyridin-2-yloxy)-ethyl]-pyrrolidin-1-yl}-(2-oxa-5-aza-bicyclo[2.2.1]hept-5-yl)-methanone To a stirred solution of (3SR,4RS)-3-(3,4-dichloro-phenyl)-4-[(SR)-1-(5-trifluoromethyl-pyridin-2-yloxy)-ethyl]-pyrrolidine-1-carbonyl chloride (30 mg, 0.064 mmol) in CH$_2$Cl$_2$ (3 mL) were added Et$_3$N (0.015 mL, 0.11 mmol) and 2-Oxa-5-aza-bicyclo[2.2.1]heptane (commercially available) (7 mg, 0.070 mmol). Stirring was continued overnight, and the reaction mixture was concentrated under vacuo and directly purified by flash chromatography (SiO$_2$, EtOAc) to yield 27 mg the title compound as a white solid. ES-MS m/e: 530.1 (M+H$^+$).

The invention claimed is:

1. A compound of formula I

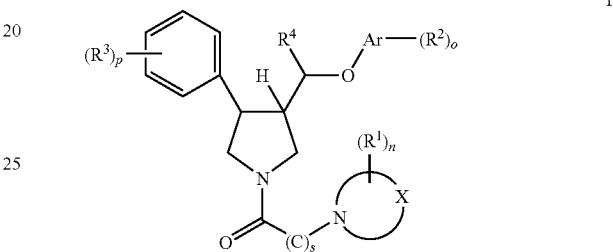

wherein

Ar is aryl or a five or six membered heteroaryl selected from the group consisting of quinoxalinyl, pyrazinyl, pyrazolyl, pyridinyl, pyridyl, pyrimidinyl, oxadiazolyl, triazolyl, tetrazolyl, thiazolyl, thiadiazolyl, thiophenyl, isoxazolyl, pyrrolyl, furanyl or imidazolyl;

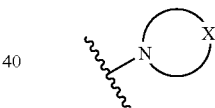

is a six membered mono heterocyclic group, wherein X is a carbon atom, SO$_2$ or a further hetero atom, selected from the group consisting of N and O;

if X is a carbon atom, O, SO$_2$ or unsubstituted N, then
R$^1$ is hydrogen, hydroxy, cyano, —(CH$_2$)$_q$—OH, —(CH$_2$)$_q$—NRR', —(CH$_2$)q-CN, lower alkyl, —S(O)$_2$-lower alkyl, —NR—S(O)$_2$-lower alkyl, —C(O)-lower alkyl, —NR—C(O)-lower alkyl, phenyl, or a piperidinyl-2-one;

if X is a N-atom, substituted by R$^1$, then
R$^1$ is hydrogen, —(CH$_2$)$_q$—OH, —(CH$_2$)$_q$—NRR', —(CH$_2$)q-CN, lower alkyl, —S(O)$_2$-lower alkyl, aryl, or a five or six membered heteroaryl or —C(O)-lower alkyl provided that q is 2 or 3;

R and R' are each independently hydrogen or lower alkyl;
R$^2$ is hydrogen, halogen, lower alkyl, cyano, lower alkoxy substituted by halogen, lower alkyl substituted by halogen or is a five or six membered heteroaryl;
R$^3$ is hydrogen or halogen;
R$^4$ is hydrogen or lower alkyl;
n is 1 or 2; in case n is 2, R$^1$ may be the same or different;
o is 1 or 2; in case o is 2, R$^2$ may be the same or different;
p is 1 or 2; in case p is 2, R$^3$ may be the same or different;
q is 1, 2 or 3; and s is 0, 1, 2, 3 or 4 wherein (C)$_s$ is additionally bonded to hydrogen atoms;
or a pharmaceutically active salt thereof, including all stereoisomeric forms, individual diastereoisomers and enantiomers of the compound of formula (I) as well as racemic and non-racemic mixtures thereof.

2. The compound of claim 1, wherein (R$^3$)$_p$ is 3,4-dichloro.

3. The compound of claim 2, wherein

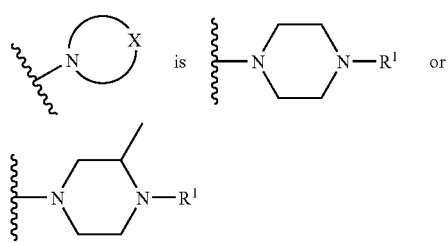

and Ar is phenyl.

4. The compound of claim 3, selected from the group consisting of
- {(3RS,4SR)-3-(3,4-dichloro-phenyl)-4-[(RS)-1-(4-trifluoromethyl-phenoxy)-ethyl]-pyrrolidin-1-yl}-(4-methanesulfonyl-piperazin-1-yl)-methanone,
- {(3RS,4SR)-3-(3,4-dichloro-phenyl)-4-[(SR)-1-(4-trifluoromethyl-phenoxy)-ethyl]-pyrrolidin-1-yl}-(4-methanesulfonyl-piperazin-1-yl)-methanone,
- 2-(4-acetyl-piperazin-1-yl)-1-{(3RS,4SR)-3-(3,4-dichloro-phenyl)-4-[(RS)-1-(4-trifluoromethyl-phenoxy)-ethyl]-pyrrolidin-1-yl}-ethanone,
- (3RS,4SR)-3-(3,4-dichloro-phenyl)-4-[(RS)-1-(4-trifluoromethyl-phenoxy)-ethyl]-pyrrolidin-1-yl}-((R)-4-methanesulfonyl-3-methyl-piperazin-1-yl)-methanone,
- [(3SR,4RS)-3-[(RS)-1-(3,4-dichloro-phenoxy)-ethyl]-4-(3,4-dichloro-phenyl)-pyrrolidin-1-yl]-(4-methanesulfonyl-piperazin-1-yl)-methanone,
- [(3RS,4SR)-3-(3,4-dichloro-phenyl)-4-((RS)-1-p-tolyloxy-ethyl)-pyrrolidin-1-yl]-(4-methanesulfonyl-piperazin-1-yl)-methanone,
- 4-{(RS)-1-[(3SR,4RS)-4-(3,4-dichloro-phenyl)-1-(4-methanesulfonyl-piperazine-1-carbonyl)-pyrrolidin-3-yl]-ethoxy}-benzonitrile,
- {(3RS,4SR)-3-(3,4-dichloro-phenyl)-4-[(RS)-1-(4-fluoro-phenoxy)-ethyl]-pyrrolidin-1-yl}-(4-methanesulfonyl-piperazin-1-yl)-methanone,
- [(3SR,4RS)-3-[(RS)-1-(4-chloro-phenoxy)-ethyl]-4-(3,4-dichloro-phenyl)-pyrrolidin-1-yl]-(4-methanesulfonyl-piperazin-1-yl)-methanone,
- [(3SR,4RS)-3-[(RS)-1-(3-chloro-4-fluoro-phenoxy)-ethyl]-4-(3,4-dichloro-phenyl)-pyrrolidin-1-yl]-(4-methanesulfonyl-piperazin-1-yl)-methanone,
- 4-{(SR)-1-[(3SR,4RS)-4-(3,4-dichloro-phenyl)-1-(4-methanesulfonyl-piperazine-1-carbonyl)-pyrrolidin-3-yl]-ethoxy}-benzonitrile,
- {(3RS,4SR)-3-(3,4-dichloro-phenyl)-4-[(SR)-1-(4-fluoro-phenoxy)-ethyl]-pyrrolidin-1-yl}-(4-methanesulfonyl-piperazin-1-yl)-methanone,
- [(3SR,4RS)-3-[(SR)-1-(4-chloro-phenoxy)-ethyl]-4-(3,4-dichloro-phenyl)-pyrrolidin-1-yl]-(4-methanesulfonyl-piperazin-1-yl)-methanone,
- {(3RS,4SR)-3-(3,4-dichloro-phenyl)-4-[(RS)-1-(4-trifluoromethyl-phenoxy)-ethyl]-pyrrolidin-1-yl}-(4-(2-dimethylamino-ethyl)-piperazin-1-yl)-methanone, and
- 2-(4-acetyl-piperazin-1-yl)-1-[(3SR,4RS)-3-[(RS)-1-(4-chloro-phenoxy)-ethyl]-4-(3,4-dichloro-phenyl)-pyrrolidin-1-yl]-ethanone.

5. The compound of claim 2, wherein

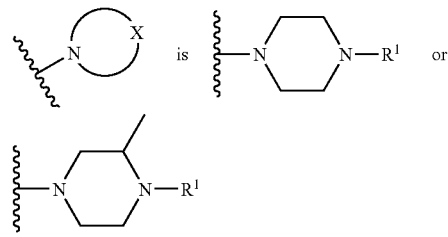

and Ar is pyridyl.

6. The compound of claim 5, are selected from the group consisting of
- [(3SR,4RS)-3-[(RS)-1-(5-chloro-pyridin-2-yloxy)-ethyl]-4-(3,4-dichloro-phenyl)-pyrrolidin-1-yl]-(4-methanesulfonyl-piperazin-1-yl)-methanone,
- [(3SR,4RS)-3-[(RS)-1-(5-chloro-pyridin-2-yloxy)-ethyl]-4-(3,4-dichloro-phenyl)-pyrrolidin-1-yl](R)-4-methanesulfonyl-3-methyl-piperazin-1-yl)-methanone,
- [(3SR,4RS)-3-[(RS)-1-(5-chloro-pyridin-2-yloxy)-ethyl]-4-(3,4-dichloro-phenyl)-pyrrolidin-1-yl]-[4-(2-dimethylamino-ethyl)-piperazin-1-yl]-methanone,
- {(3RS,4SR)-3-(3,4-dichloro-phenyl)-4-[(SR)-1-(5-fluoro-pyridin-2-yloxy)-ethyl]-pyrrolidin-1-yl}-(4-methanesulfonyl-piperazin-1-yl)-methanone,
- {(3RS,4SR)-3-(3,4-dichloro-phenyl)-4-[(RS)-1-(5-fluoro-pyridin-2-yloxy)-ethyl]-pyrrolidin-1-yl}-(4-methanesulfonyl-piperazin-1-yl)-methanone,
- [(3SR,4RS)-3-(5-chloro-pyridin-2-yloxymethyl)-4-(3,4-dichloro-phenyl)-pyrrolidin-1-yl]-(4-methanesulfonyl-piperazin-1-yl)-methanone, and
- {(3SR,4RS)-3-(3,4-dichloro-phenyl)-4-[(SR)-1-(5-trifluoromethyl-pyridin-2-yloxy)-ethyl]-pyrrolidin-1-yl}-(4-methanesulfonyl-piperazin-1-yl)-methanone.

7. The compound of claim 2, wherein

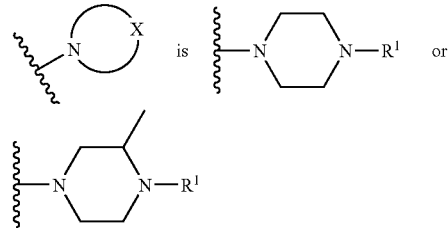

and Ar is pyrimidinyl.

8. The compound of claim 7, selected from the group consisting of
- {(3RS,4SR)-3-(3,4-dichloro-phenyl)-4-[(RS)-1-(pyrimidin-2-yloxy)-ethyl]-pyrrolidin-1-yl}-(4-methanesulfonyl-piperazin-1-yl)-methanone,
- {(3RS,4SR)-3-(3,4-dichloro-phenyl)-4-[(RS)-1-(5-fluoro-pyrimidin-2-yloxy)-ethyl]-pyrrolidin-1-yl}-(4-methanesulfonyl-piperazin-1-yl)-methanone, and
- [(3SR,4RS)-3-[(RS)-1-(5-chloro-pyrimidin-2-yloxy)-ethyl]-4-(3,4-dichloro-phenyl)-pyrrolidin-1-yl]-(4-methanesulfonyl-piperazin-1-yl)-methanone.

9. The compound of claim 2, wherein

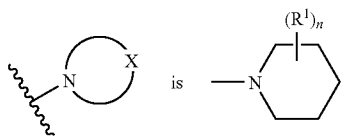

and Ar is phenyl.

10. The compound of claim 9, selected from the group consisting of
- N-(1-{(3RS,4SR)-3-(3,4-dichloro-phenyl)-4-[(RS)-1-(4-trifluoromethyl-phenoxy)-ethyl]-pyrrolidine-1-carbonyl}-piperidin-4-yl)-N-methyl-methanesulfonamide,
- N-[1-(2-{(3RS,4SR)-3-(3,4-dichloro-phenyl)-4-[(RS)-1-(4-trifluoromethyl-phenoxy)-ethyl]-pyrrolidin-1-yl}-2-oxo-ethyl)-piperidin-4-yl]-N-methyl-methanesulfonamide,
- N-[1-(2-{(3RS,4SR)-3-(3,4-dichloro-phenyl)-4-[(RS)-1-(4-trifluoromethyl-phenoxy)-ethyl]-pyrrolidin-1-yl}-2-oxo-ethyl)-piperidin-4-yl]-acetamide,
- N-(1-{2-[(3SR,4RS)-3-[(RS)-1-(4-chloro-phenoxy)-ethyl]-4-(3,4-dichloro-phenyl)-pyrrolidin-1-yl]-2-oxo-ethyl}-4-phenyl-piperidin-4-yl)-acetamide,
- N-(1-{2-[(3SR,4RS)-3-[(RS)-1-(4-chloro-phenoxy)-ethyl]-4-(3,4-dichloro-phenyl)-pyrrolidin-1-yl]-2-oxo-ethyl}-piperidin-4-yl)-N-methyl-acetamide, and
- 1-[(3SR,4RS)-3-[(RS)-1-(4-chloro-phenoxy)-ethyl]-4-(3,4-dichloro-phenyl)-pyrrolidin-1-yl]-2-(4-hydroxymethyl-piperidin-1-yl)-ethanone.

11. The compound of claim 2, wherein

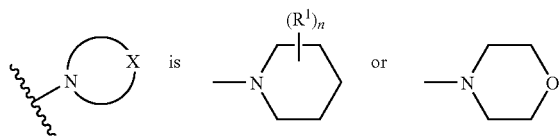

and Ar is pyridyl.

12. The compound of claim 11, selected from the group consisting of
- 1-[(3SR,4RS)-3-[(RS)-1-(5-chloro-pyridin-2-yloxy)-ethyl]-4-(3,4-dichloro-phenyl)-pyrrolidin-1-yl]-5-morpholin-4-yl-pentan-1-one,
- 6-{(SR)-1-[(3RS,4SR)-1-[2-(4-cyano-piperidin-1-yl)-acetyl]-4-(3,4-dichloro-phenyl)-pyrrolidin-3-yl]-ethoxy}-nicotinonitrile, and
- 6-{(SR)-1-[(3RS,4SR)-1-(4-cyano-piperidine-1-carbonyl)-4-(3,4-dichloro-phenyl)-pyrrolidin-3-yl]-ethoxy}-nicotinonitrile.

13. A compound of formula I,

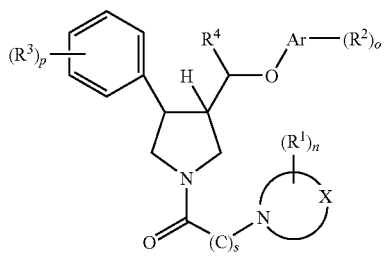

wherein

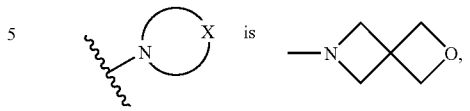

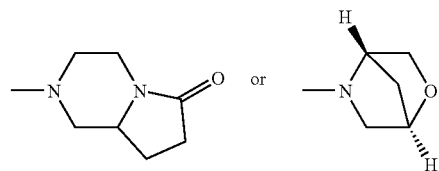

and Ar is pyridyl;

if X is a carbon atom, O, SO$_2$ or unsubstituted N, then
R$^1$ is hydrogen, hydroxy, cyano, —(CH$_2$)$_q$—OH, —(CH$_2$)$_q$—NRR', —(CH$_2$)q-CN, lower alkyl, —S(O)$_2$-lower alkyl, —NR—S(O)$_2$-lower alkyl, —C(O)-lower alkyl, —NR—C(O)-lower alkyl, phenyl, or piperidinyl-2-one;

if X is a N-atom, substituted by R$^1$, then
R$^1$ is hydrogen, —(CH$_2$)$_q$—OH, (CH$_2$)$_q$—NRR', —(CH$_2$)q-CN, lower alkyl, —S(O)$_2$-lower alkyl, aryl, or a five or six membered heteroaryl or —C(O)-lower alkyl provided that q is 2 or 3;

R and R' are each independently hydrogen or lower alkyl;

R$^2$ is hydrogen, halogen, lower alkyl, cyano, lower alkoxy substituted by halogen, lower alkyl substituted by halogen or is a five or six membered heteroaryl;

R$^3$ is hydrogen or halogen;

R$^4$ is hydrogen or lower alkyl;

n is 1 or 2; in case n is 2, R$^1$ may be the same or different;

o is 1 or 2; in case o is 2, R$^2$ may be the same or different;

p is 1 or 2; in case p is 2, R$^3$ may be the same or different;

q is 1, 2 or 3; and s is 0, 1, 2, 3 or 4;

or a pharmaceutically active salt thereof, including all stereoisomeric forms, individual diastereoisomers and enantiomers of the compound of formula (I) as well as racemic and non-racemic mixtures thereof.

14. The compound of claim 13, selected from the groups consisting of
- [(3SR,4RS)-3-[(RS)-1-(5-chloro-pyridin-2-yloxy)-ethyl]-4-(3,4-dichloro-phenyl)-pyrrolidin-1-yl]-(2-oxa-6-aza-spiro[3.3]hept-6-yl)-methanone,
- 2-[(3SR,4RS)-3-[(RS)-1-(5-chloro-pyridin-2-yloxy)-ethyl]-4-(3,4-dichloro-phenyl)-pyrrolidine-1-carbonyl]-hexahydro-pyrrolo[1,2-a]pyrazin-6-one,
- 1-[(3S,4R)-3-[(R)-1-(5-chloro-pyridin-2-yloxy)-ethyl]-4-(3,4-dichloro-phenyl)-pyrrolidin-1-yl]-2-(2-oxa-5-aza-bicyclo[2.2.1]hept-5-yl)-ethanone, and
- {(3SR,4RS)-3-(3,4-dichloro-phenyl)-4-[(SR)-1-(5-trifluoromethyl-pyridin-2-yloxy)-ethyl]-pyrrolidin-1-yl}-(2-oxa-5-aza-bicyclo[2.2.1]hept-5-yl)-methanone.

15. A pharmaceutical composition comprising a therapeutically effective amount of a compound of formula I

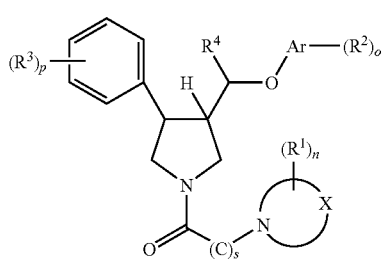

wherein
Ar is aryl or a five or six membered heteroaryl selected from the group consisting of quinoxalinyl, pyrazinyl, pyrazolyl, pyridinyl, pyridyl, pyrimidinyl, oxadiazolyl, triazolyl, tetrazolyl, thiazolyl, thiadiazolyl, thiophenyl, isoxazolyl, pyrrolyl, furanyl or imidazolyl wherein $(C)_s$ is additionally bonded to hydrogen atoms;

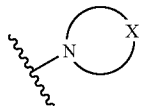

is a six membered mono heterocyclic group, wherein X is a carbon atom, $SO_2$ or a further hetero atom, selected from the group consisting of N and O;
if X is a carbon atom, O, $SO_2$ or unsubstituted N, then
$R^1$ is hydrogen, hydroxy, cyano, —$(CH_2)_q$—OH, —$(CH_2)_q$—NRR', —$(CH_2)_q$—CN, lower alkyl, —$S(O)_2$-lower alkyl, —NR—$S(O)_2$-lower alkyl, —C(O)-lower alkyl, —NR—C(O)-lower alkyl, phenyl, or a piperidinyl-2-one;
if X is a N-atom, substituted by $R^1$, then
$R^1$ is hydrogen, —$(CH_2)_q$—OH, —$(CH_2)_q$—NRR', —$(CH_2)_q$—CN, lower alkyl, —$S(O)_2$-lower alkyl, aryl, or a five or six membered heteroaryl or —C(O)-lower alkyl provided that q is 2 or 3,
R and R' are each independently hydrogen or lower alkyl;
$R^2$ is hydrogen, halogen, lower alkyl, cyano, lower alkoxy substituted by halogen, lower alkyl substituted by halogen or is a five or six membered heteroaryl;
$R^3$ is hydrogen or halogen;
$R^4$ is hydrogen or lower alkyl;
n is 1 or 2; in case n is 2, $R^1$ may be the same or different;
o is 1 or 2; in case o is 2, $R^2$ may be the same or different;
P is 1 or 2; in case p is 2, $R^3$ may be the same or different;
q is 1, 2 or 3; and
s is 0, 1, 2, 3 or 4 wherein $(C)_s$ is additionally bonded to hydrogen atoms;
or a pharmaceutically active salt thereof, including all stereoisomeric forms, individual diastereoisomers and enantiomers of the compound of formula (I) as well as racemic and non-racemic mixtures thereof and a pharmaceutically acceptable carrier.

16. A pharmaceutical composition comprising a therapeutically effective amount of a compound of formula I

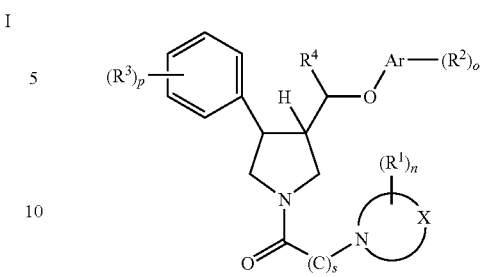

wherein

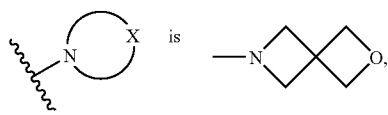

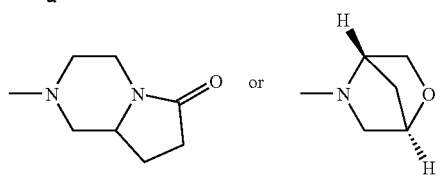

and Ar is pyridyl;
if X is a carbon atom, O, $SO_2$ or unsubstituted N, then
$R^1$ is hydrogen, hydroxy, cyano, —$(CH_2)_q$—OH, —$(CH_2)_q$—NRR', —$(CH_2)_q$—CN, lower alkyl, —$S(O)_2$-lower alkyl, —NR—$S(O)_2$-lower alkyl, —C(O)-lower alkyl, —NR—C(O)-lower alkyl, phenyl, or a piperidinyl-2-one;
if X is a N-atom, substituted by $R^1$, then
$R^1$ is hydrogen, —$(CH_2)_q$—OH, —$(CH_2)_q$—NRR', —$(CH_2)_q$—CN, lower alkyl, —$S(O)_2$-lower alkyl, aryl, or a five or six membered heteroaryl or —C(O)-lower alkyl provided that q is 2 or 3;
R and R' are each independently hydrogen or lower alkyl;
$R^2$ is hydrogen, halogen, lower alkyl, cyano, lower alkoxy substituted by halogen, lower alkyl substituted by halogen or is a five or six membered heteroaryl;
$R^3$ is hydrogen or halogen;
$R^4$ is hydrogen or lower alkyl;
n is 1 or 2; in case n is 2, $R^1$ may be the same or different;
o is 1 or 2; in case o is 2, $R^2$ may be the same or different;
P is 1 or 2; in case p is 2, $R^3$ may be the same or different;
q is 1, 2 or 3; and
s is 0, 1, 2, 3 or 4 wherein $(C)_s$ is additionally bonded to hydrogen atoms;
or a pharmaceutically active salt thereof, including all stereoisomeric forms, individual diastereoisomers and enantiomers of the compound of formula (I) as well as racemic and non-racemic mixtures thereof and a pharmaceutically acceptable carrier.

* * * * *